US012629185B2

(12) United States Patent
Lee et al.

(10) Patent No.: US 12,629,185 B2
(45) Date of Patent: May 19, 2026

(54) SYSTEM AND METHOD FOR JOINING BONEY STRUCTURES

(71) Applicant: Randall F. Lee, Southlake, TX (US)

(72) Inventors: Randall F. Lee, Southlake, TX (US);
Daniel S. Savage, Brecksville, OH (US); Alan W. Rorke, Bristol (GB)

(73) Assignee: Randall F. Lee, Southlake, TX (US)

( * ) Notice: Subject to any disclaimer, the term of this patent is extended or adjusted under 35 U.S.C. 154(b) by 448 days.

(21) Appl. No.: 18/123,765

(22) Filed: Mar. 20, 2023

(65) Prior Publication Data

US 2023/0225775 A1       Jul. 20, 2023

Related U.S. Application Data

(63) Continuation of application No. PCT/US2021/051348, filed on Sep. 21, 2021, and a continuation of application No. 17/372,327, filed on Jul. 9, 2021, now Pat. No. 11,839,547, and a continuation of application No. 17/248,943, filed on Feb. 13, 2021, now Pat. No. 11,058,542, and a continuation of application No. 17/175,649, filed on Feb. 13, 2021, now Pat. No. 11,160,589.

(60) Provisional application No. 63/130,323, filed on Dec. 23, 2020, provisional application No. 63/113,886, filed on Nov. 15, 2020, provisional application No. 63/081,187, filed on Sep. 21, 2020.

(51) Int. Cl.
*A61B 17/80*       (2006.01)
(52) U.S. Cl.
CPC ...... *A61B 17/8004* (2013.01); *A61B 17/8076* (2013.01)

(58) Field of Classification Search
CPC ............... A61B 17/8004; A61B 17/844; A61F 2/30749; A61F 2/4603
See application file for complete search history.

(56) References Cited

U.S. PATENT DOCUMENTS

| | | | |
|---|---|---|---|
| 3,506,982 | A | 4/1970 | Steffee |
| 3,552,389 | A | 1/1971 | Martin et al. |
| 4,484,570 | A | 11/1984 | Sutter et al. |
| 4,790,303 | A | 12/1988 | Steffee |
| 6,984,234 | B2 | 1/2006 | Bray |
| 7,488,320 | B2 | 2/2009 | Middleton |

(Continued)

FOREIGN PATENT DOCUMENTS

| | | |
|---|---|---|
| AU | 2013224006 B | 2/2017 |
| CA | 2635537 C | 5/2014 |

(Continued)

OTHER PUBLICATIONS

Final Office Action, mailed Aug. 5, 2025, by the USTPO, re U.S. Appl. No. 18/485,363.

(Continued)

*Primary Examiner* — Sameh R Boles
(74) *Attorney, Agent, or Firm* — Law Office of Bill Naifeh

(57)       ABSTRACT

Disclosed are system and methods that use at least one non-threaded anchor and an implant with at least one aperture to join boney structures, where the interaction of the head of the anchor with the implant aperture causes the anchor to move transversely with respect to an initial trajectory. This movement causes compression or distraction of the boney structures which are coupled to the anchors.

9 Claims, 37 Drawing Sheets

(56)                    References Cited

U.S. PATENT DOCUMENTS

| | | | |
|---|---|---|---|
| 7,572,280 | B2 | 8/2009 | Dickinson et al. |
| 8,267,997 | B2 | 9/2012 | Colleran |
| 8,268,000 | B2 | 9/2012 | Waugh et al. |
| 8,328,872 | B2 | 12/2012 | Duffield et al. |
| 8,361,155 | B2 | 1/2013 | Lambrecht et al. |
| 8,540,769 | B2 | 9/2013 | Janowski et al. |
| 8,641,766 | B2 | 2/2014 | Donner et al. |
| 8,764,831 | B2 | 7/2014 | Lechmann et al. |
| 8,882,775 | B2 | 11/2014 | Laposta et al. |
| 8,968,405 | B2 | 3/2015 | Kirwan et al. |
| 8,979,930 | B2 | 3/2015 | Glazer |
| 9,351,847 | B2 | 5/2016 | Reed et al. |
| 9,408,715 | B2 | 8/2016 | Donner et al. |
| 9,526,620 | B2 | 12/2016 | Slivka et al. |
| 9,566,165 | B2 | 2/2017 | Lee et al. |
| 9,937,055 | B1 | 4/2018 | Bernhardt et al. |
| 10,022,161 | B2 | 7/2018 | Blain et al. |
| 10,098,755 | B2 | 10/2018 | Kaufmann et al. |
| 10,195,051 | B2 | 2/2019 | Bergey et al. |
| 10,245,156 | B2 | 4/2019 | Chataigner et al. |
| 10,258,479 | B2 | 4/2019 | Stewart et al. |
| 10,376,377 | B2 | 8/2019 | Seifert et al. |
| 10,433,975 | B2 | 10/2019 | Ashleigh et al. |
| 10,478,310 | B2 | 11/2019 | Ameil et al. |
| 10,485,591 | B2 | 11/2019 | Lequette et al. |
| 10,631,999 | B2 | 4/2020 | Gilbride et al. |
| 10,758,370 | B2 | 9/2020 | Gilbride et al. |
| 11,058,542 | B1 | 7/2021 | Lee et al. |
| 11,160,589 | B1 | 11/2021 | Lee et al. |
| 11,839,547 | B2 | 12/2023 | Lee et al. |
| 11,872,141 | B2 | 1/2024 | Lee et al. |
| 2005/0182408 | A1 | 8/2005 | Pfefferle et al. |
| 2006/0195094 | A1 | 8/2006 | K et al. |
| 2009/0210062 | A1 | 8/2009 | Thalgott et al. |
| 2009/0254126 | A1 | 10/2009 | Orbay et al. |
| 2011/0098747 | A1 | 4/2011 | Donner et al. |
| 2012/0078371 | A1 | 3/2012 | Gamache et al. |
| 2012/0078373 | A1 | 3/2012 | Gamache et al. |
| 2013/0079879 | A1 | 3/2013 | Suh |
| 2013/0150968 | A1 | 6/2013 | Dinville et al. |
| 2013/0166029 | A1 | 6/2013 | Dinville et al. |
| 2013/0245767 | A1 | 9/2013 | Lee et al. |
| 2014/0180417 | A1 | 6/2014 | Bergey |
| 2015/0127109 | A1 | 5/2015 | Brett et al. |
| 2016/0074172 | A1 | 3/2016 | Lee et al. |
| 2016/0106550 | A1 | 4/2016 | Slivka et al. |
| 2016/0151171 | A1 | 6/2016 | Mozeleski et al. |
| 2016/0338853 | A1 | 11/2016 | Donner et al. |
| 2017/0007305 | A1 | 1/2017 | Hollis et al. |
| 2017/0071750 | A1 | 3/2017 | Urban et al. |
| 2017/0246007 | A1 | 8/2017 | Chataigner et al. |
| 2018/0177606 | A1 | 6/2018 | Reed et al. |
| 2018/0214280 | A1 | 8/2018 | Seifert et al. |
| 2018/0325694 | A1 | 11/2018 | Petersheim et al. |
| 2019/0000637 | A1 | 1/2019 | Gilbride et al. |
| 2019/0000638 | A1 | 1/2019 | Gilbride et al. |
| 2019/0105174 | A1* | 4/2019 | Kaufmann .............. A61F 2/447 |
| 2019/0183658 | A1 | 6/2019 | Lambrecht et al. |
| 2019/0328540 | A1 | 10/2019 | Seifert et al. |
| 2022/0087820 | A1 | 3/2022 | Lee et al. |
| 2022/0087821 | A1 | 3/2022 | Lee et al. |
| 2023/0225869 | A1 | 7/2023 | Lee et al. |

FOREIGN PATENT DOCUMENTS

| | | | |
|---|---|---|---|
| CN | 108969163 | A | 12/2018 |
| EP | 1968464 | B1 | 2/2012 |
| EP | 2419030 | B1 | 1/2017 |
| EP | 2701638 | B1 | 5/2017 |
| EP | 3207900 | B1 | 7/2018 |
| EP | 3470022 | A1 | 4/2019 |
| FR | 2954692 | A1 | 7/2011 |
| FR | 3005569 | A1 | 11/2014 |
| FR | 3016793 | A1 | 7/2015 |
| JP | 2017507000 | A | 3/2017 |
| JP | 2018187417 | A | 11/2018 |
| KR | 101555317 | B | 10/2015 |
| KR | 101636010 | B | 7/2016 |
| KR | 20160145538 | A | 12/2016 |
| RU | 2631208 | C2 | 9/2017 |
| WO | 2010121028 | A2 | 10/2010 |
| WO | 2011129973 | A1 | 10/2011 |
| WO | 2013062716 | A1 | 5/2013 |
| WO | 2016100158 | A1 | 6/2016 |
| WO | 2017029301 | A1 | 2/2017 |
| WO | 2017087020 | A1 | 5/2017 |
| WO | 2017186966 | A1 | 11/2017 |
| WO | 2018140352 | A1 | 8/2018 |
| WO | 2022061278 | A1 | 3/2022 |
| WO | 2022061302 | A1 | 3/2022 |

OTHER PUBLICATIONS

Final Office Action, mailed Jun. 25, 2025, by the USPTO, in U.S. Appl. No. 17/513,993.

International Search Report, by the ISA/US, mailed Jan. 24, 2022, regarding PCT/US2021/051348.

International Search Report, by the ISA/US, mailed Jan. 25, 2022, regarding PCT/US2021/051250.

Office Action, mailed Apr. 19, 2021, by the USPTO, regarding U.S. Appl. No. 17/175,649.

Written Opinion, by the ISA/US, mailed Jan. 24, 2022, regarding PCT/US2021/051348.

Written Opinion, by the ISA/US, mailed Jan. 25, 2022, regarding PCT/US2021/051250.

Office Action, dated Oct. 20, 2025, by the USPTO, re U.S. Appl. No. 17/513,993.

Office Action, dated Oct. 28, 2025, by the USPTO, in U.S. Appl. No. 18/123,739.

Office Action-Restriction, dated Aug. 13, 2025, by the USPTO, re U.S. Appl. No. 18/123,739.

Notice of Allowance, mailed Sep. 13, 2023, by the USPTO, re U.S. Appl. No. 17/372,327.

Office Action, dated Mar. 5, 2025, by the USPTO, re U.S. Appl. No. 17/513,993.

Notice of Allowance, mail Jul. 1, 2021, by the USPTO, re U.S. Appl. No. 17/175,649.

Notice of Allowance, mail Apr. 28, 2021, by the USPTO, re U.S. Appl. No. 17/248,943.

Office Action-Restriction Requirement, mailed Apr. 6, 2021, by the USPTO, re U.S. Appl. No. 17/248,943.

Office Action-Restriction Requirement, mailed Mar. 30, 2021, by the USPTO, re U.S. Appl. No. 17/175,649.

Office Action, mailed Jun. 2, 2023, by the USPTO, re U.S. Appl. No. 17/372,327.

Notice of Allowance, dated Dec. 16, 2025, by the USPTO, in U.S. Appl. No. 18/485,363.

Notice of Allowance, dated Mar. 5, 2026, by the USPTO, in U.S. Appl. No. 18/123,739.

* cited by examiner

104 h1

100

104 h2

100

902

1100

900 or 900'

1308a
1308b
1300
1302
1304
1100
1350a
1350b 900 or 900'

1208a
1208b
1200
1202
1204
1250a
1250b
1000

SYSTEM AND METHOD FOR JOINING BONEY STRUCTURES

CROSS REFERENCE TO RELATED APPLICATIONS

This application is a continuation of PCT International Application No. PCT/US2021/051348, filed Sep. 21, 2021, entitled SYSTEM AND METHOD FOR JOINING BONEY STRUCTURES, which claims priority to U.S. patent application Ser. No. 17/372,327, filed on Jul. 9, 2021, entitled SYSTEM AND METHOD FOR JOINING BONEY STRUCTURES, U.S. patent application Ser. No. 17/248, 943, filed on Feb. 13, 2021, now U.S. Pat. No. 11,058,542, entitled SYSTEM AND METHOD FOR JOINING BONEY STRUCTURES, and U.S. patent application Ser. No. 17/175,649, filed on Feb. 13, 2021, now U.S. Pat. No. 11,160,589, entitled SYSTEM AND METHOD FOR JOINING BONEY STRUCTURES; and claims the benefit of the filing dates of the following U.S. provisional patent applications: U.S. Provisional Application No. 63/130,323, filed on Dec. 23, 2020, entitled SYSTEM AND METHOD FOR JOINING BONEY STRUCTURES, U.S. Provisional Application No. 63/113,886, filed on Nov. 15, 2020, entitled SYSTEM AND METHOD FOR JOINING BONEY STRUCTURES, and U.S. Provisional Application No. 63/081,187, filed on Sep. 21, 2020, entitled SYSTEM AND METHOD FOR JOINING BONEY STRUCTURES. The disclosures of all of the above patent applications are hereby incorporated by reference for all purposes. This application also incorporates by reference for all purposes a commonly owned patent application entitled SYSTEM AND METHOD FOR JOINING BONEY STRUCTURES, PCT International Application No. PCT/US2021/051250, filed Sep. 21, 2021, entitled SYSTEM AND METHOD FOR JOINING BONEY STRUCTURES.

TECHNICAL FIELD

The disclosed invention relates in general to orthopedic and dental surgically implanted devices, and in particular to implantable devices which use a plurality of non-threaded anchors with an implant or plate to compress and join boney structures.

BACKGROUND INFORMATION

Over a hundred years ago surgeons determined that a combination of screws and plates worked as a method of internal fixation of two or more bone structures. In time surgeons empirically learned that placing two or more bones in mechanical compression greatly improved the speed and quality of bone healing. Mechanical compression was then rendered through external devices and internally fixated with the screw plate device.

Many believe that localized bone compression is the orthopaedic standard for bone healing. Current art uses plates with dedicated screw channels or directive apertures that determine the range of screw angulation and the resultant course of the screw's trajectory.

In many orthopedic related procedures, however, such as spinal, sternal chest closure, dental, and numerous orthopedic reconstructions, plates and screws have not been found to follow compressive bone healing principals. Instead, the screw plate configurations stabilize the boney structures, but do not typically compress the bone structures together.

Furthermore, threaded anchors such as screws have many disadvantages, including the tendency to back out of a boney structure over time.

Therefore, what is needed is a novel plate anchor system that consistently achieves bone compression or distraction of two boney structures.

SUMMARY

In response to these and other problems, in one embodiment, there is a system that includes non-threaded anchors that follow a trajectory into a boney structure and then a non-threaded head of the anchor interacts with the aperture features in an supra implant to cause the anchor to move transversely within the aperture which can cause compression or distraction of boney structures coupled to the anchors.

These and other features, and advantages, will be more clearly understood from the following detailed description taken in conjunction with the accompanying drawings. It is important to note the drawings are not intended to represent the only aspect of the invention.

DETAILED DESCRIPTION

Figure 1A:
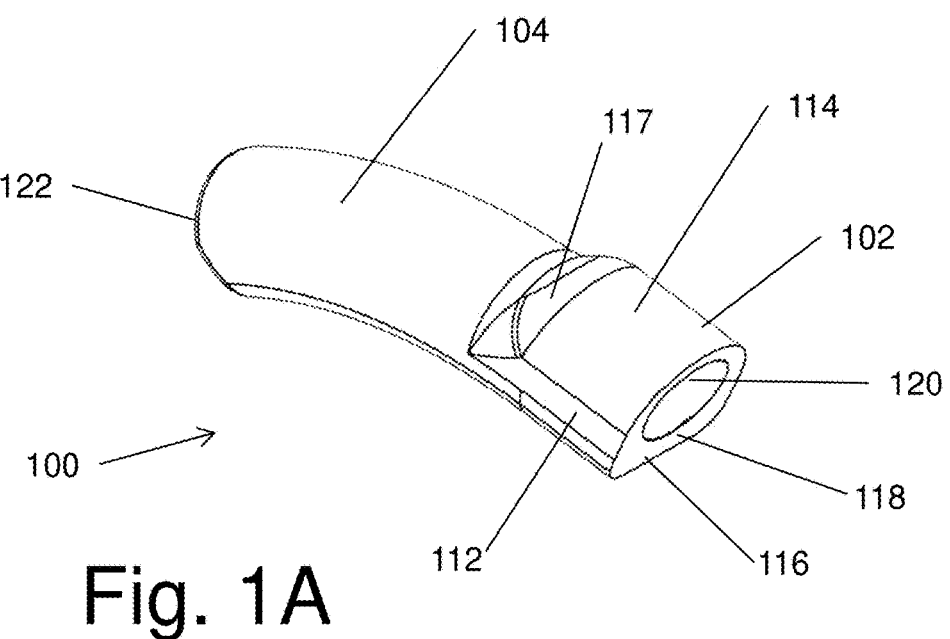
FIG. 1A is a perspective view of one aspect of a non-threaded anchor which can be used in one or more aspects of the present invention.

For the purposes of promoting an understanding of the principles of the present inventions, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

When directions, such as upper, lower, top, bottom, clockwise, counter-clockwise, are discussed in this disclosure, such directions are meant to only supply reference directions for the illustrated figures and for orientation of components in respect to each other or to illustrate the figures. The directions should not be read to imply actual directions used in any resulting invention or actual use. Under no circumstances, should such directions be read to limit or impart any meaning into the claims.

Figure 1B:
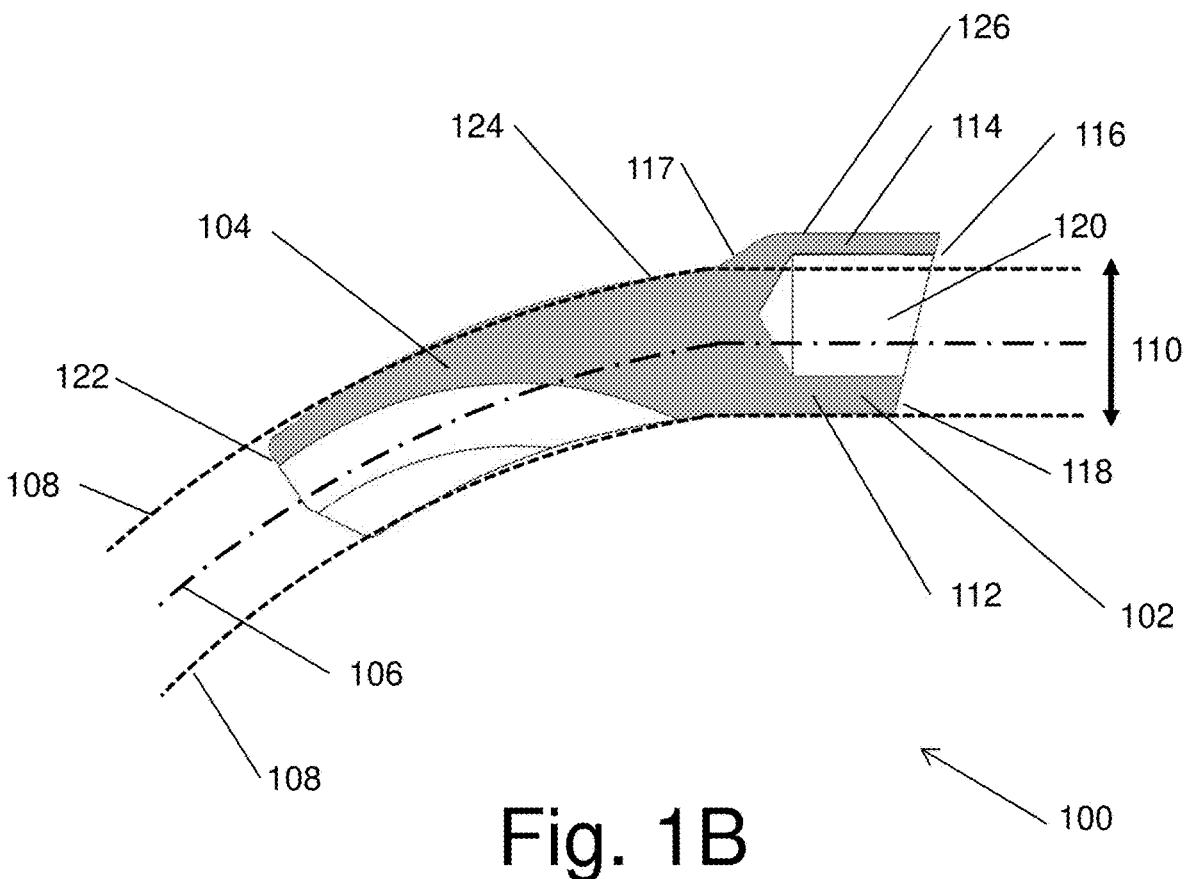
FIG. 1B is a longitudinal section view of the non-threaded anchor of FIG. 1A.
Figure 1C:
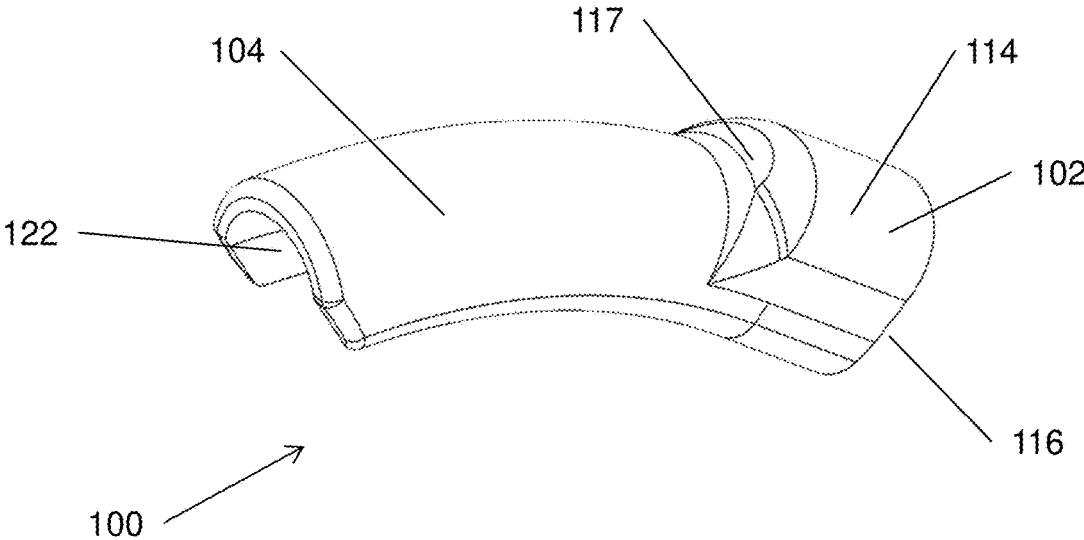
FIG. 1C is a top perspective view of the non-threaded anchor of FIG. 1A orientated so that the distal end is illustrated.
Figure 1D:
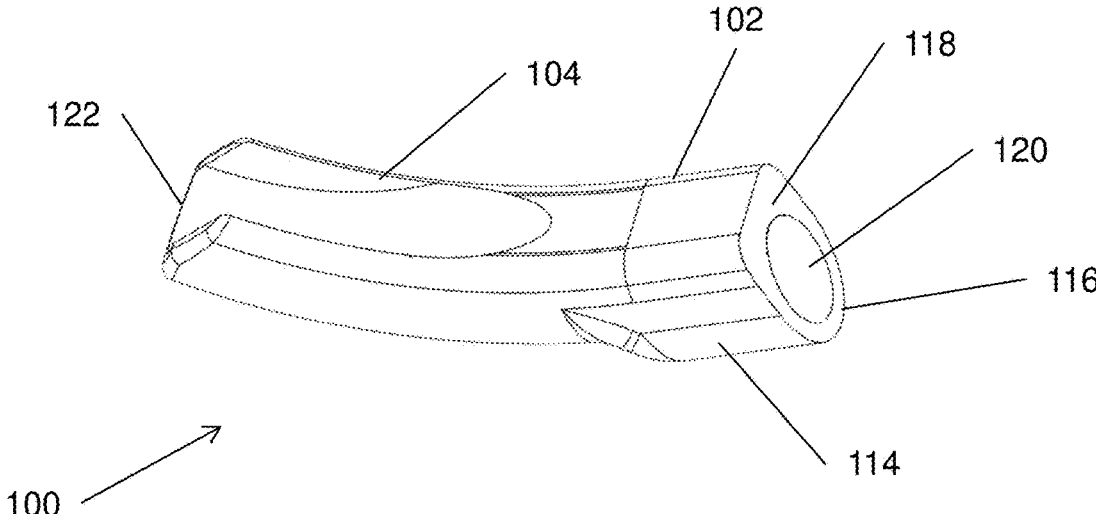
FIG. 1D is a bottom perspective view of the non-threaded anchor of FIG. 1A.

Anchors:

FIG. 1A is a proximal perspective view of one aspect of a non-threaded anchor 100 which can be used with several embodiments of the present invention. FIG. 1B is a longitudinal section view of the non-threaded anchor 100. FIG. 1C is a top perspective view of the anchor 100 orientated to illustrate a distal end 122. In contrast, FIG. 1D is a bottom perspective view of the anchor 100.

Turning now to FIGS. 1A through 1D, in the illustrative embodiment, the non-threaded anchor 100 includes a non-threaded proximal end or head portion 102 which is coupled to a non-threaded elongated body portion 104. The non-threaded elongated body 104 has a longitudinal or center axis 106, which in this embodiment, partially defines an initial trajectory into a boney structure as will further be discussed below. In the illustrated embodiment, the head portion 102 and the elongated body portion 104 share the central axis 106 which is curved within the elongated body portion 104 and straight within the head portion 102. In other embodiments, the elongated body portion 104 may be straight in which the center axis 106 would also be straight. In yet other embodiments, the head portion 102 may be curved and likewise, the center axis 106 within the head portion may also be curved.

FIG. 1B is a section view of the anchor 100 with the addition of dotted lines 108. For purposes of illustration, the dotted lines 108 are boundary lines that represent the portion of the anchor 100 that is generally equal distance with respect to the center axis 106 in a direction 110 that is generally normal or transverse to the direction of the center axis 106. For purposes of this disclosure, any portion of the head portion 102 that is outside of the dotted lines 108 is defined as "offset" or eccentric to the center axis 106. As can be seen most clearly in FIG. 1B, the non-threaded head portion 102 includes a first or symmetrical head portion 112 that is substantially within the boundary lines 108 and a second portion or "offset" portion 114 of the head portion 102 that is outside of the boundary lines 108. Looking from the perspective of FIG. 1B, the boundary lines 108 are generally symmetrical or equal distance from the center axis 106 in a direction 110 which is normal to the center axis. Thus, for purposes of this disclosure, the second or offset portion 114 of the head portion 102 that is outside of the boundary lines 108 is defined as an offset portion 114 from the center axis. In other words, an unsymmetrical mass or structure beyond an equal distance line from the center axis is considered to be an "offset" portion 114 of the head portion 102 for purposes of this disclosure. In this embodiment, a transition or blended surface 117 allows for the smooth transition between the surface of the elongated body portion 104 and the offset anchor head portion 114.

In certain embodiments, a proximal end 116 of the anchor 100 contains an engagement surface 118 that is angled with respect to the normal direction 110 of center axis 106. In certain embodiments, the engagement surface 118 may have engagement features, such as aperture 120 for engaging with various embodiments of insertion instruments. In the illustrative embodiment, the longitudinal axis of the aperture 120 may be parallel with respect to the center axis 106. In other embodiments, the longitudinal axis of the aperture 120 may be positioned at an angle to the longitudinal axis 106.

Figure 1E:
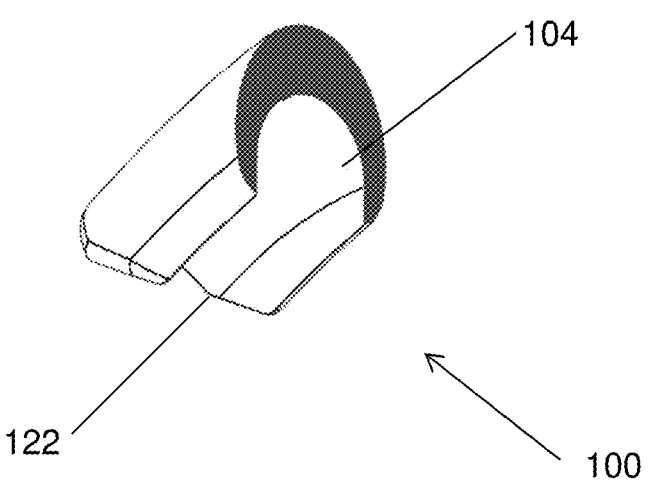
FIGS. 1E through 1H are transverse sectional views of the non-threaded anchor of FIG. 1A.
Figure 1F:
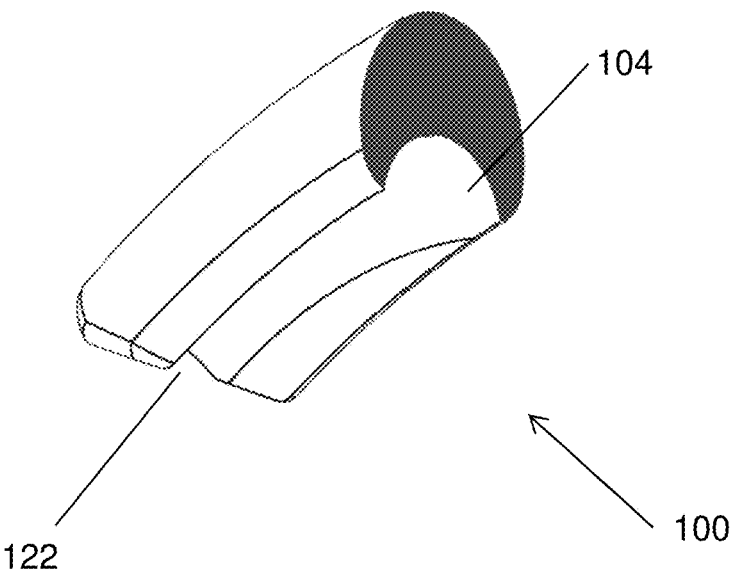

As can be best seen in FIGS. 1C and 1D, a distal end 122 of the anchor 100 is designed to penetrate and be pushed through a boney structure. Consequently, at the distal end 122 the cross-sectional area of the body portion 104 is significantly reduced which also reduces the force necessary to push the distal end 122 through the boney structure (not shown). In the illustrative embodiment as best seen in FIG. 1C, the distal end 122 has a generally semi-circular or horseshoe shaped cross-sectional area. For instance, FIG. 1E is a partial perspective section view where the body portion 104 has been cut close to the distal end 122. The cut in FIG. 1E is in a vertical direction and illustrates the horseshoe shape of cross-section of the body portion 104 when the section is cut close to the distal end 122. In contrast, FIG. 1F is a partial perspective section view where the body portion 104 has been cut at a point between the distal end 122 and a midsection point 124 (see FIG. 1B). The cut in FIG. 1F is in a vertical direction and illustrates a substantial thickening of the horseshoe shape of cross-section of the body portion 104 of the anchor 100.

Figure 1G:
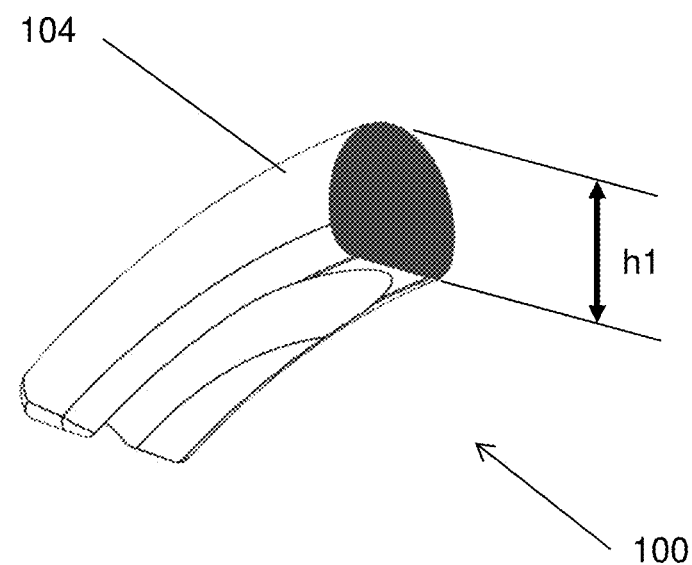
Figure 1H:
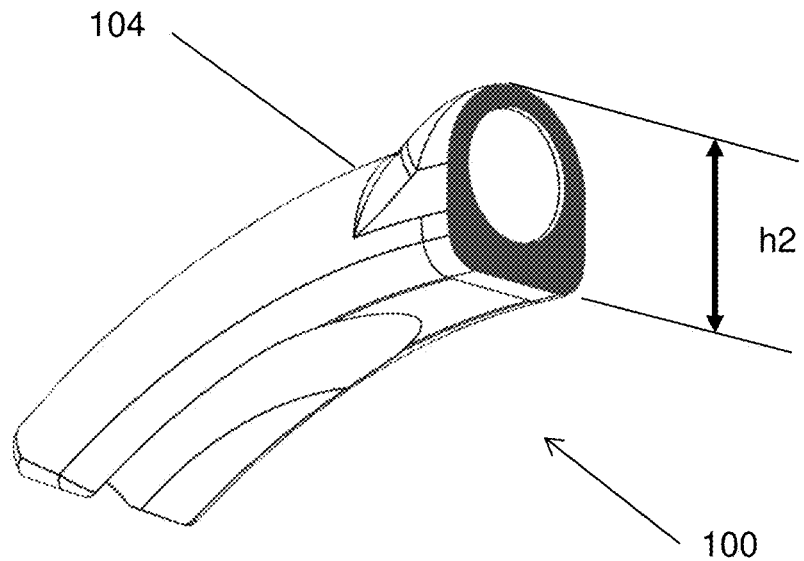

FIG. 1G is a partial perspective view where the body portion 104 has been cut at the midsection point 124 (see FIG. 1B). The cut in FIG. 1G is in a vertical direction and illustrates a cross-sectional shape of a solid partially elliptical segment. As illustrated, the body portion 104 has a vertical thickness or height of h1 at this cut point. In contrast, FIG. 1H is a partial perspective view where the head portion 102 has been cut around a point 126 (see FIG. 1B). As illustrated, the head portion 102 has a vertical thickness or height of h2 at this cut point. Note the difference in between the height h1 in FIG. 1G and the height h2 in FIG. 1H is created by the offset portion 114 of the head portion 102 as discussed above.

Although the anchor 100 as illustrated and discussed above uses a tapering horseshoe cross-sectional shape for the body portion 104, any cross-sectional shape could be used and still be within the inventive aspects of the present invention. Such shapes include triangular, diamond, rectangular, circular or equilateral polygon cross-sectional shapes or a combination thereof. For instance, a triangular cross-sectional shape could be used on the body portion 104 while the head portion 102 may be largely circular in cross-sectional shape. If such shapes are used, generally the body portion will taper down from the head portion 102 to the distal end 122. In other words, the cross sectional areas of the body portion 104 will decrease as the distal end is approached.

Figure 2A:
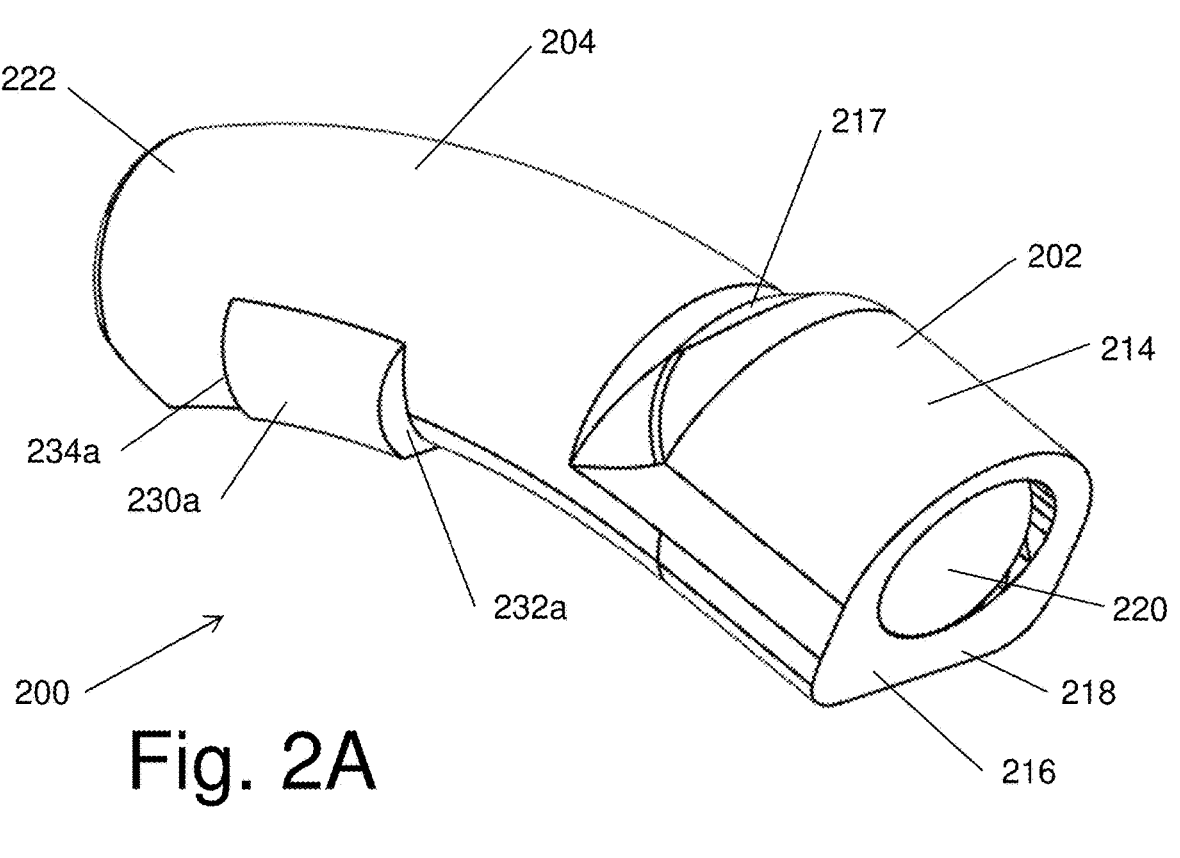
FIG. 2A is a perspective view of an alternative aspect of a non-threaded anchor that can be used in one or more aspects of the present invention.
Figure 2B:
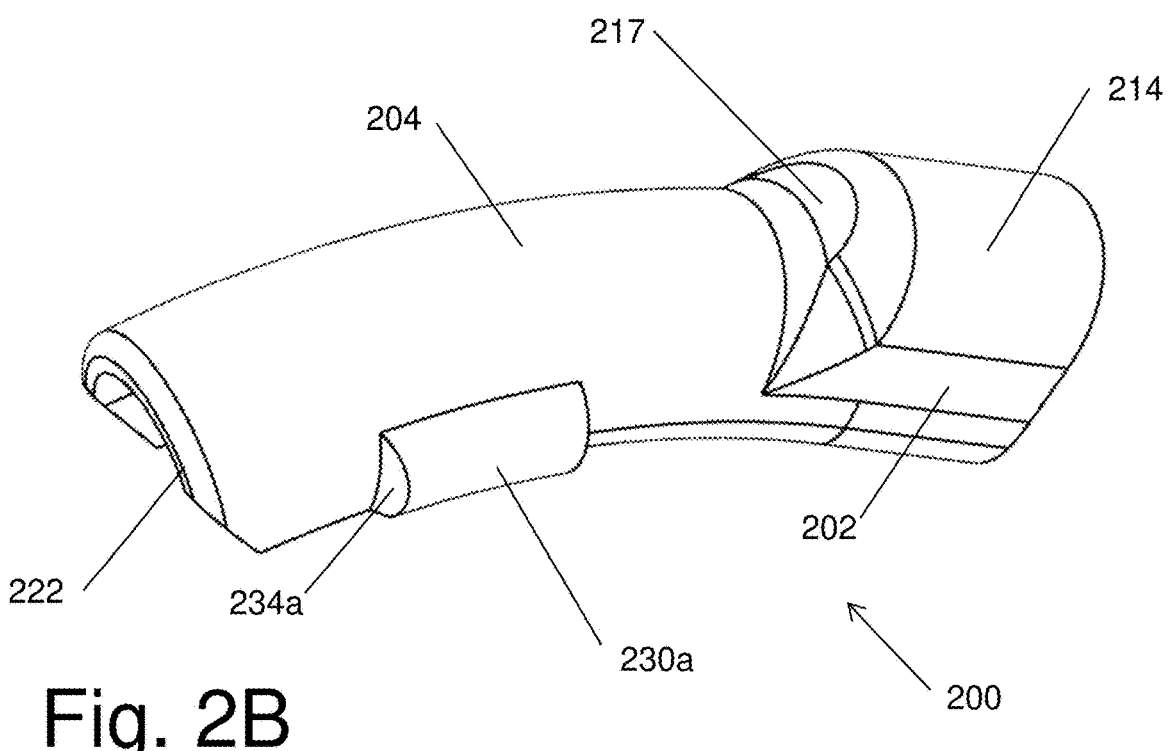
FIG. 2B is a top perspective view of the non-threaded anchor of FIG. 2A orientated so that the distal end is illustrated.

Anchors with Side Rails:

A second embodiment an anchor is illustrated in FIG. 2A which is a perspective view of an alternative anchor 200 and also can be used with several embodiments of the present invention. FIG. 2B is a top perspective view of the anchor 200 orientated to illustrate a distal end 222. In contrast, FIG. 2C is a bottom perspective view of the anchor 200.

For brevity and clarity, some of the description of those parts which are identical or similar to those described in connection with the first embodiment of the anchor illustrated in FIGS. 1A through 1H will not be repeated here. Reference should be made to the foregoing paragraphs with the following description to arrive at a complete understanding of this second embodiment.

Figure 2C:
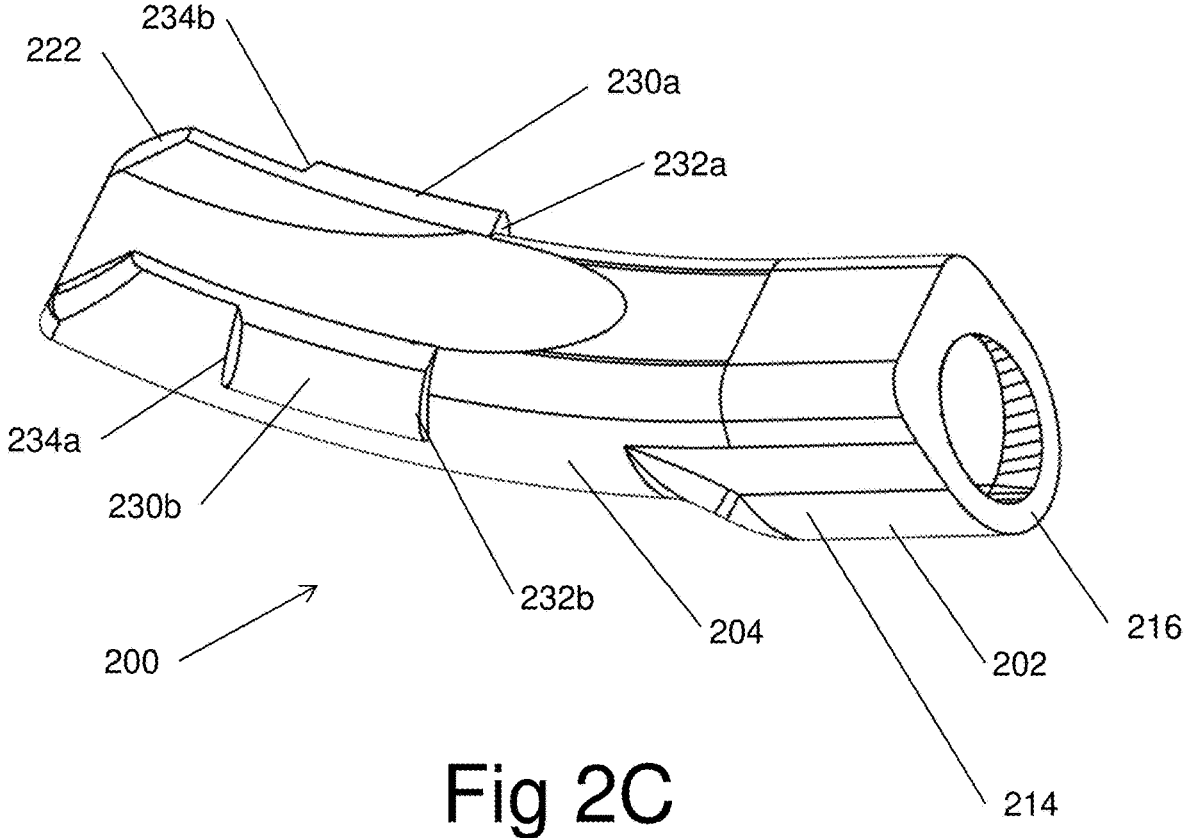
FIG. 2C is a bottom perspective view of the non-threaded anchor of FIG. 2A.

Turning now to FIGS. 2A through 2C, in the illustrative embodiment, the non-threaded anchor 200 includes a non-threaded proximal end or head portion 202 which is coupled to a non-threaded longitudinal body portion 204.

In certain embodiments, the head portion includes a proximal end 216 which includes a tool engagement surface 218 that is angled in a manner similar to the tool engagement surface 118 discussed above. In certain embodiments, the tool engagement surface 218 may have engagement features, such as aperture 220 for engaging with various embodiments of insertion instruments and tools as will be explained below.

In certain embodiments, the head portion 202 also includes an offset portion 214 which extends out on one side in a direction normal or transverse to the central axis of the head 202 as explained above in reference to FIG. 1B. A transition or blended surface 217 allows for the smooth transition between the surface of the elongated body portion 204 and the offset anchor head portion 214.

The distal end 222 of the anchor 200 is designed to penetrate and be pushed through a boney structure. Consequently, at the distal end 222 the cross-sectional area of the body portion 204 is significantly reduced which also reduces the force necessary to push the distal end 222 through the boney structure. In the illustrative embodiment the distal end 222 has a generally semi-circular or horseshoe shaped cross-sectional area. However, the cross-sectional shape is exemplary and any cross-sectional shape may be used.

The primary difference between the anchor 100 and the anchor 200 is the addition of side rails 230a and 230b extending in a lateral direction or perpendicularly out from the surface on both sides of the body portion 204 (side rail 230b is not shown in FIGS. 2A and 2B). As will be explained below, the side rails 230a and 230b facilitate the centering of the anchor 200 within an aperture of an implant (not shown) when the body portion 204 is pushed through the aperture. In certain embodiments, the side rails 230a and 230b are curved and have the shape of a circular segment in cross-section as illustrated by a proximal surface 232a of the side rail 230a in FIG. 2A and a proximal surface 232b in FIG. 2C which extend out from the surface of body portion 204 in a lateral or perpendicular manner. In contrast, the side rails 230a and 230b also have distal or engaging surface 234a and 234b respectively. The surfaces 234a and 234b are angled with respect to the surface of the body portion 204 to reduce the engaging force necessary to penetrate into the boney structure. The engaging surface 234a is best illustrated in FIG. 2B.

As will be explained below in greater detail, side rails 230a and 230b engage correspondingly shaped channels or grooves defined within apertures of an implant to assist in guiding an anchor along a trajectory as the anchor penetrates the boney structure.

Figure 3A:
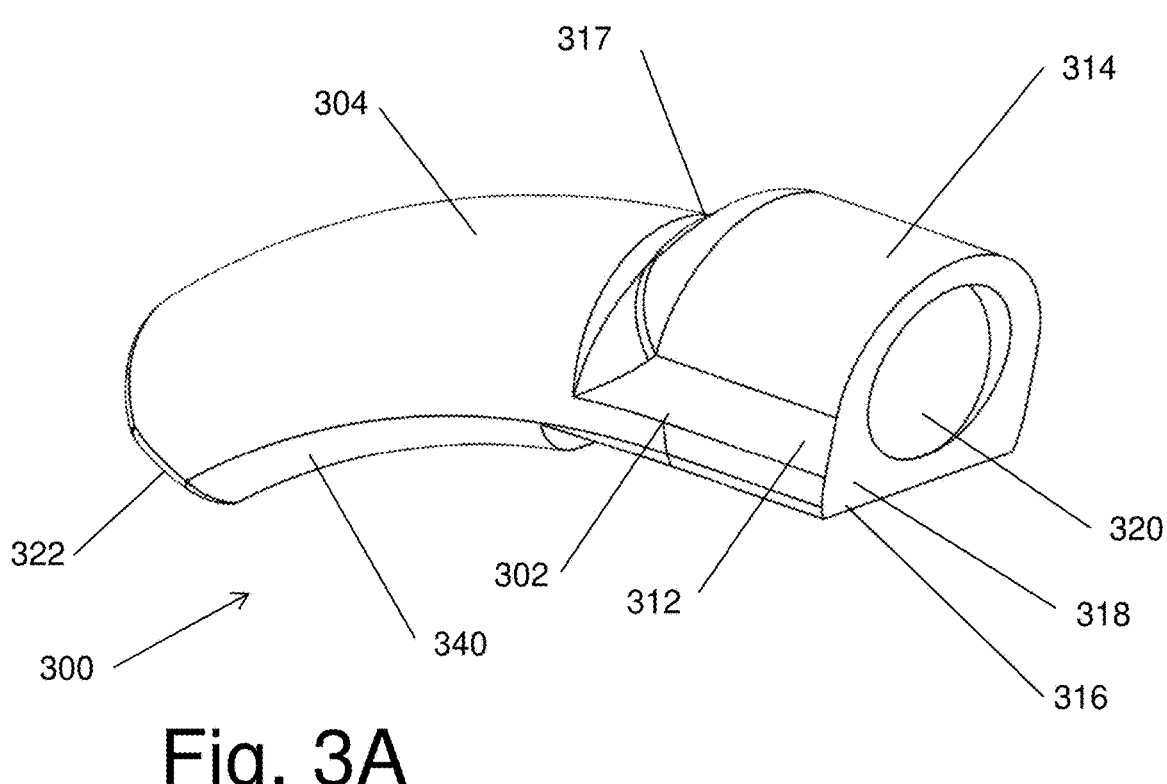
FIG. 3A is a perspective view of one aspect of a non-threaded anchor that can be used in one or more aspects of the present invention.
Figure 3B:
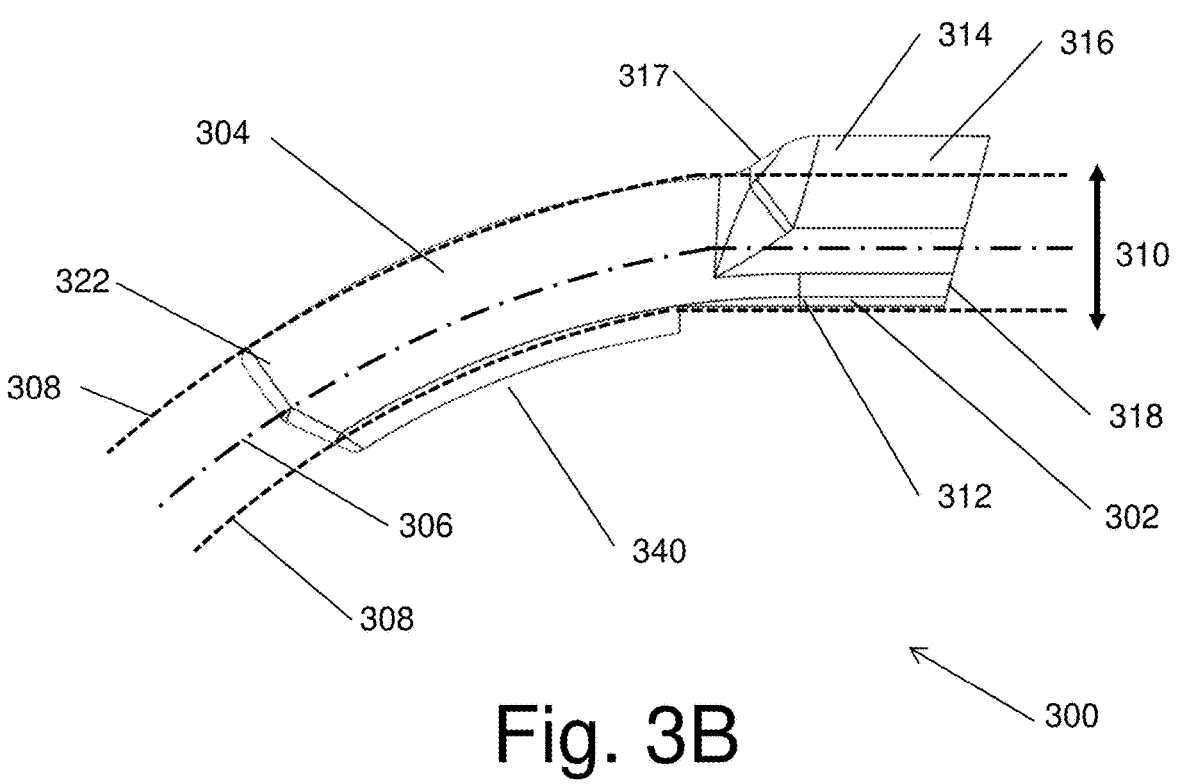
FIG. 3B is a longitudinal side view of the non-threaded anchor of FIG. 3A.
Figure 3C:
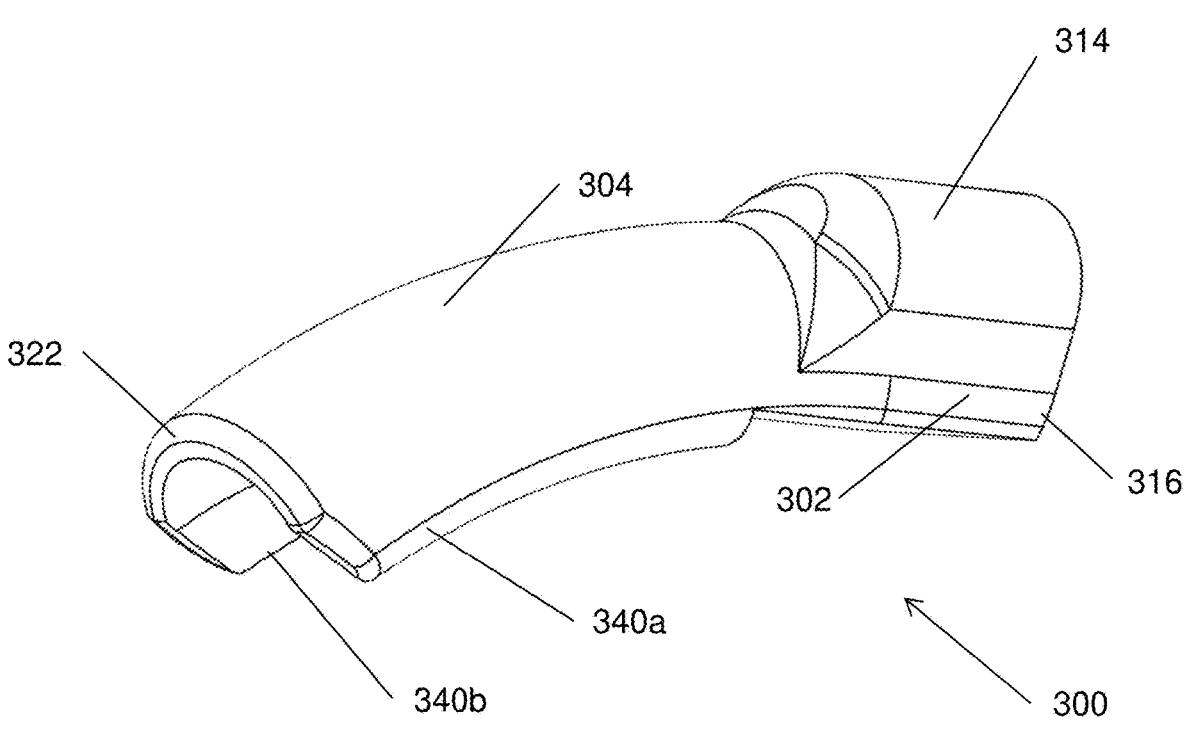
FIG. 3C is a top perspective view of the non-threaded anchor of FIG. 3A orientated so that the distal end is illustrated.
Figure 3D:
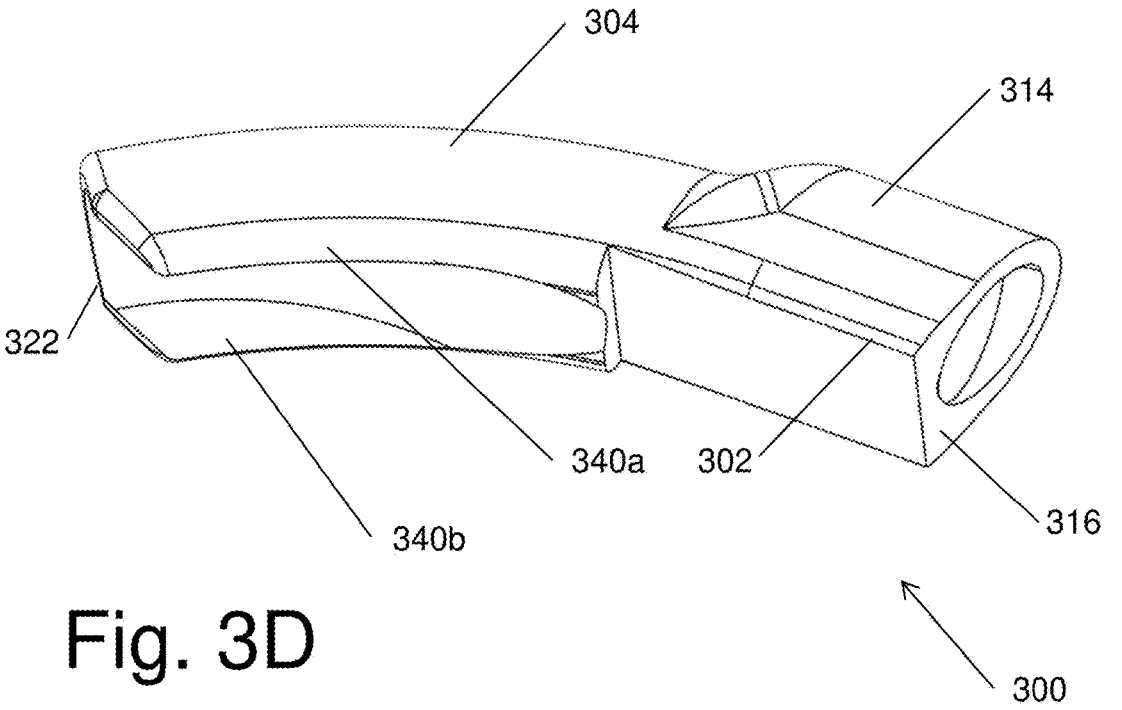
FIG. 3D is a bottom perspective view of the non-threaded anchor of FIG. 3A.

Anchors with a Stepped Surface:

A third embodiment an anchor is illustrated in FIG. 3A which is a side perspective view of an alternative anchor 300 which can be used with several embodiments of the present invention. FIG. 3B is a longitudinal side view of the anchor 300. FIG. 3C is a top perspective view of the anchor 300 orientated to illustrate a distal end 322. In contrast, FIG. 3D is a bottom perspective view of the anchor 300.

For brevity and clarity, some of the description of those parts which are identical or similar to those described in connection with the first two embodiments illustrated in FIGS. 1A through 2C will not be repeated here. Reference should be made to the foregoing paragraphs with the following description to arrive at a complete understanding of this second embodiment.

Turning now to FIGS. 3A through 3D, in the illustrative embodiment, the non-threaded anchor 300 includes a non-threaded proximal end or head portion 302 which is coupled to a non-threaded longitudinal body portion 304. The non-threaded elongated body 304 has a center axis 306, which in this embodiment, partially defines an initial trajectory into a boney structure as will further be discussed below.

FIG. 3B is a longitudinal side view of the anchor 300 illustrating the center axis 306 and with the addition of dotted lines 308. For purposes of illustration, the dotted lines 308 are "boundary" lines that are meant to represent the portion of the anchor that is generally equal distance with respect to the center axis 306 in a direction 310 that is generally normal to the direction of the center axis 306. For purposes of this disclosure, any portion of the head portion 302 that is outside of the dotted lines 308 is defined as "offset" or eccentric to the center axis 306. As can be seen most clearly in FIG. 3B, the non-threaded head 302 includes a first portion 312 of the head 302 that is substantially within the boundary lines 308 and a second portion 314 of the head portion 302 that is outside of the boundary lines 308.

Looking from the perspective of FIG. 3B, the boundary lines 308 are generally symmetrical or equal distance from the center axis 306 in a direction 310 which is normal or transverse to the center axis. Thus, for purposes of this disclosure, the second or portion 314 of the head portion 302 that is outside of the boundary lines 308 is defined as an offset portion 314 from the center axis. A transition or blended surface 317 allows for the smooth transition between the surface of the elongated body portion 304 and the offset anchor head portion 314.

In certain embodiments a proximal end 316 of the anchor 300 contains a tool engagement surface 318 that is angled with respect to the normal direction 310. In certain embodiments, the tool engagement surface 318 may have engagement features, such as aperture 320 (see FIG. 3A) for engaging with various embodiments of insertion instruments and tools as will be explained below.

As can be best seen in FIGS. 3C and 3D, a distal end 322 of the anchor 300 is designed to penetrate and be pushed through a boney structure. Consequently, at the distal end 322 the cross-sectional area of the body portion 304 is significantly reduced which also reduces the force necessary to push the distal end 322 through the boney structure. In the illustrative embodiment as best seen in FIG. 3C, the distal end 322 has a generally semi-circular or horseshoe shaped cross-sectional area and is similar in cross sectional shape to the embodiment illustrated in FIGS. 1E through 1H described above.

The primary difference between the anchor 300 and the anchor 100 is the addition of an opposing step or stepped protrusions 340 positioned along the body portion 304 as illustrated in FIGS. 3A through 3D. In certain embodiments, the opposing step or stepped protrusions 340 is on a side of the longitudinal axis 306 opposite from or opposing the offset head portion 314 and is also outside the boundary lines 308 as illustrated in FIG. 3B. As will be explained below, the opposing step or stepped protrusions 340 facilitate the centering or positioning of the anchor 300 within an aperture of an implant (not shown) when the body portion 304 is pushed through the aperture. Once the opposing step or stepped protrusions 340 clear the aperture, the opposing step 340 when combined with the offset head portion 314 allows for a greater shift of the boney element in the direction 310 when the anchor head 302 is fully seated within the implant (not shown).

As illustrated in FIG. 3C and FIG. 3D, in the illustrative embodiment of the anchor 300, there are actually two steps or stepped protrusions 340a and 340b due to the nature of the cross-sectional U-shape of the body portion 304.

In certain embodiments, the anchors 100, 200, and 300 discussed above may be fabricated from any number of biocompatible implantable materials, including but not limited to Titanium Alloys (Ti 6Al4V ELI, for example), commercially pure titanium, Chromium Cobalt (Cr—Co) and/or stainless steels. In yet other embodiments, the anchors may also be manufactured from polymer, including Carbon Fiber Reinforced Polymer ("CFRP") with a high carbon mass percentage. Furthermore in some embodiments, as explained below, the anchors may be formed using a shape memory alloy, such as Nitinol®.

Exemplary Supra Implant Embodiments

Figure 4A:
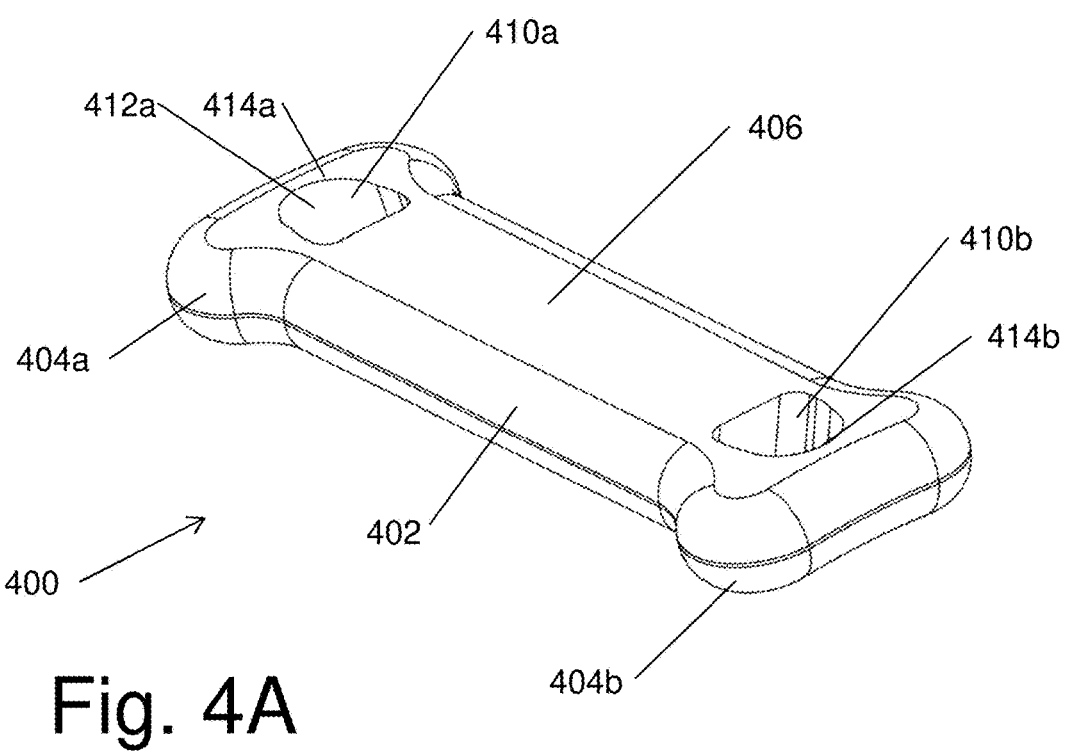
FIG. 4A is an isometric view of one embodiment of a supra plate which can be used with different aspects of the present invention.
Figure 4B:
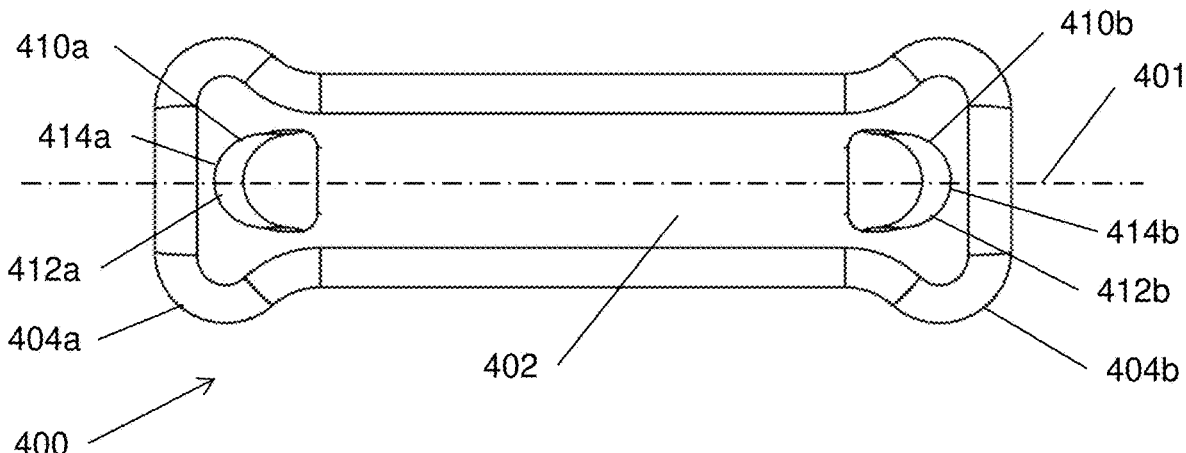
FIG. 4B is a top view of one embodiment of the implant of FIG. 4A.
Figure 4C:
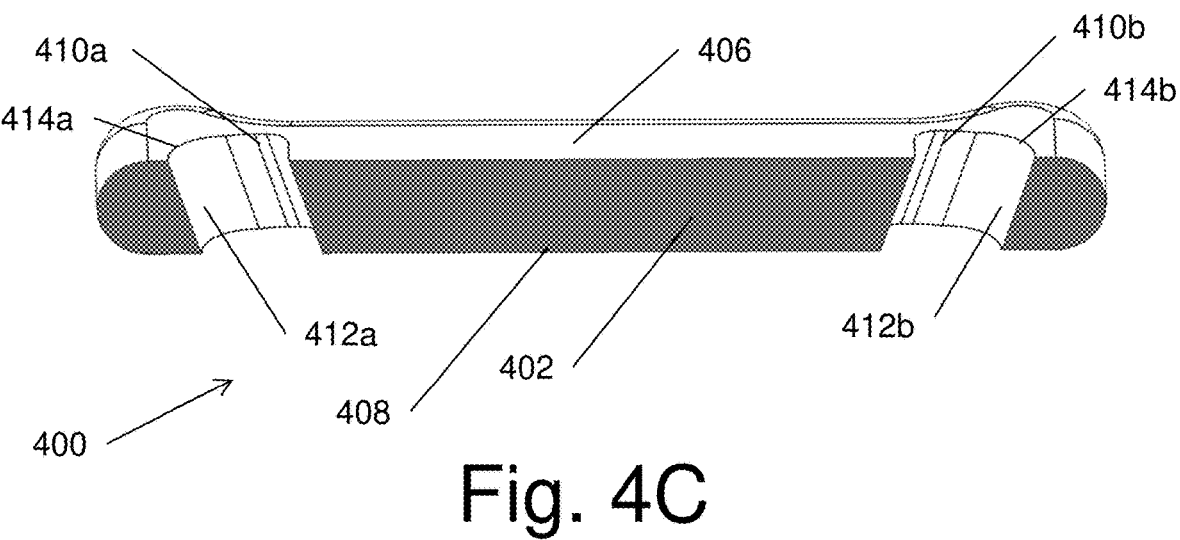
FIG. 4C is an isometric section view of one embodiment of the implant of FIG. 4A.

A Supra Plate for Receiving Non-Threaded Anchors:

FIG. 4A is an isometric illustration of a supra bone implant or supra implant (also known in the art as a fixation plate, insert plate, or insert). FIG. 4B is a top view of the supra implant 400 and FIG. 4C is a sectional perspective view of the supra implant 400. The implants disclosed herein, such as supra implant 400, may be manufactured from any number of implant grade materials, including, but not limited to Titanium and Titanium Alloys, as well as Carbon Fiber Reinforced Polymer (CFRP) and shape memory alloys as explained below.

In the illustrated embodiment of FIGS. 4A, 4B and 4C, the supra implant 400 has an elongated main body portion 402 with end portions 404*a* and 404*b* on each side of the main body portion. In certain embodiments, the main body portion 402 and the end portions 404*a* and 404*b* are all aligned along a longitudinal axis 401 (FIG. 4B). The supra implant 400 has a proximal surface 406 and a distal surface 408 for engaging or for placement next to one or more boney structures.

In certain embodiments, the end portions 404*a* and 404*b* have apertures 410*a* and 410*b* defined therethrough for accepting a non-threaded anchor, such as anchor 100 described above. In certain embodiments, the apertures 410*a* and 410*b* are non-threaded and may have an engagement feature (such as curved engaging surfaces 412*a* and 412*b* defined therein which are sized to receive and engage a surface of the non-threaded anchor 100 or an engagement edge 414*a* and 414*b*). In certain embodiments, the interaction of the engagement feature (e.g., inwardly sloped engaging surfaces 412*a* and 412*b* with the longitudinal shape or geometry of the elongated body portion 104 of non-threaded anchor 100) defines an initial insertion trajectory for the non-threaded anchor. For purposes of this disclosure the "initial trajectory" is the path of movement of the elongated body portion 104 of an anchor 100 starting when the elongated body portion 104 is first introduced into the aperture (e.g. either aperture 410*a* or 410*b*) and ending when the head portion 102 of the anchor 100 first comes into contact with the engaging features (such as surfaces 412*a* and 412*b* forming a portion of the inside of the aperture or the engaging edges 414*a* and 414*b*).

In yet other embodiments, there may be an implant (not shown) specifically designed for anchors with steps or stepped protrusions, such as an anchor 300. Such an implant would be similar to the implant 400 except that the apertures 410*a* and 410*b* may be wider along the horizontal axis to account for the extra depth of the steps or stepped protrusions.

Figure 4D:
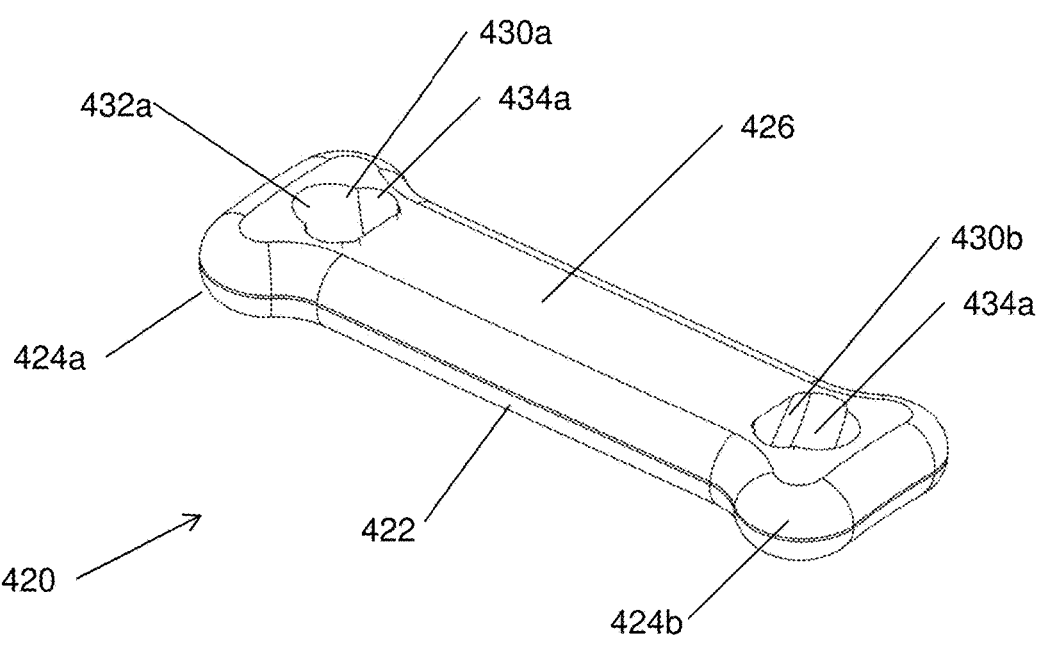
FIG. 4D is an isometric view of an alternative embodiment of a supra plate which can be used with different aspects of the present invention.
Figure 4E:
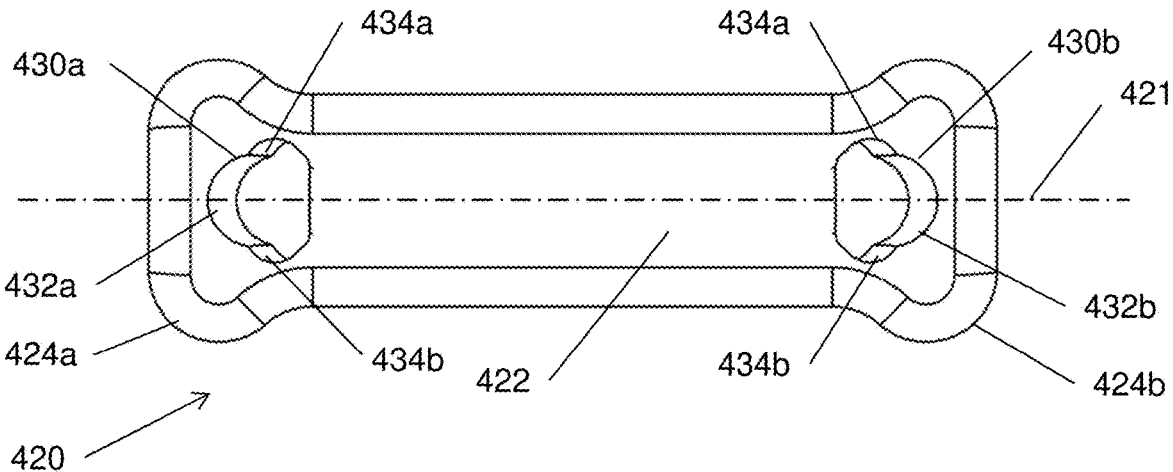
FIG. 4E is a top view of one embodiment of the implant of FIG. 4D.
Figure 4F:
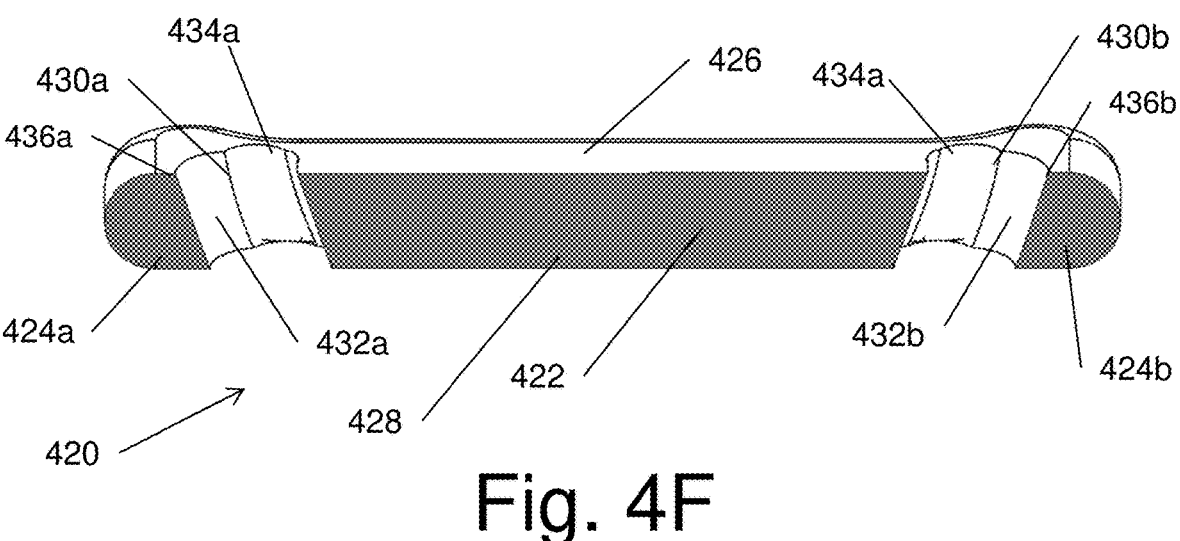
FIG. 4F is an isometric section view of one embodiment of the implant of FIG. 4D.

A Supra Plate for Compression and for Receiving Anchors with Rails:

FIG. 4D is an isometric illustration of an alternative supra bone implant. FIG. 4E is a top view of the supra implant 420 and FIG. 4F is a sectional perspective view of the supra implant 420. For brevity and clarity, some of the description of those parts which are identical or similar to those described in connection with the first embodiment of the supra implant 420 illustrated above will not be repeated here. Reference should be made to the foregoing paragraphs with the following description to arrive at a complete understanding of this second embodiment of the supra implant.

In the illustrated embodiment of FIGS. 4D, 4E and 4F, the supra implant 420 has an elongated main body portion 422 with end portions 424*a* and 424*b* on each side of the main body portion. In certain embodiments, the main body portion 422 and the end portions 424*a* and 424*b* are all aligned along a longitudinal axis 421 (FIG. 4E). The supra implant 420 has a proximal surface 426 and a distal surface 428 (FIG. 4F) for engaging or for placement next to one or more boney structures.

In certain embodiments, the end portions 424*a* and 424*b* have apertures 430*a* and 430*b* defined therethrough for accepting a non-threaded anchor, such as anchor 200 described above. In certain embodiments, the apertures 430*a* and 430*b* are non-threaded and may have engagement features such as an engagement edges 436*a*-436*b* and/or curved or straight engaging surfaces 432*a* and 432*b* defined therein which are sized to receive and engage a surface of the non-threaded anchor 100.

In the illustrative embodiment, the apertures 430*a* and 430*b* are similar to the apertures 410*a* and 410*b* discussed above except they have two longitudinal arcuate grooves or recesses 434*a* and 434*b* defined therein (only arcuate groove 434*a* is viewable in FIGS. 4E and 4F). The two arcuate grooves 434*a* and 434*b* are sized to slidingly accommodate side rails on the anchor, such as side rails 230*a* and 230*b* of the anchor 200 discussed above. The interaction between the side rails 230*a* and 230*b* with the arcuate grooves 434*a* and 434*b* may be used to guide the anchor 200 in a non-centered insertion location as discussed below.

In certain embodiments, the interaction of the arcuate grooves 434*a* and 434*b* with the corresponding side rails 230*a* and 230*b* and longitudinal shape or geometry of the non-threaded anchor also defines a portion of insertion trajectory for the non-threaded anchor. In other embodiments, the arcuate grooves 434*a* and 434*b* may be disposed about the apertures 430*a* and 430*b* in any desired configuration and may define any insertion trajectories as appropriate. In the example embodiment depicted in FIGS. 4D through 4F, the arcuate grooves 434*a* and 434*b* are defined in opposing sides around the center axis of the aperture. It should be noted that this configuration of arcuate groove 434*a* and 434*b* locations are merely an example, and the scope of this disclosure should not be limited thereto to the illustrative embodiments.

In certain embodiments, the interaction of the inwardly sloped engaging surfaces 432*a* and 432*b* with the longitudinal shape or geometry of the elongated body portion 204 of non-threaded anchor 200 defines an initial insertion trajectory for the non-threaded anchor. For purposes of this disclosure the "initial trajectory" is the path of movement of the elongated body portion 204 of an anchor 200 starting when the elongated body portion 204 is first introduced into the aperture (e.g. either aperture 430*a* or 430*b*) and ending when the head portion 202 of the anchor 200 first comes into contact with the engaging feature of the apertures 430*a*-430*b* (such as edges 436*a* and 436*b* and/or surfaces 432*a* and 432*b* forming a portion of the inside of the aperture).

Figure 4G:
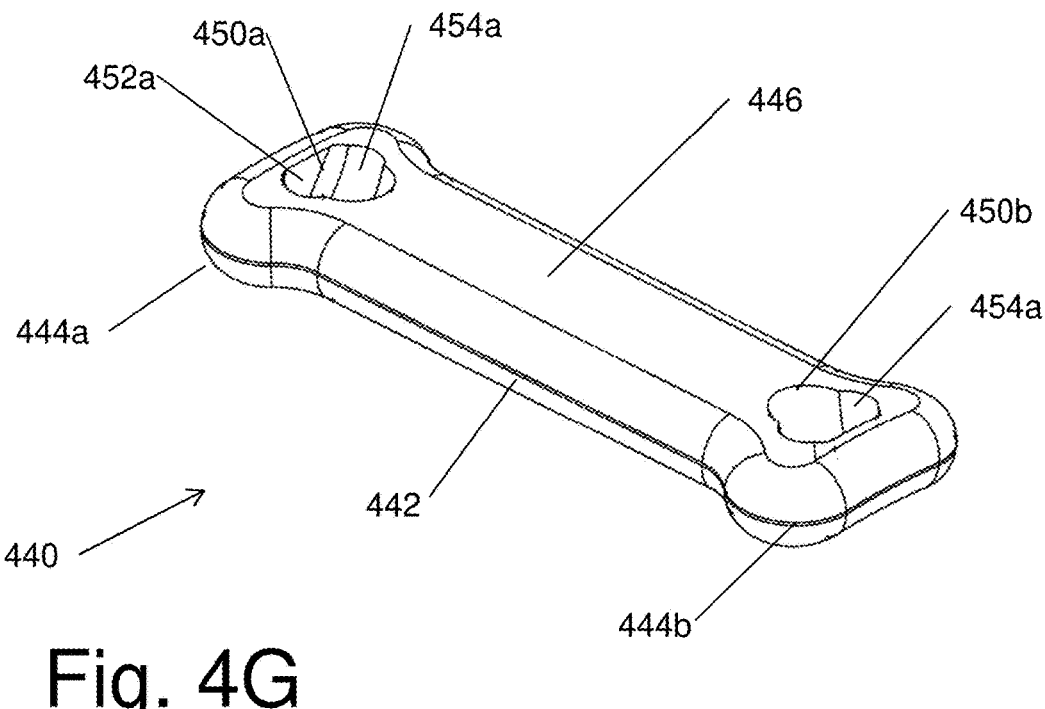
FIG. 4G is an isometric view of an alternative embodiment of a supra plate which can be used with different aspects of the present invention.
Figure 4H:
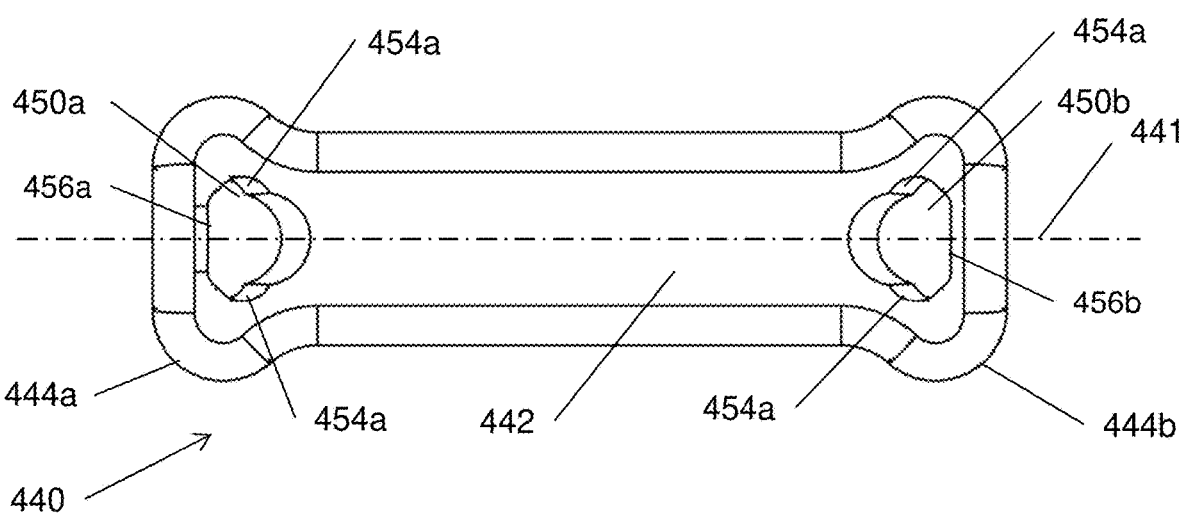
FIG. 4H is a top view of one embodiment of the implant of FIG. 4G.
Figure 4I:
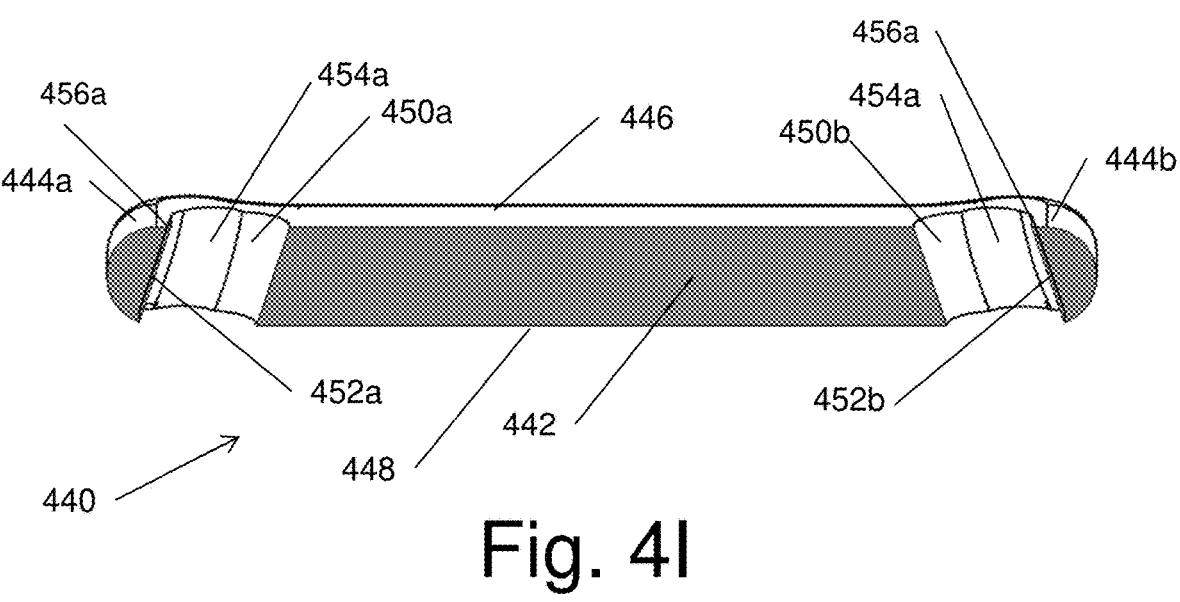
FIG. 4I is an isometric section view of one embodiment of the implant of FIG. 4G.

A Supra Plate for Distraction and for Receiving Anchors with Rails:

FIG. 4G is an isometric illustration of an alternative supra bone implant for use in methods involving distraction of two boney structures. FIG. 4H is a top view of the supra implant 440 and FIG. 4I is a sectional perspective view of the supra implant 440. For brevity and clarity, some of the description of those parts which are identical or similar to those described in connection with the first embodiment of the supra implant 440 illustrated above will not be repeated here. Reference should be made to the foregoing paragraphs with the following description to arrive at a complete understanding of this second embodiment of the supra implant.

In the illustrated embodiment of FIGS. 4G, 4H and 4I, the supra implant 440 has an elongated main body portion 442 with end portions 444a and 444b on each side of the main body portion. In certain embodiments, the main body portion 442 and the end portions 444a and 444b are all aligned along a longitudinal axis 441 (FIG. 4H). The supra implant 440 has a proximal surface 446 and a distal surface 448 (FIG. 4I) for engaging or for placement next to one or more boney structures.

In certain embodiments, the end portions 444a and 444b have apertures 450a and 450b defined therethrough for accepting a non-threaded anchor, such as anchor 200 described above. In certain embodiments, the apertures 450a and 450b are non-threaded and may have engagement features (such as edges 456a and 456b and/or curved or straight engaging surfaces 452a and 452b defined therein which are sized to receive and engage a surface of the non-threaded anchor 100).

In the illustrative embodiment, the apertures 450a and 450b are similar to the apertures 430a and 430b discussed above except they slope outward as opposed to the inward slope of the apertures 430a and 430b (compare FIG. 4F showing an inward slope for the apertures to FIG. 4I which shows an outward slope). Furthermore, the engaging features (such as edges 456a-456b and surfaces 452a and 452b are on the opposite side of the apertures 430a and 430b as illustrated in FIGS. 4F and 4I). Because the illustrative embodiment is designed to accept anchors with rails, there are two arcuate opposing grooves 454a and 454b in each aperture which are sized to slidingly accommodate rails, such as side rails 230a and 230b of the anchor 200 discussed above. The interaction between the side rails 230a and 230b with the arcuate grooves 454a and 454b may be used to guide the anchor 200 in a non-centered insertion location as discussed below.

In certain embodiments, the interaction of the arcuate grooves 454a and 454b with the corresponding side rails 230a and 230b and longitudinal shape or geometry of the non-threaded anchor also defines a portion of insertion trajectory for the non-threaded anchor. In other embodiments, the arcuate grooves 454a and 454b may be disposed about the apertures 450a and 450b in any desired configuration and may define any insertion trajectories as appropriate. In the example embodiment depicted in FIGS. 4G through 4I, the arcuate grooves 454a and 454b are defined in opposing sides around the center axis of the aperture. It should be noted that this configuration of arcuate groove 454a and 454b locations are merely an example, and the scope of this disclosure should not be limited thereto to the illustrative embodiments.

In certain embodiments, the interaction of the outwardly sloped engaging surfaces 452a and 452b with the longitudinal shape or geometry of the elongated body portion 204 of non-threaded anchor 200 defines an initial insertion trajectory for the non-threaded anchor. For purposes of this disclosure the "initial trajectory" is the path of movement of the elongated body portion 204 of an anchor 200 starting when the elongated body portion 204 is first introduced into the aperture (e.g. either aperture 450a or 450b) and ending when the head portion 202 of the anchor 200 first comes into contact with the engaging features (such as edges 456a-456b and/or surfaces 452a and 452b forming a portion of the inside of the aperture).

The implants disclosed herein, such as supra implants 400, 420, or 440 may be manufactured from any number of implant grade materials, including, but not limited to Titanium and Titanium Alloys, as well as Carbon Fiber Reinforced Polymer (CFRP) and shape memory alloys.

Methods of Use

Compression with Smooth Anchors:

FIGS. 5A through 5E demonstrate a method of using at least two anchors 100a and 100b with the supra implant, for instance, supra implant 400 to compress two boney structures 550a and 550b together. For purposes of this disclosure, a boney structure many be an entire human bone or a portion of a bone that has been fragmented or otherwise separated. FIGS. 5A through 5E are cross-sectional views of the implant 400, the boney structures 550a and 550b, and two anchors 100a and 100b showing different stages of interaction between these elements. Anchors 100a and 100b are similar to anchor 100 discussed above with the subscribe reference letters added to distinguish the anchors from one another. For brevity and clarity, a description of those parts which are identical or similar to those described in connection with the implant 400 or the anchor 100 will not be repeated here.

Figure 5A:
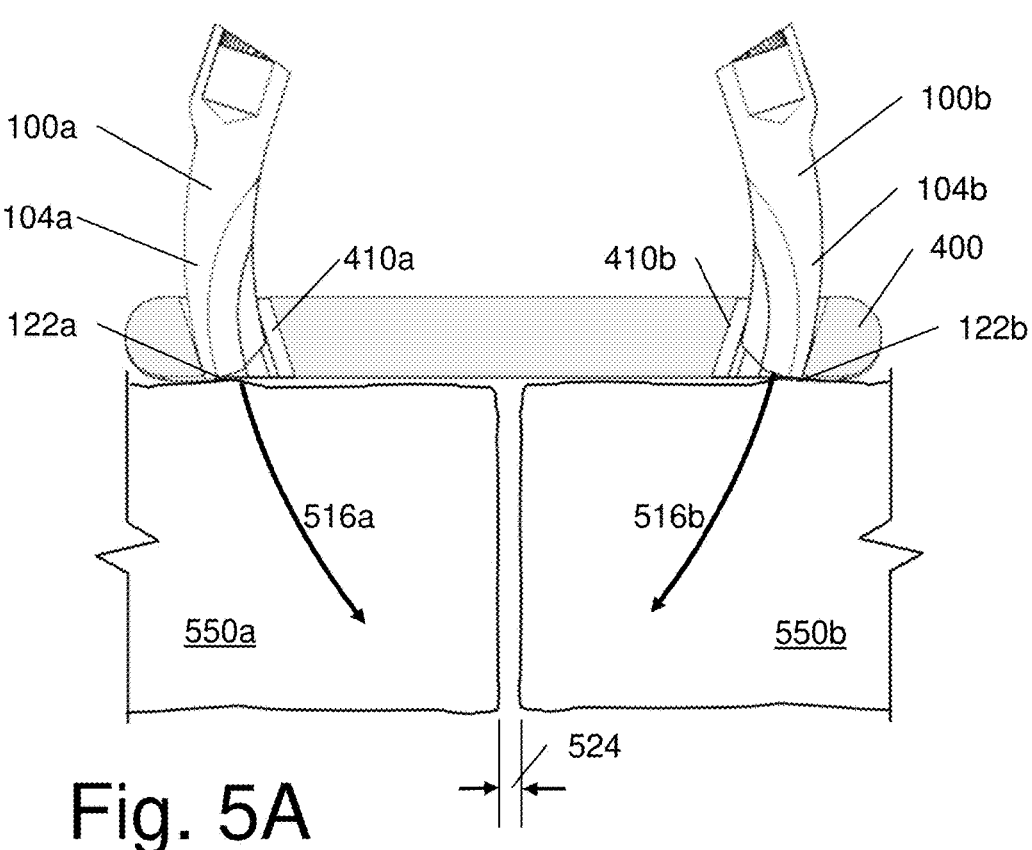
FIG. 5A is a sectional view of a supra plate positioned adjacent to two boney structures and two anchors before the anchors are deployed.

In FIG. 5A, the implant 400 is positioned adjacent to the boney structure 550a and the second boney structure 550b. For purposes of explaining the illustrated embodiment, a gap 524 (not drawn to scale) is illustrated between the boney structure 550a and the boney structure 550b. Additionally, for purposes of illustration, an initial trajectory of elongated body portion 104a of anchor 100a can be visualized as arrow 516a. Similarly, an initial trajectory of elongated body portion 104b of anchor 100b can be visualized as arrow 516b. In FIG. 5A, a distal end 122a of the non-threaded elongated body portion 104a is illustrated as having been introduced into the aperture 410a. Similarly, a distal end 122b of the non-threaded elongated body portion 104b is illustrated as having been introduced into the aperture 410b.

Figure 5B:
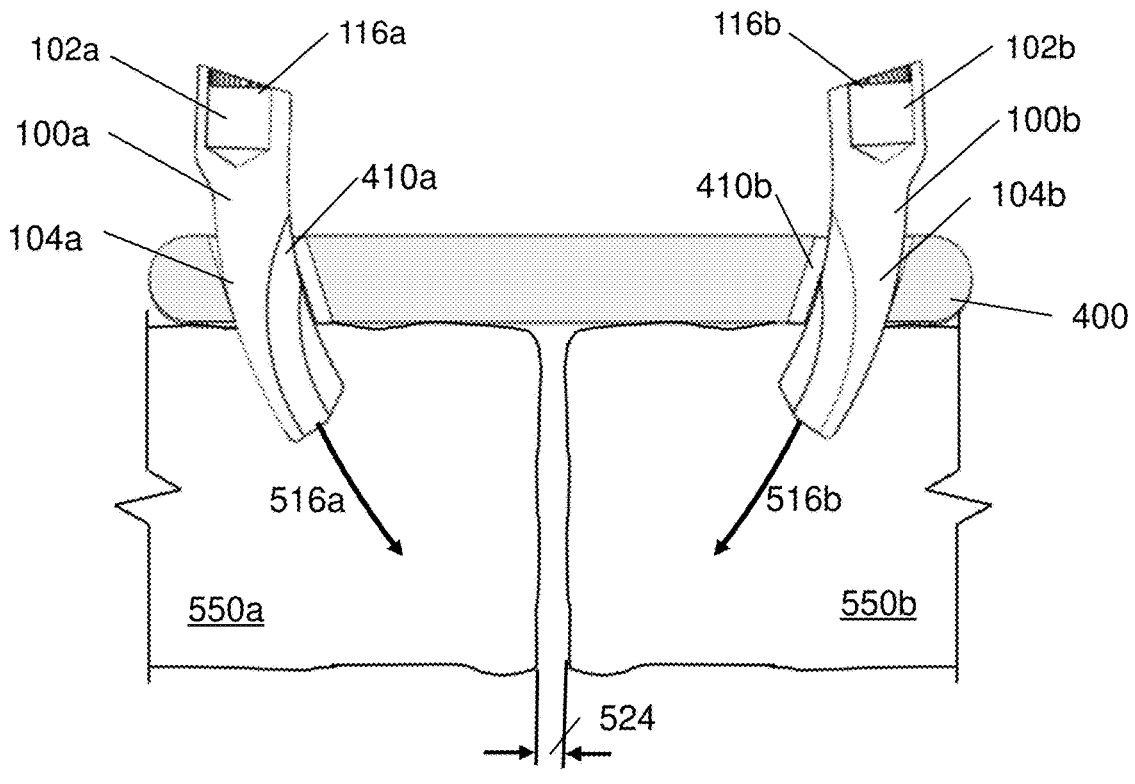
FIG. 5B is a sectional view of a supra plate positioned adjacent to two boney structures and two anchors during deployment of the anchors.

FIG. 5B illustrates the system and boney structures of FIG. 5A, but with the elongated body portions 104a and 104b driven partially into the boney structures 550a and 550b, respectively. In certain embodiments, a smooth non-torsional force may be applied onto the proximal end 116a of the head portion 102a to drive the elongated body portion 104a through the aperture 410a and into the boney structure 550a along the trajectory illustrated as arrow 516a. Additionally, a smooth non-torsional force may be applied onto the proximal end 116b of the head portion 102b to drive the elongated body portion 104b through the aperture 410b and into the boney structure 550b along the trajectory illustrated as arrow 516b. In certain embodiments this non-torsional force may be a "smooth" non-torsional force as opposed to a series of impact forces. In yet other embodiments, an impact force may be applied to drive the elongated body portions 104a and 104b into the boney structures 550a and 550b, respectively.

Figure 5C:
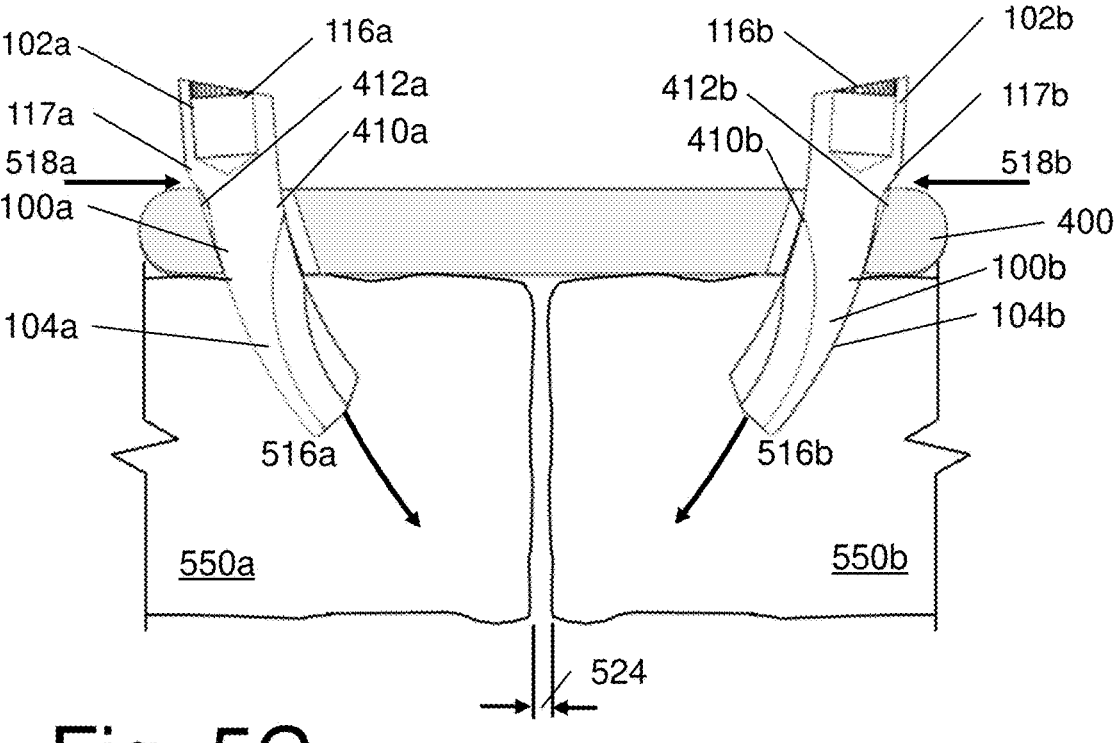
FIG. 5C is a sectional view of a supra plate positioned adjacent to two boney structures and two anchors during deployment of the anchors where the interaction of the heads of the anchors and the plate are beginning to cause a transverse movement.

Similarly, FIG. 5C illustrates the system and boney structures of FIG. 5B, but with the elongated body portions 104a and 104b driven farther into the boney structures 550a and 550b, respectively. As can be seen in FIG. 50, the elongated body portions 104a and 104b have been almost completely driven through the apertures 410a and 410b, respectively and each elongated body portion 104a and 104b are still following their respective initial trajectories as represented by arrows 516a and 516b.

FIG. 5C also illustrates the situation where the non-torsional force continues to be applied onto the proximal end 116a as the transition surface 117a of head portion 102a begins to interact with the engaging features (e.g., the edge 414a and/or the surface 412a of the aperture 410a). The interaction between the engaging feature of the aperture 410a and the transition surface 117a of the head portion 102a forces the head to in a direction that is generally transverse to the center axis 106 of the anchor 100a (see FIG. 1B above). The transition surface 117a allows for a smooth transition and kinematic transverse movement. The direction of this transverse movement is represented by the arrow 518a. The transverse movement of the head portion 102a also causes movement of the elongated body portion 104a. Because the boney structure 550a is now attached to the elongated body portion 104a, the boney structure 550a is also forced to move in the transverse direction represented by arrow 518a. Thus, causing the boney structure 550a to move closer to the boney structure 550b.

Simultaneously, a second non-torsional force continues to be applied onto the proximal end 116b as the transition surface 117b of head portion 102b begins to interact with the engaging feature of the of the aperture 410b (e.g. the surface 412b and/or the edge 414b). The interaction between the aperture 410b and the transition surface 117b of the head portion 102b forces the head to move in a direction that is generally transverse to the center axis 106 of the anchor 100a (see FIG. 1B above). The direction of this transverse movement is represented by the arrow 518b which is in a direction that is opposite from the direction represented by arrow 518a discussed above. The transverse movement of the head portion 102b also causes movement of the elongated body portion 104b. Because the boney structure 550b is now attached to the elongated body portion 104b, the boney structure 550b is also forced to move in the transverse direction represented by arrow 518b. Thus, causing the boney structure 550b to move closer to the boney structure 550b. The gap 524 narrows as the head portions 102a and 102b approach their respective apertures 410a and 410b.

Figure 5D:
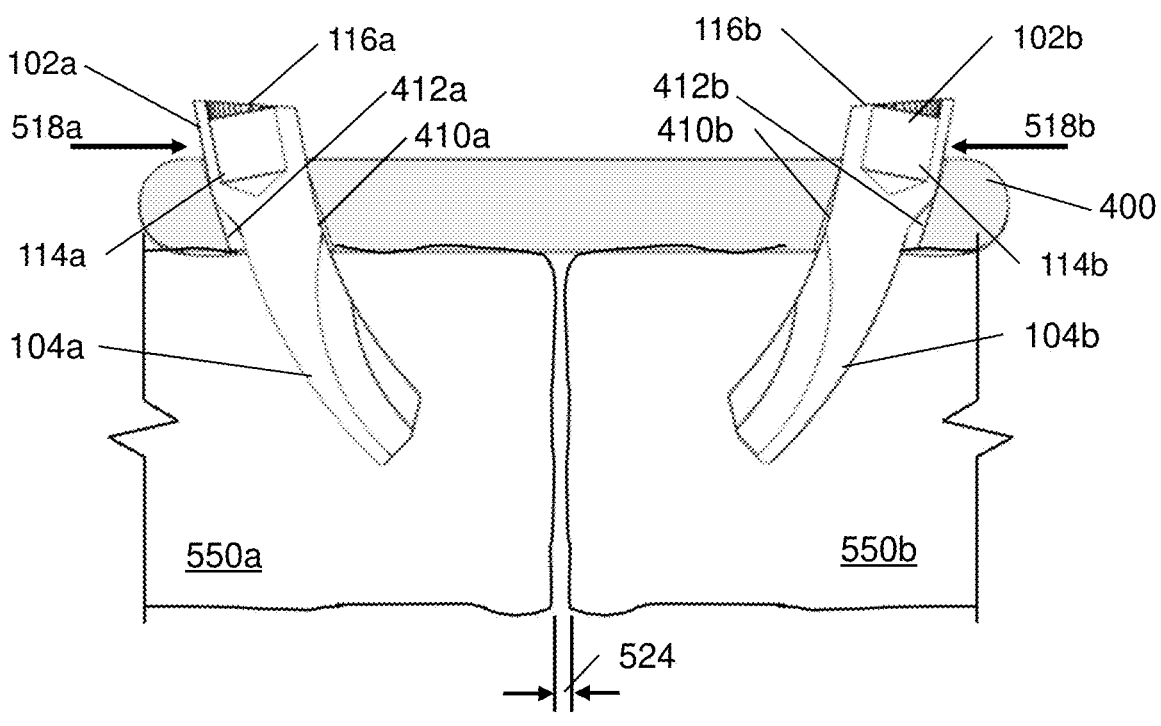
FIG. 5D is a sectional view of a supra plate positioned adjacent to two boney structures and two anchors during deployment of the anchors where the interaction of the heads of the anchors and the plate are causing additional transverse movement.

FIG. 5D illustrates the situation where the non-torsional force continues to be applied onto the proximal end 116a of the head portion 102a as the first head portion is pushed farther into the first aperture 410a. The interaction between the inwardly sloped surface 412a of the aperture 410a and the offset portion 114a of the head portion 102a forces the head portion to keep moving in the transverse direction as indicated by arrow 518a. As discussed above, the transverse movement of the head portion 102a also causes additional transverse movement of the elongated body portion 104a, which causes the boney structure 550a to also move in the direction of arrow 518a towards the boney structure 550b.

Simultaneously, a second non-torsional force continues to be applied onto the proximal end 116b of the head portion 102b as the head portion is pushed farther into the first aperture 410a. The interaction between the inwardly sloped surface 412b of the aperture 410b and the offset portion 114b of the head portion 102b forces the head portion to keep moving in the transverse direction as indicated by arrow 518b. As discussed above, the transverse movement of the head portion 102b also causes additional transverse movement of the elongated body portion 104a, which causes the boney structure 550b to also move in the direction of arrow 518a and towards the boney structure 550a. The relative movement between the boney structure 550a and the boney structure 550b causes the gap 524 to significantly narrow.

Figure 5E:
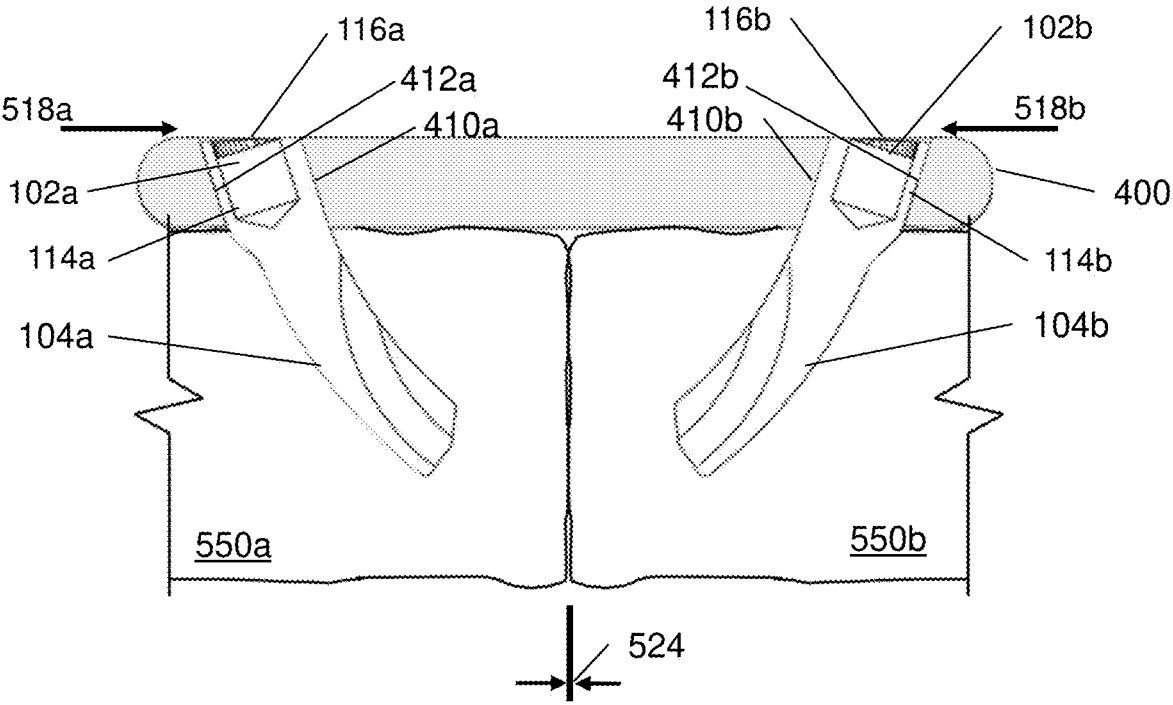
FIG. 5E is a sectional view of a supra plate positioned adjacent to two boney structures and two anchors fully deployed to cause compression of the boney structures against each other.

FIG. 5E illustrates the situation where the head portion 102a has been pushed completely into the aperture 410a. As explained above, the interaction between the engagement feature (e.g., inwardly sloped surface 412a) of the aperture 410a and the offset portion 114a of the head portion 102a has forced the head portion to continue to move transversely in the direction of the arrow 518a. The transverse movement of the head portion 102a also cause transverse movement of the elongated body portion 104a, which caused the boney structure 550a to compress against the boney structure 550b.

Similarly, the head portion 102b has been pushed completely into the aperture 410b. As explained above, the interaction between the engagement feature (e.g., inwardly sloped surface 412b) of the aperture 410b and the offset portion 114b of the head portion 102b has forced the head portion to move transversely in the direction of the arrow 518b. The transverse movement of the head portion 102b also caused the transverse movement of the elongated body portion 104b, which caused the boney structure 550b to compress against the boney structure 550a. The gap 524 is now closed as the boney structure 550a is pressed against the boney structure 550b. In certain embodiments, the magnitude or height of the offset of the anchor head portions 102a-102b and the angle of slope of the engagement surfaces 412a and 412b may determine the amount of compression achieved.

Compression with Railed Anchors:

FIGS. 6A through 6F demonstrate a method of using at least two anchors 200a and 200b with the supra implant, for instance, supra implant 420 to compress two boney structures 650a and 650b together. Specifically, FIGS. 6A through 6E are cross-sectional views of the implant 420, the boney structures 650a and 650b, and two anchors 200a and 200b showing different stages of interaction between these elements. The method discussed in reference to FIGS. 6A through 6F is similar to the method discussed in reference to FIGS. 5A through 5E above except for the use of two anchors 200a and 200b which have side rails and the use of a plate 420 which has opposing groves to accommodate the side rails as discussed in reference to FIGS. 4D through 4F. Anchors 200a and 200b are similar to anchor 200 discussed above with the subscribe reference letters added to distinguish the anchors from one another. For brevity and clarity, certain descriptions of steps and embodiments which are identical or similar to those described in connection with FIGS. 5A through 5E will not be repeated here.

Figure 6A:
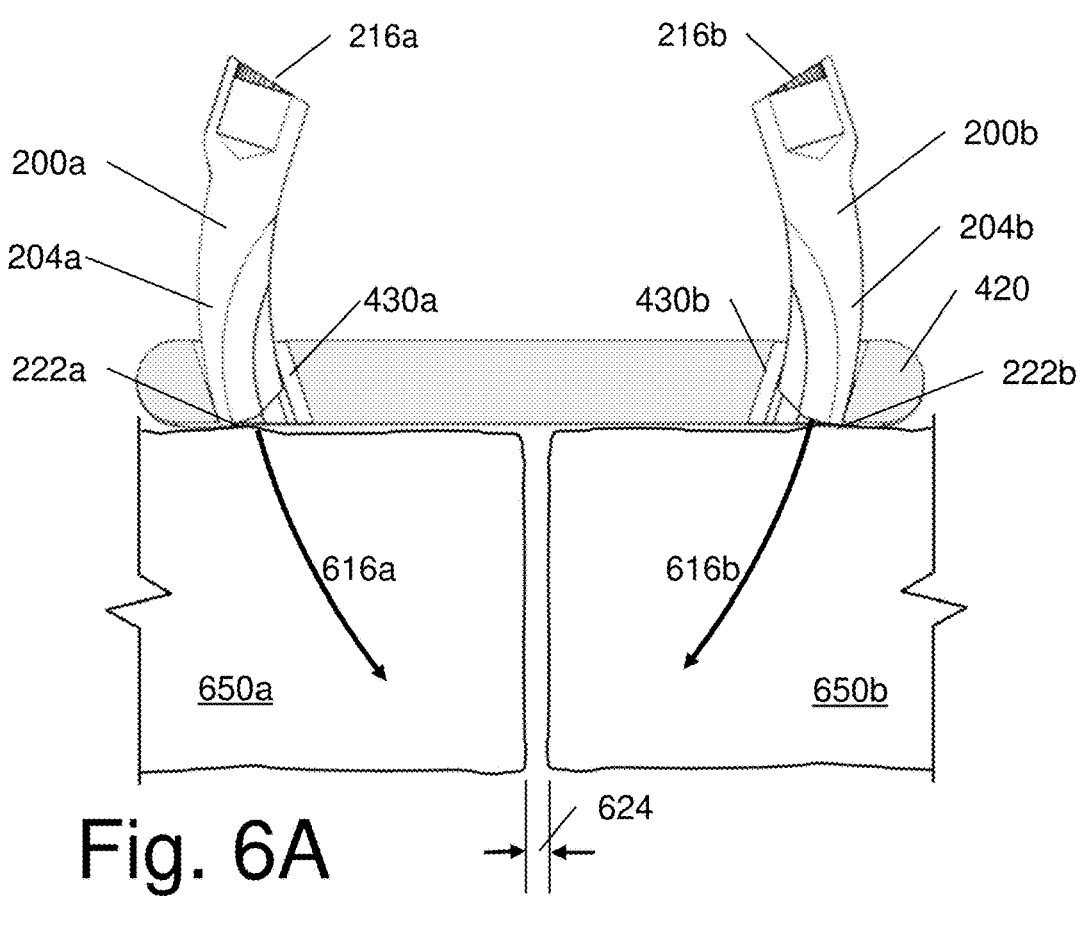
FIG. 6A is a midline sectional view of an alternative supra plate positioned adjacent to two boney structures and two alternative anchors before the anchors are deployed.
Figure 6B:
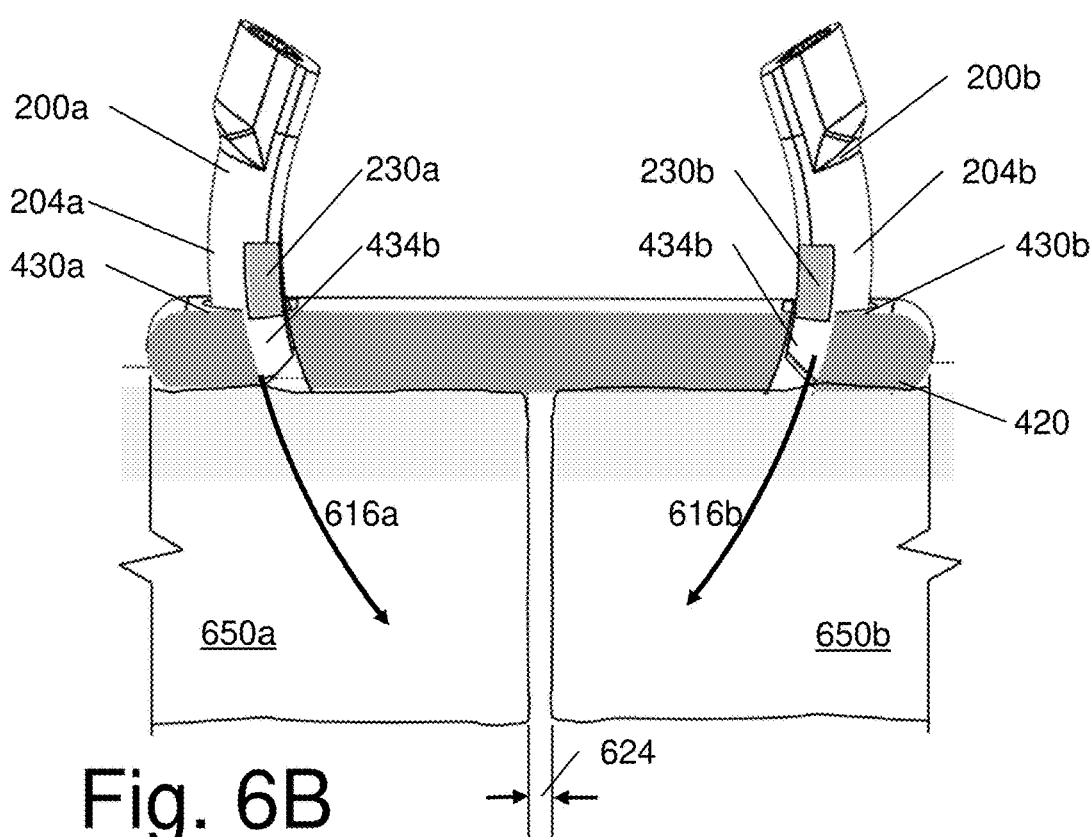
FIG. 6B is an offset sectional view of the alternative supra plate and two alternative anchors of FIG. 6A.
Figure 6C:
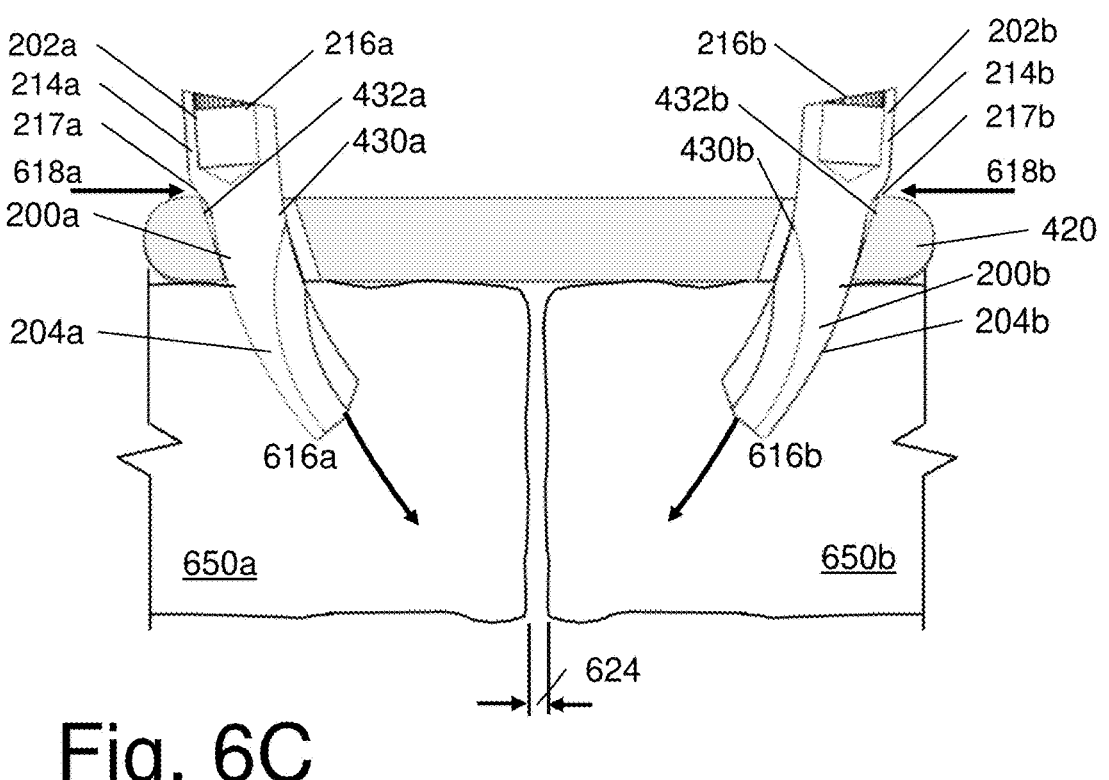
FIG. 6C is a midline sectional view of a supra plate and two anchors of FIG. 6A during deployment of the anchors.
Figure 6D:
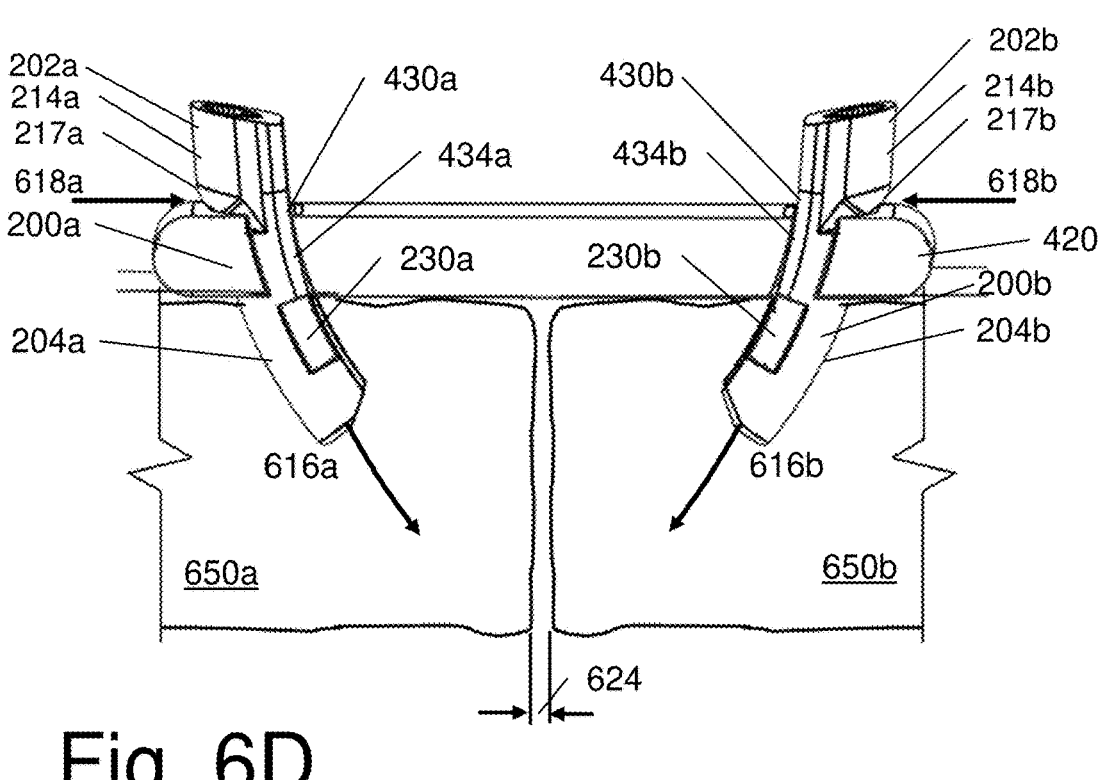
FIG. 6D is an offset sectional view of the alternative supra plate and two alternative anchors of FIG. 6C.

FIGS. 6A, 6C, and 6D is a series of cross-sectional illustrations of the implant 420, the boney structures 650a and 650b, and the anchors 200a and 200b cut at the mid-plane of the implant 420 to show the progression of the anchors 200a-200b into the boney structures 650a-650b. In contrast, FIGS. 6B, 6D, and 6F are cross-sectional illustrations of the implant 420, the boney structures 650a and 650b, and the anchors 200a-200b cut to one side of the mid-plane to show the interaction of the side rails 230a-230b projecting from the anchors 200a-200b with that of the arcuate grooves 434a-434b defined within the apertures 430a and 430b (see FIGS. 4D-4F) as the anchors 200a-200b progress into the boney structures 650a-650b.

In FIG. 6A, the implant 420 is positioned adjacent to the boney structure 650a and the second boney structure 650b. For purposes of explaining the illustrated embodiment, a gap 624 (not drawn to scale) is illustrated between the boney structure 650a and the boney structure 650b. Additionally, for purposes of illustration, an initial trajectory of elongated body portion 204a of anchor 200a can be visualized as arrow 616a. Similarly, an initial trajectory of elongated body portion 204b of anchor 200b can be visualized as arrow 616b. In FIG. 6A, a distal end 222a of the non-threaded elongated body portion 204*a* is illustrated as having been introduced into the aperture 430*a*. Similarly, a distal end 222*b* of the non-threaded elongated body portion 204*b* is illustrated as having been introduced into the aperture 430*b*.

FIG. 6B illustrates the relative position of the elements in FIG. 6A, but the sectional view of FIG. 6B is cut offset from the mid-plane of the implant to show the relationship of the side rails 230*a*-230*b* with that of the arcuate grooves 434*b* defined within the apertures 430*a*-430*b*. FIG. 6D is actually cut at the arcuate grooves 434*b* and shows the side rails 230*a*-230*b* as they are about to enter their corresponding arcuate grooves. Once the body portions 204*a*-204*b* are pushed through the apertures 430*a*-430*b*, the arcuate grooves 434*a*-434*b* interacting with the rails 230*a* and 230*b* guide and define the placement of the anchors 200*a*-200*b* along the initial trajectories as illustrated by the arrows 616*a* and 616*b*.

In certain embodiments, a smooth non-torsional force may be applied onto the proximal end 216*a* of the head portion 202*a* to drive the elongated body portion 204*a* through the aperture 430*a* and into the boney structure 650*a* along the trajectory illustrated as arrow 616*a*. Additionally, a smooth non-torsional force may be applied onto the proximal end 216*b* of the head portion 202*b* to drive the elongated body portion 204*b* through the aperture 430*b* and into the boney structure 650*b* along the trajectory illustrated as arrow 616*b*. In certain embodiments this non-torsional force may be a "smooth" non-torsional force as opposed to a series of impact forces. In yet other embodiments, an impact force may be applied to drive the elongated body portions 204*a* and 204*b* into the boney structures 650*a* and 650*b*, respectively.

FIG. 6C illustrates the system and boney structures of FIG. 6A, but the elongated body portions 204*a* and 204*b* of the anchors have been driven partially into the corresponding boney structures 650*a* and 650*b*. As can be seen in FIG. 6C, the elongated body portions 204*a* and 204*b* have been driven such that the heads 202*a* and 202*b* are just reaching the edge of their corresponding apertures 430*a* and 430*b*. The elongated body portion 204*a* and 204*b* are still following their corresponding initial trajectories as represented by arrows 616*a* and 616*b*.

FIG. 6C also illustrates the situation where as the non-torsional force continues to be applied onto the proximal end 216*a*, the transition surface 217*a* of head portion 202*a* begins to interact with the engaging feature of the aperture 430*a* (i.e. edge 436*a* or surface 432*a* of the aperture 430*a*). The interaction between the engaging feature of the aperture 430*a* and the transition surface 217*a* of the head portion 202*a* forces the head to move in a direction that is generally transverse to a center axis of the anchor 200*a* (see the discussion reference FIG. 1B above). The transition surface 217*a* allows for a smooth transition and kinematic transverse movement. The general direction of this transverse movement is represented by the arrow 618*a*.

The transverse movement of the head portion 202*a* will cause movement of the elongated body portion 204*a*. Because the boney structure 650*a* is now attached to the elongated body portion 204*a*, the boney structure 650*a* will also be forced to move in the transverse direction as represented by arrow 618*a*. Thus, this interaction is beginning to cause the boney structure 650*a* to move closer to the boney structure 650*b*.

Simultaneously, a second non-torsional force continues to be applied onto the proximal end 216*b* as the transition surface 217*b* of head portion 202*b* begins to interact with the engaging feature (edge 436*b* and/or the surface 432*b* of the aperture 430*b*). The interaction between the aperture 430*b* and the transition surface 217*b* of the head portion 202*b* will force the head to move in a direction that is generally transverse to a center axis of the anchor 200*b* (see FIG. 1B above). The direction of this transverse movement is represented by the arrow 618*b* which is in a direction that is generally opposite from the direction represented by arrow 618*a* discussed above. The transverse movement of the head portion 202*b* will also cause movement of the elongated body portion 204*b*. Because the boney structure 650*b* is attached to the elongated body portion 204*b*, the boney structure 650*b* will also be forced to move in the transverse direction represented by arrow 618*b*. Thus, causing the boney structure 650*b* to move closer to the boney structure 650*b* which causes the gap 624 to narrow.

FIG. 6D illustrates the relative position of the elements in FIG. 6C, but the sectional view of FIG. 6D is cut offset from the mid-plane of the supra implant 420 to show the side rails 230*a*-230*b* and the arcuate grooves 434*b* as the body portions 204*a*-240*b* of the anchors 200*a*-200*b* are pushed further through the apertures 430*a*-430*b*. In FIG. 6D, the side rails 230*a*-230*b* have been pushed through the arcuate grooves 434*b*. Pushing the side rails 230*a*-230*b* past the arcuate grooves 434*a*-434*b* may allow for an additional transverse shift of the body portions 204*a* of the anchor 200*a* in the direction of the arrow 618*a* because the side rails 230*a*-230*b* are no longer constrained by the arcuate grooves 434*a*-434*b*.

When the non-torsional forces continue to be applied onto the proximal ends 216*a*-216*b* of the head portions 202*a*-202*b*, the head portions are pushed farther into their corresponding apertures 430*a*-430*b*. The interaction between the engagement feature (the edge 436*a* and/or the inwardly sloped surface 432*a* of the aperture 430*a*) and the offset portion 214*a* of the head portion 202*a* forces the head portion to move in the transverse direction as indicated by arrow 618*a*. As discussed above, the transverse movement of the head portion 202*a* causes transverse movement of the elongated body portion 204*a*, which causes the boney structure 650*a* to also move in the direction of arrow 618*a* towards the boney structure 650*b*.

Additionally, the interaction between the engagement feature (the edge 436*b* and/or the inwardly sloped surface 432*b*) of the aperture 430*b* and the offset portion 214*b* of the head portion 202*b* forces the head portion to keep moving in the transverse direction as indicated by arrow 618*b*. As discussed above, the transverse movement of the head portion 202*b* also causes transverse movement of the elongated body portion 204*a*, which causes the boney structure 650*b* to also move in the direction of arrow 618*a* and towards the boney structure 650*a*. The relative movement between the boney structure 650*a* and the boney structure 650*b* causes the gap 624 to close.

Figure 6E:
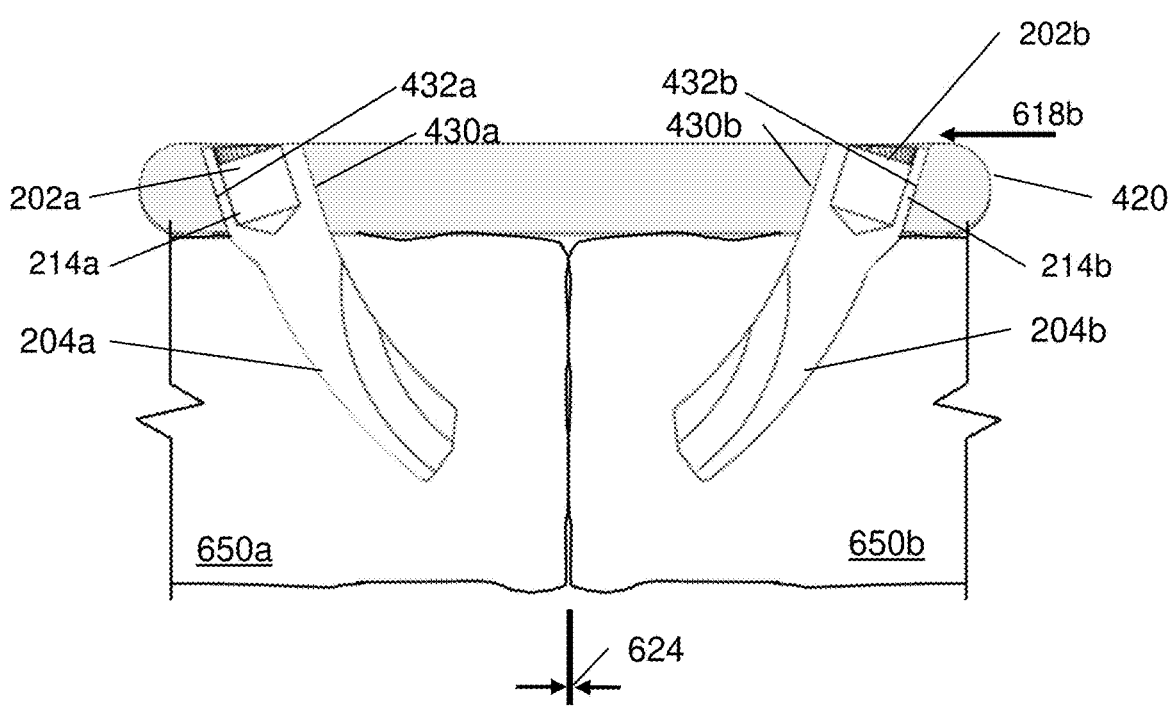
FIG. 6E is a midline sectional view of a supra plate and two anchors of FIG. 6A fully deployed to cause compression of the boney structures against each other.
Figure 6F:
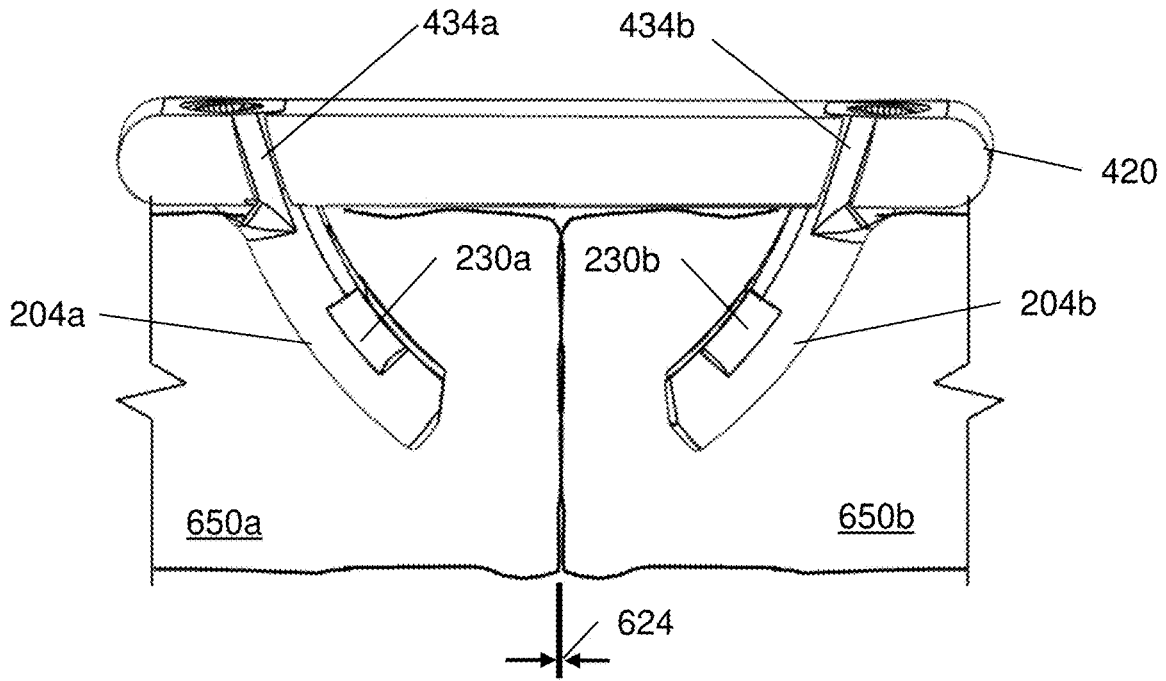
FIG. 6F is an offset sectional view of a supra plate and two anchors of FIG. 6E.

FIG. 6E illustrates the situation where the head portion 202*a* has been pushed completely into the aperture 430*a*. Similarly, the head portion 202*b* has been pushed completely into the aperture 430*b*. Because of the transverse movement of the heads 202*a* and 202*b* towards each other (and carrying the body portions 204*a* and 204*b* towards each other), the gap 624 is now closed as the boney structure 650*a* is pressed against the boney structure 650*b*. In certain embodiments, the magnitude or height of the offset of the anchor head portions 202*a*-202*b* and the angle of slope of the engagement surfaces 432*a* and 432*b* may determine the amount of compression achieved.

FIG. 6F illustrates the relative position of the elements in FIG. 6E, but the sectional view of FIG. 6F is cut offset from the mid-plane to show the relationship of the rails 230a and 230b to the arcuate grooves 434b as the anchors 200a-200b are seated within the supra implant 420.

Compression with Anchors Having Steps or Stepped Protrusions:

The methods discussed in reference to FIGS. 5A through 6F can also be used with two anchors having steps or stepped protrusions, such as anchor 300. As discussed above, anchor 300 has steps or stepped protrusions 340 on the opposing side of the offset portion 314 of the heads 302 (see FIG. 3A-D). The steps or stepped surfaces can increase the amount of transverse movement and be used to guide the anchor. For brevity and clarity, certain descriptions of steps and embodiments which are identical or similar to those described in connection with FIGS. 5A through 6F will not be repeated here.

As explained above, the implant 400 (or a similar implant with enlarged apertures) may be positioned adjacent to two boney structures. The distal ends 322 of the body portion 304 of anchors 300 may be introduced into their respective apertures defined in the implant.

In certain embodiments, a smooth non-torsional force may be applied onto the proximal end 316 of the head portion 302 of the anchors 300 to drive the elongated body portions 304 through their apertures and into the boney structures along the trajectory similar to the trajectories discussed above. An engaging surface defined within the aperture interacts with the steps or stepped surfaces to help guide and define the placement of the anchor 300 along the initial trajectory.

As the non-torsional force continues to be applied onto the proximal ends 316 of the anchors 300, the transition surface 317 of each head portion 302 begins to interact with the corresponding engaging surface of the apertures defined within the implant. As explained above, the interaction between the engaging surfaces the transition surface 317 of the head portion 302 forces the head portion to move in a direction that is generally transverse to a center axis of the anchor 300 (see the discussion reference FIG. 1B above). The transition surface 317 allows for a smooth transition and kinematic transverse movement. The general direction of this transverse movement of the body portions 304 towards each other as discussed above.

As the head portions 302 reach their respective apertures, the steps or stepped portion of the anchor will have been pushed through the opposing side of the aperture. Pushing the steps or stepped protrusions past the apertures will allow a transverse shift of the body portions 304 of the anchor 300 as discussed above.

The lateral movement will continue until the head portions 302 have been pushed completely into their respective apertures. Because of the transverse movement of the heads 302 towards each other (and carrying the body portions 304 of the anchors 300 towards each other), any gap between the boney structures would now be closed as the boney structure are pressed against each other. In certain embodiments, the magnitude or height of the offset of the anchor head portions 302, the height of the step or stepped protrusion, and the angle of slope of the engagement surfaces of the aperture implant may determine the amount of lateral movement and compression achieved.

A Method of Distracting with Railed Anchors:

FIGS. 7A through 7F demonstrate a method of using at least two anchors 200a and 200b with the supra implant, for instance, supra implant 440 to distract two boney structures 750a and 750b apart from each other. The methods for distraction discussed in reference to FIGS. 7A through 7F are similar to the methods for compression discussed in reference to FIGS. 5A through 6F above except for the use of a different orientation of the plate apertures and a different orientation of the anchors.

In the illustrative compression methods described above, the trajectory of the anchors converge to the longitudinal center of the implant and the "offset" portion of the anchors face away from the longitudinal center of the implant as illustrated by FIGS. 5A and 6A. Additionally, the plate apertures used in the compression methods "point inward" and the engaging features (e.g. surfaces 412a, 412b, 432a, or 432b and/or edges 414a, 414b, 436a, or 436b) are on the "outward" side of the aperture with respect to the longitudinal center of the supra implant.

Figure 7A:
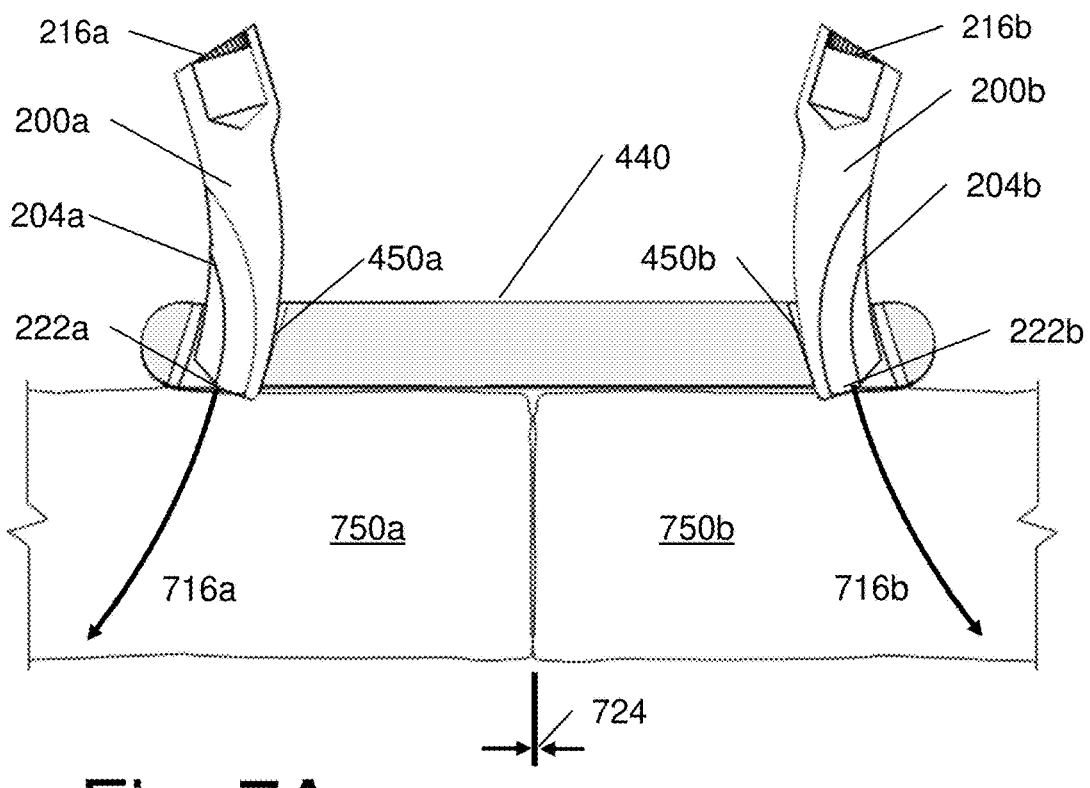
FIG. 7A is a midline sectional view of an alternative supra plate positioned adjacent to two boney structures and two alternative anchors before the anchors are deployed to illustrate a method of distraction.

In contrast, in the disclosed distraction methods described herein, the trajectory of the anchors diverge away from the longitudinal center of the implant and the "offset" portion of the anchors face inward toward the longitudinal center of the implant as illustrated by FIG. 7A. Additionally, the plate apertures used in the distraction methods "point outward" and the engaging surfaces are on the "inward" side of the aperture with respect to the longitudinal center of the implant. Compare, for instance, the compression methods of FIG. 5A and FIG. 6A with the distraction methods of FIG. 7A. For brevity and clarity, certain descriptions of steps and embodiments which are identical or similar to those described in connection with FIGS. 5A through 6F above will not be repeated here.

Figure 7B:
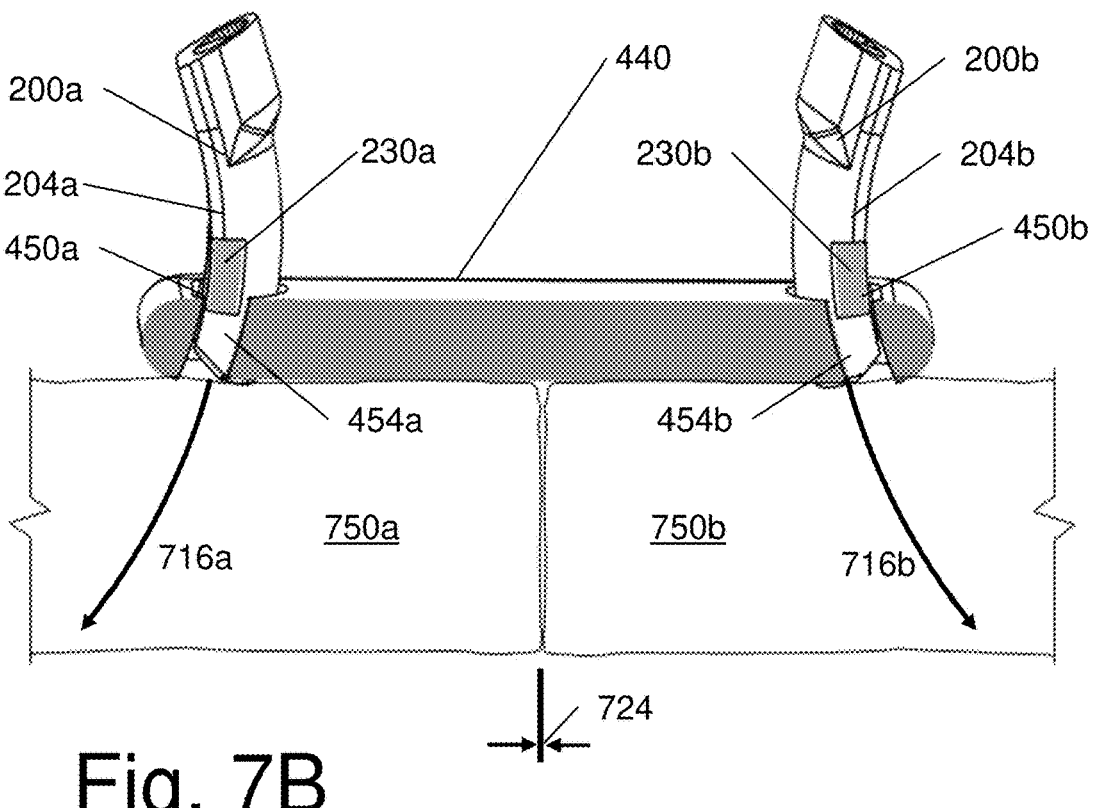
FIG. 7B is an offset sectional view of the alternative supra plate and two alternative anchors of FIG. 7A.
Figure 7C:
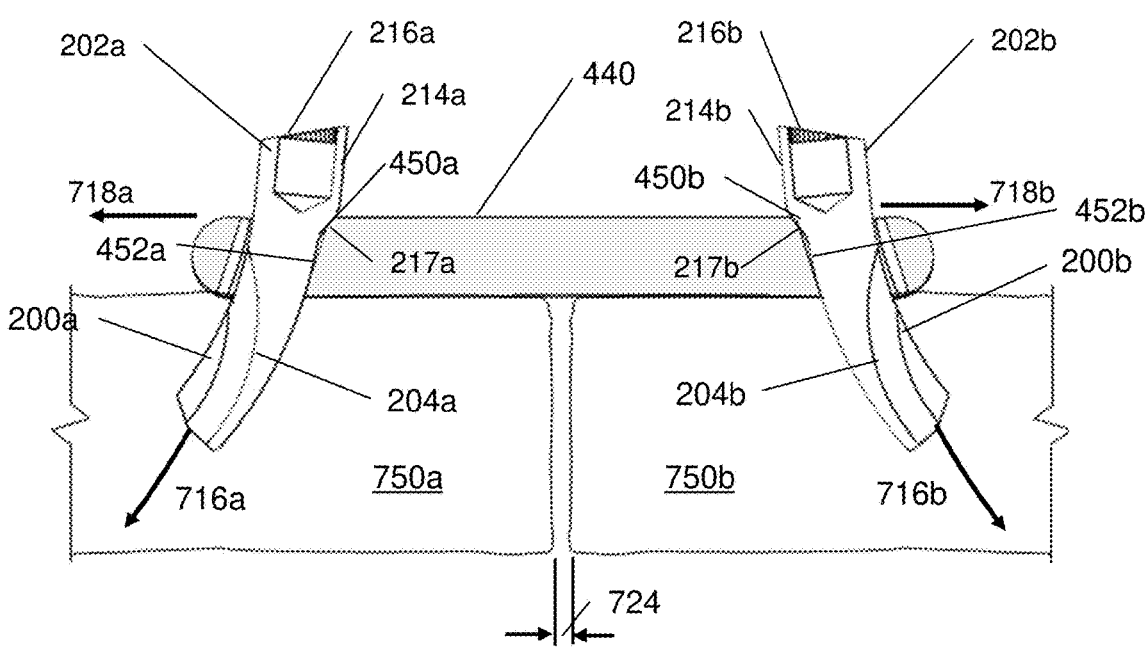
FIG. 7C is a midline sectional view of a supra plate and two anchors of FIG. 7A during deployment of the anchors.
Figure 7D:
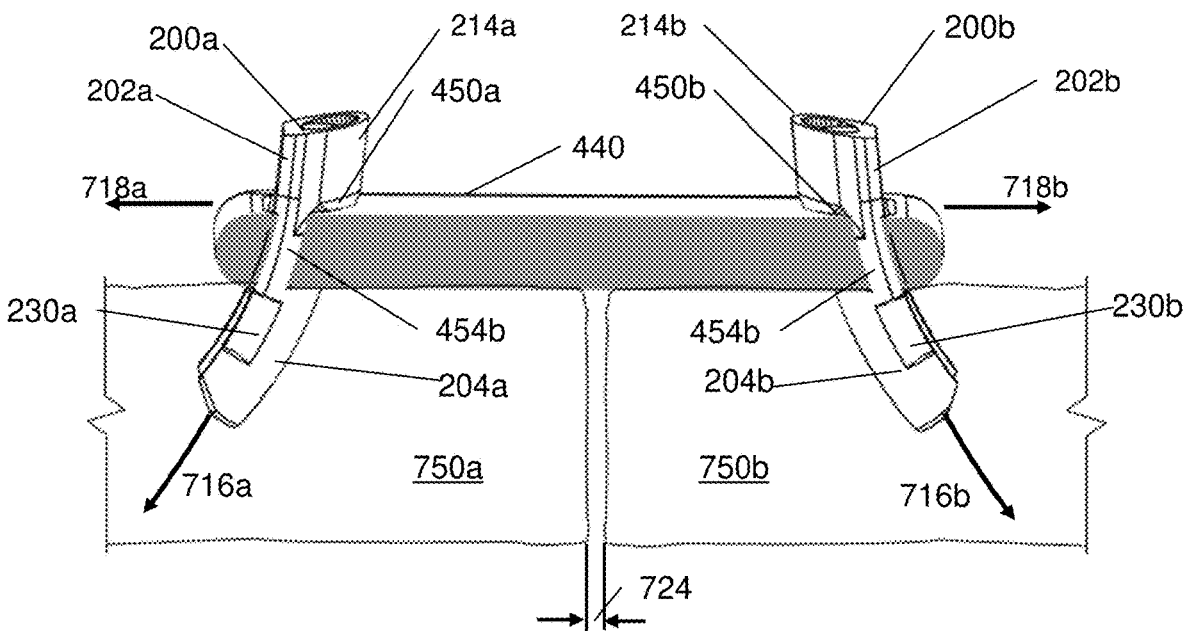
FIG. 7D is an offset sectional view of the alternative supra plate and two alternative anchors of FIG. 7C.

FIGS. 7A, 7C, and 7D is a series of cross-sectional illustrations of the supra implant 440, the boney structures 750a and 750b, and the anchors 200a and 200b cut at the mid-plane of the implant 440 to show the progression of the anchors 200a-200b into the boney structures 750a-750b. In contrast, FIGS. 7B, 7D, and 7F are cross-sectional illustrations of the implant 440, the boney structures 750a and 750b, and the anchors 200a-200b cut to one side of the mid-plane to show the interaction of the side rails 230a-230b projecting from the anchors 200a-200b with that of the arcuate grooves 454a-454b defined within the apertures 450a and 450b (see FIGS. 4D-4F) as the anchors 200a-200b progress into the boney structures 750a-750b. (While any of the anchors 100, 200, and 300 discussed above may also be used with distraction methods, for illustrative purposes only, exemplary anchors 200a and 200b will be discussed in connection with the distraction methods referenced in FIGS. 7A-7F).

In FIG. 7A, the implant 440 is positioned adjacent to the boney structure 750a and the second boney structure 750b. For purposes of explaining the illustrated embodiment, a small gap or fracture 724 (not drawn to scale) is illustrated between the boney structure 750a and the boney structure 750b. Additionally, for purposes of illustration, an initial trajectory of elongated body portion 204a of anchor 200a can be visualized as arrow 716a. Similarly, an initial trajectory of elongated body portion 204b of anchor 200b can be visualized as arrow 716b. In FIG. 7A, a distal end 222a of the non-threaded elongated body portion 204a is illustrated as having been introduced into the aperture 450a. Similarly, a distal end 222b of the non-threaded elongated body portion 204b is illustrated as having been introduced into the aperture 450b.

FIG. 7B illustrates the relative position of the elements in FIG. 7A, but the sectional view of FIG. 7B is cut offset from the mid-plane of the implant to show the relationship of the side rails 230a-230b with that of the arcuate grooves 454b defined within the apertures 450a-430b. FIG. 7D is actually cut at the arcuate grooves 454b and shows the side rails 230a-230b as they are about to enter their corresponding arcuate grooves. Once the body portions 204a-204b are pushed through the apertures 450a-450b, the arcuate grooves 454a-454b interacting with the rails 230a and 230b guide and define the placement of the anchors 200a-200b along the initial trajectories as illustrated by the arrows 716a and 716b.

In certain embodiments, a smooth non-torsional force may be applied onto the proximal end 216a of the head portion 202a to drive the elongated body portion 204a through the aperture 450a and into the boney structure 750a along the trajectory illustrated as arrow 716a. Additionally, a smooth non-torsional force may be applied onto the proximal end 216b of the head portion 202b to drive the elongated body portion 204b through the aperture 450b and into the boney structure 750b along the trajectory illustrated as arrow 716b. In certain embodiments this non-torsional force may be a "smooth" non-torsional force as opposed to a series of impact forces. In yet other embodiments, an impact force may be applied to drive the elongated body portions 204a and 204b into the boney structures 750a and 750b, respectively.

FIG. 7C illustrates the system and boney structures of FIG. 7A, but the elongated body portions 204a and 204b of the anchors have been driven partially into the corresponding boney structures 750a and 750b. As can be seen in FIG. 7C, the elongated body portions 204a and 204b have been driven such that the heads 202a and 202b are just reaching the edge of their corresponding apertures 450a and 450b. The elongated body portion 204a and 204b are still following their corresponding initial trajectories as represented by arrows 716a and 716b.

FIG. 7C also illustrates the situation where as the non-torsional force continues to be applied onto the proximal end 216a, the transition surface 217a of head portion 202a begins to interact with the engaging feature (such as edge 456a and/or surface 452a) of the aperture 450a. The interaction between the engaging feature of the aperture 450a and the transition surface 217a of the head portion 202a forces the head to move in a direction that is generally transverse to a center axis of the anchor 200a (see the discussion reference FIG. 1B above). The transition surface 217a allows for a smooth transition and kinematic transverse movement. The general direction of this transverse movement is represented by the arrow 718a.

The transverse movement of the head portion 202a will cause movement of the elongated body portion 204a. Because the boney structure 750a is now attached to the elongated body portion 204a, the boney structure 750a will also be forced to move in the transverse direction as represented by arrow 718a. Thus, this interaction is beginning to cause the boney structure 750a to move away from the boney structure 750b.

Simultaneously, a second non-torsional force continues to be applied onto the proximal end 216b as the transition surface 217b of head portion 202b begins to interact with the engaging feature (such as the edge 456b and/or the surface 452b) of the aperture 450b. The interaction between the aperture 450b and the transition surface 217b of the head portion 202b will force the head to move in a direction that is generally transverse to a center axis of the anchor 200b (see FIG. 1B above). The direction of this transverse movement is represented by the arrow 718b which is in a direction that is generally opposite from the direction represented by arrow 718a discussed above. The transverse movement of the head portion 202b will also cause movement of the elongated body portion 204b. Because the boney structure 750b is attached to the elongated body portion 204b, the boney structure 750b will also be forced to move in the transverse direction represented by arrow 718b. Thus, causing the boney structure 750b to move away or distract from the boney structure 750b which causes the gap or fracture 724 to widen.

FIG. 7D illustrates the relative position of the elements in FIG. 7C, but the sectional view of FIG. 7D is cut offset from the mid-plane of the supra implant 440 to show the side rails 230a-230b and the arcuate grooves 454b as the body portions 204a-240b of the anchors 200a-200b are pushed further through the apertures 450a-430b. In FIG. 7D, the side rails 230a-230b have been pushed through the arcuate grooves 454b. Pushing the side rails 230a-230b past the arcuate grooves 454a-434b may allow for an additional a transverse shift of the body portions 204a of the anchor 200a in the direction of the arrow 718a because the side rails 230a-230b are no longer constrained by the arcuate grooves 454a-434b.

When the non-torsional forces continue to be applied onto the proximal ends 216a-216b of the head portions 202a-202b, the head portions are pushed farther into their corresponding apertures 450a-430b. The interaction between the engagement feature of the aperture 450a and the offset portion 214a of the head portion 202a forces the head portion to move in the transverse direction as indicated by arrow 718a. As discussed above, the transverse movement of the head portion 202a causes transverse movement of the elongated body portion 204a, which causes the boney structure 750a to also move in the direction of arrow 718a towards the boney structure 750b.

Additionally, the interaction between the engagement feature (the engagement edge 456a and/or the inwardly sloped surface 452b) of the aperture 450b and the offset portion 214b of the head portion 202b forces the head portion to keep moving in the transverse direction as indicated by arrow 718b. As discussed above, the transverse movement of the head portion 202b also causes transverse movement of the elongated body portion 204a, which causes the boney structure 750b to also move in the direction of arrow 718a and towards the boney structure 750a. The relative movement between the boney structure 750a and the boney structure 750b causes the gap 724 to close.

Figure 7E:
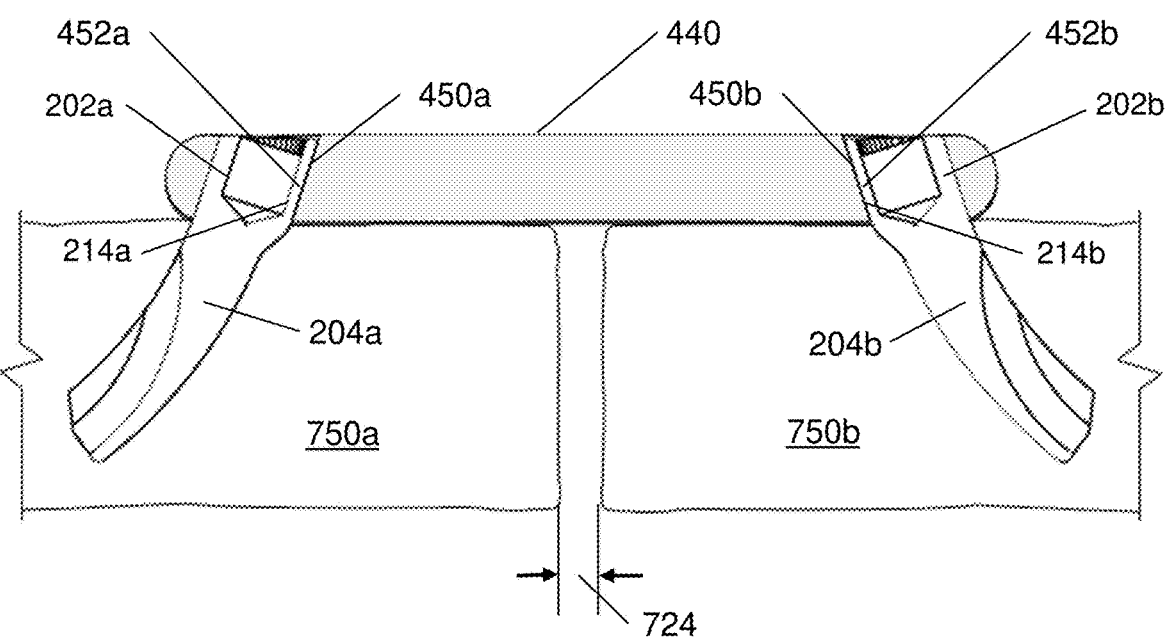
FIG. 7E is a midline sectional view of a supra plate and two anchors of FIG. 7A fully deployed to cause distraction of the boney structures against each other.
Figure 7F:
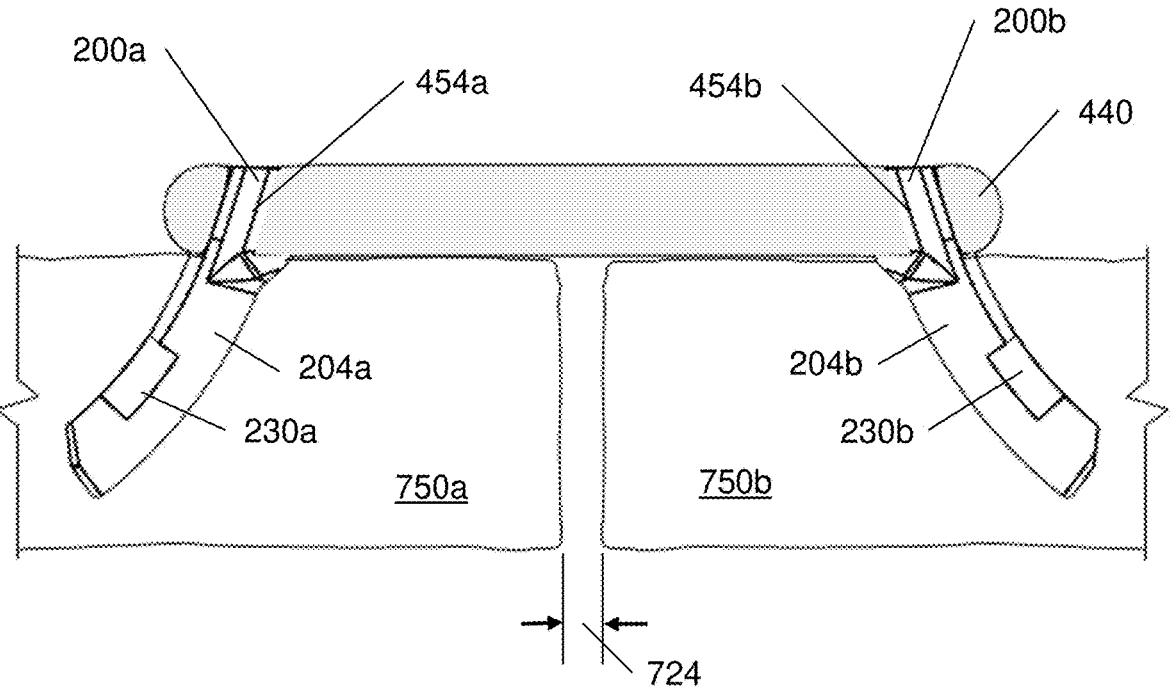
FIG. 7F is an offset sectional view of a supra plate and two anchors of FIG. 7E.

FIG. 7E illustrates the situation where the head portion 202a has been pushed completely into the aperture 450a. Similarly, the head portion 202b has been pushed completely into the aperture 450b. Because of the transverse movement of the heads 202a and 202b towards each other (and carrying the body portions 204a and 204b towards each other), the gap 724 has now been widen to a predetermined amount as the boney structure 750a is distracted from the boney structure 750b. The magnitude or height of the distraction depends on height of the offset of the anchor head portions 202a-202b and the angle of slope of the engagement surfaces 452a and 452b may determine the amount of compression achieved.

FIG. 7F illustrates the relative position of the elements in FIG. 7E, but the sectional view of FIG. 7F is cut offset from the mid-plane to show the relationship of the rails 230a and 230b to the arcuate grooves 454b as the anchors 200a-200b are seated within the supra implant 440.

In certain embodiments, the oversized geometry of the offset portion 214 causes a light press fit between the anchor head portion 214 and an aperture of an implant. Thus, in some embodiments, the offset portion 214 may be an oversized geometric volume which contacts a surface of the aperture of an implant. These are cylindrical surfaces which will largely be concentric in the final position, and in the offset portion 214 they may have an incrementally larger radius than the underside of the surface in the aperture resulting in being wedged together in the final position-which assists in preventing the anchor from "backing out" of the respective aperture. In yet other embodiments, other anti-back methods and techniques may also be employed, such as blocker plates, retaining rings, and locking screws. Method of Distracting with Anchors Having Steps or Stepped Protrusions:

The methods discussed in reference to FIGS. 7A through 7F can also be used with two anchors having steps or stepped protrusions, such as anchor 300. As discussed above, anchor 300 has steps or stepped protrusions 340 on the opposing side of the offset portion 314 of the heads 302 (see FIG. 3A-D). The steps or stepped surfaces can increase the amount of transverse movement and be used to guide the anchor. For brevity and clarity, certain descriptions of steps and embodiments which are identical or similar to those described in connection with FIGS. 7A through 7F will not be repeated here.

As explained above, the implant 440 (or a similar implant with enlarged apertures) may be positioned adjacent to two boney structures. The distal ends 322 of the body portion 304 of anchors 300 may be introduced into their respective apertures defined in the implant.

In certain embodiments, a smooth non-torsional force may be applied onto the proximal end 316 of the head portion 302 of the anchors 300 to drive the elongated body portions 304 through their apertures and into the boney structures along the trajectory similar to the trajectories discussed above. An engaging surface defined within the aperture interacts with the steps or stepped surfaces to help guide and define the placement of the anchor 300 along the initial trajectory.

As the non-torsional force continues to be applied onto the proximal ends 316 of the anchors 300, the transition surface 317 of each head portion 302 begins to interact with the corresponding engaging surface of the apertures defined within the implant. As explained above, the interaction between the engaging surfaces the transition surface 317 of the head portion 302 forces the head portion to move in a direction that is generally transverse to a center axis of the anchor 300 (see the discussion reference FIG. 1B above). The transition surface 317 allows for a smooth transition and kinematic transverse movement. The general direction of this transverse movement of the body portions 304 towards each other as discussed above in reference to FIG. 7C.

As the head portions 302 reach their respective apertures, the steps or stepped portion of the anchor will have been pushed through the opposing side of the aperture. Pushing the steps or stepped protrusions past the apertures may allow an additional transverse shift of the body portions 304 of the anchor 300 because the steps are no longer constrained by the aperture.

The lateral movement will continue until the head portions 302 have been pushed completely into their respective apertures. Because of the transverse movement of the heads 302 towards each other (and carrying the body portions 304 of the anchors 300 towards each other), any gap between the boney structures would now be closed as the boney structure are pressed against each other. The magnitude or height of the offset of the anchor head portions 302, the height of the step or stepped protrusion, and the angle of slope of the engagement surfaces of the aperture implant may determine the amount of lateral movement and distraction achieved.

In certain embodiments, the oversized geometry of the offset portion of the anchor heads (i.e., the offset portions 114, 214, and 314 described above) causes a light press fit between the anchor head portion and the corresponding aperture of an implant. In some embodiments, the offset portion may be an oversized geometric volume which contacts a surface of the aperture of an implant. These may be cylindrical surfaces which will largely be concentric in the final position, and in the offset portion they may have an incrementally larger radius than the underside of the surface in the aperture resulting in being wedged together in the final position-which assists in preventing the anchor from "backing out" of the respective aperture. In yet other embodiments, other anti-back methods and techniques may also be employed, such as blocker plates, retaining rings, and locking screws.

Inserter Embodiments

Figure 9A:
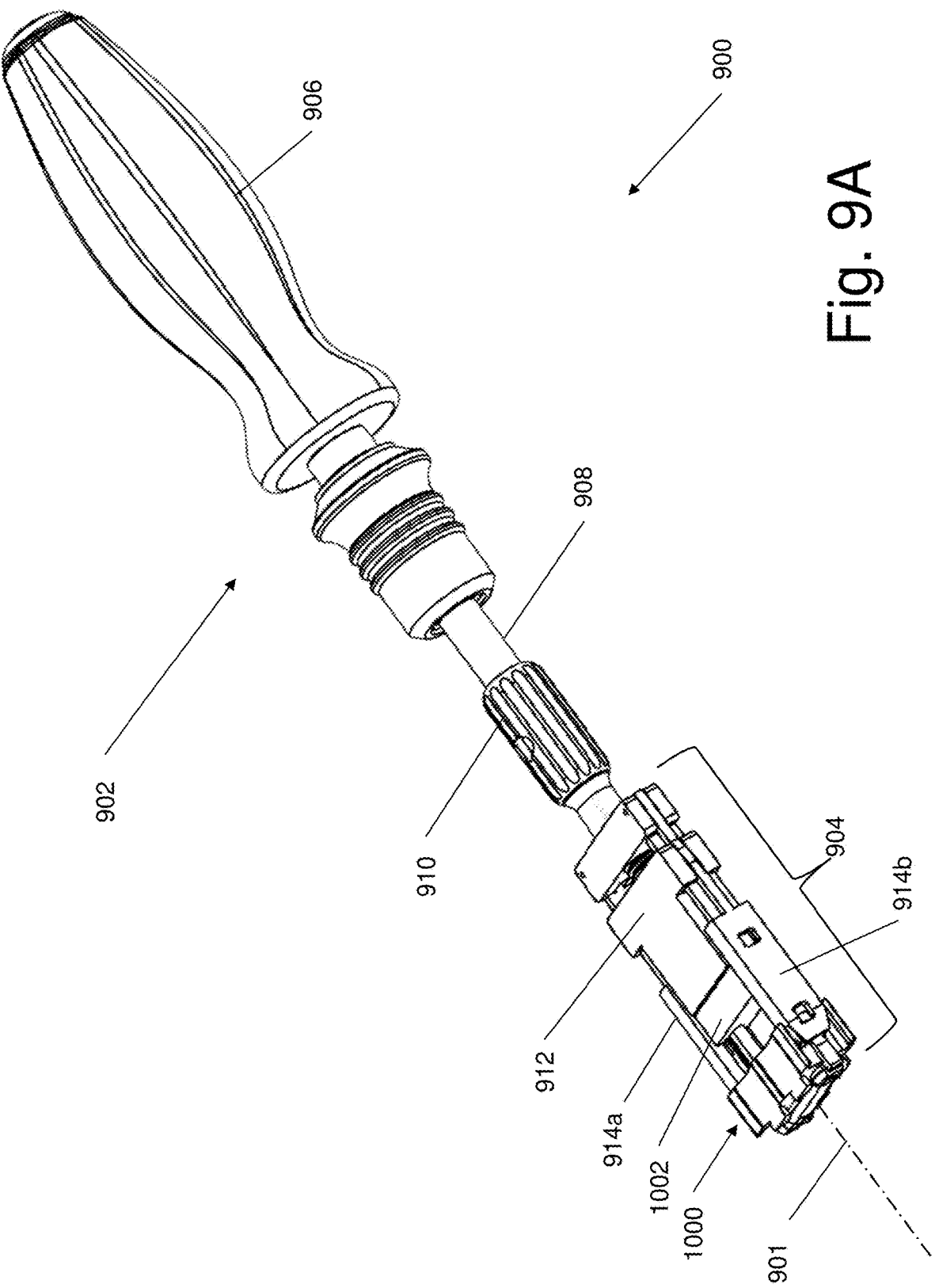
FIG. 9A is a perspective view of one aspect of an implant insertion system which can be used in one or more aspects of the present invention.
Figure 9B:
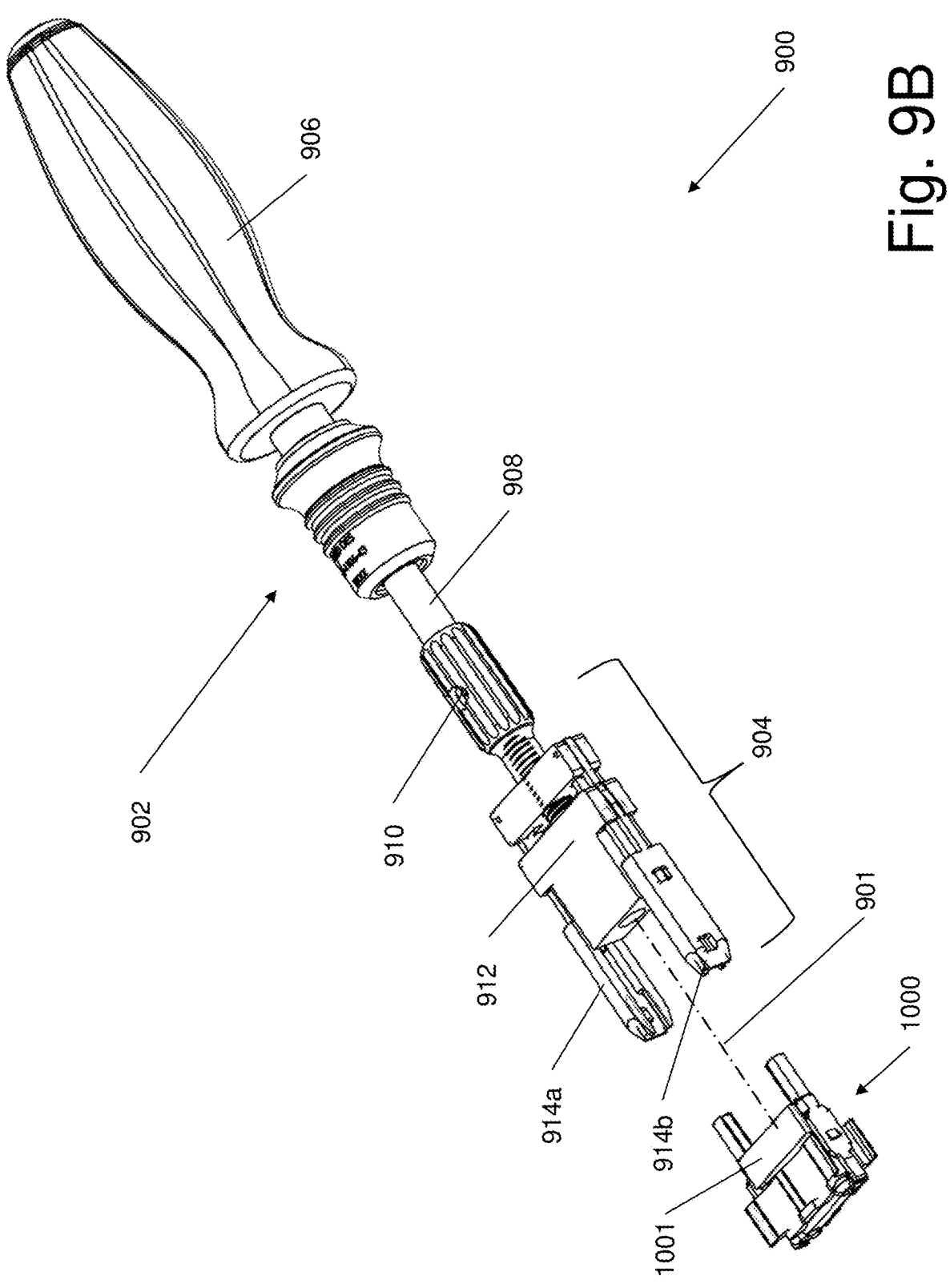
FIG. 9B is an exploded perspective view of the implant insertion system of FIG. 9A showing an implant cassette detached from the implant inserter system.

Turning now to FIG. 9A, there is presented a perspective view of an implant insertion system 900. In certain embodiments, the implant insertion system 900 comprises an inserter tool 902 and an implant cassette 1000. FIG. 9B is a perspective view of the implant insertion system 900 with the implant cassette 1000 decoupled from the inserter tool 902.

In certain embodiments, a handle 906 or another torque inducing mechanism is positioned at the proximal end of the inserter tool. The handle 906 is coupled to a proximal end of a longitudinal shaft or actuating rod 908. In certain embodiments, the actuating rod 908 passes through a fixed or non-rotating collar 910 and has a distal end that is rotatably coupled to an implant deployment mechanism 904. In certain embodiments, the handle 906 is designed to impart a torque on the actuating rod 908 when a user turns the handle 906. The fixed collar or non-rotating collar 910 allows the user to provide stability and counter-torque when the handle 906 is turned during insertion and deployment of the anchors. The use of the term "fixed collar" or "non-rotating" collar in this disclosure means that the user will hold the collar stationary with respect to the turning motion imparted on the handle 906. The actuating rod 908, the handle 906, the fixed collar 910 may be positioned concentrically along a longitudinal axis 901 of the inserter tool 902.

In certain embodiments, the implant deployment mechanism 904 comprises a translating element or actuator 912 which may be used to impart a linear force on a force transmission sub-assembly or actuator 1001 of the implant cassette 1000 when a torque is introduced on the actuating rod 908. In certain embodiments, the implant deployment mechanism 904 is releasably coupled to the implant cassette 1000 via side arms 914a and 914b which retain the implant cassette 1000 during deployment of the anchors.

In the embodiment illustrated in FIGS. 9A and 9B, the actuator 1001 is coupled to the implant cassette 1000 and may be part of the cassette 1000.

Figure 9C:
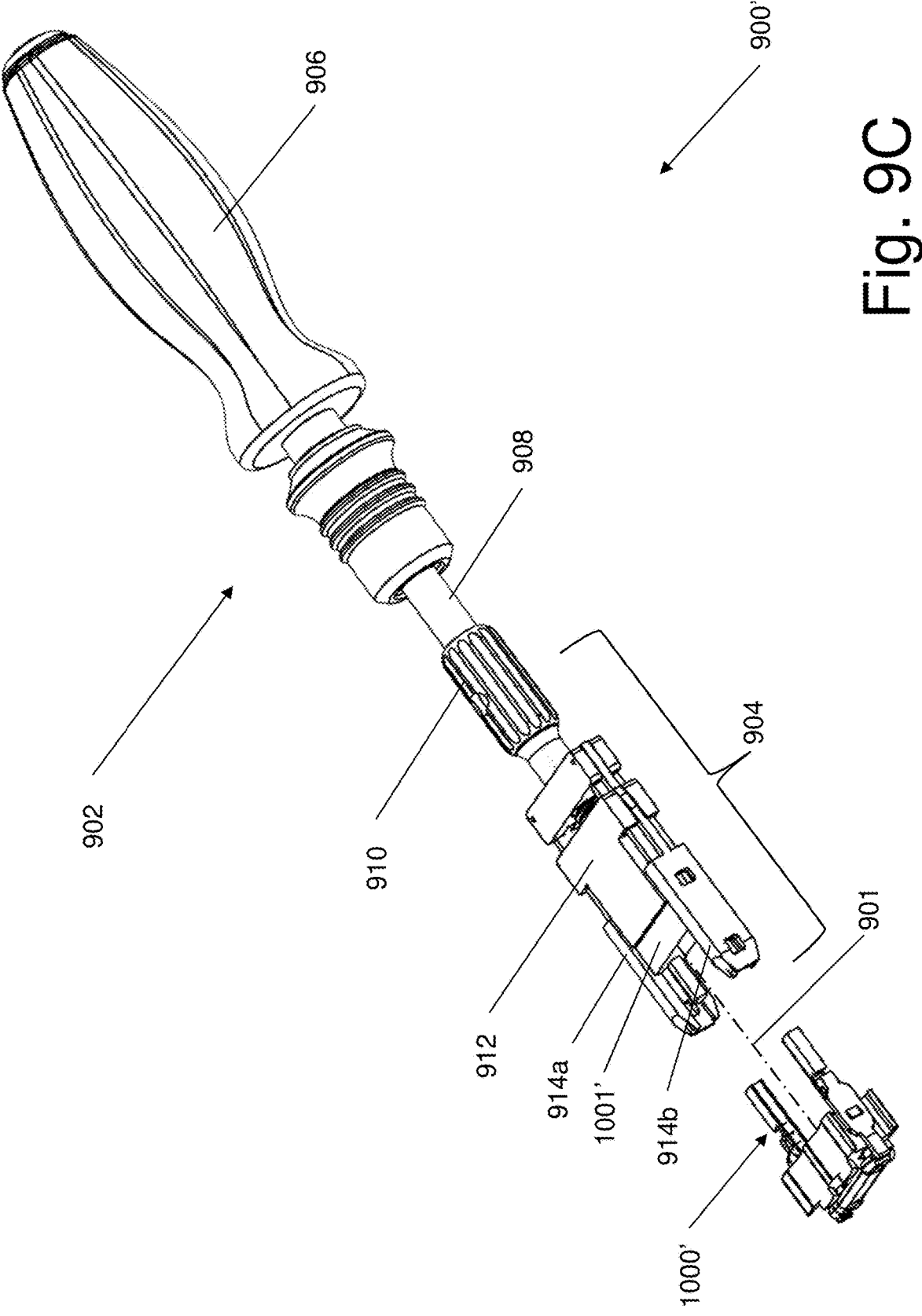
FIG. 9C is an exploded perspective view of the implant insertion system of FIG. 9A showing an alternative implant cassette detached from the implant inserter system.

FIG. 9C is an exploded perspective view of an alternative implant insertion system 900' showing an alternative implant cassette 1000' which can be used with the implant insertion system 900' of FIG. 9C. The implant insertion system 900' is similar to the implant insertion system 900 except that the actuator 1001 is coupled to the translating element 912 of the inserter and, consequently, is part of implant insertion tool 902—not part of the implant cassette 1000'. For brevity and clarity, a description of those components which are identical or similar to those described in connection with the implant insertion system 900 in FIGS.

9A and 9B will not be repeated here. Reference should be made to the discussion of the implant insertion system 900 to arrive at a complete understanding of the implant insertion system 900'.

In certain embodiments, the implant cassettes 1000 and 1000' are designed for a single use packed in a sterile container. In this manner, the surgical staff will not need to manipulate the plate or anchors. All that is required is coupling the cassette 1000 or 1000' to the implant insertion tool 902, implanting the implant, and then deploying the anchors. In such a situation, minimizing the sterile packaging may be desirable, in which case, the implant cassette 1000' may have advantages over the implant cassette 1000. Furthermore, because the components of the implant cassettes 1000 and 1000' are designed to be discarded after use (except for the implant and anchors), minimizing the components (as in the embodiment of implant cassette 1000') may have economic benefits for the distributing company.

Figure 9D:
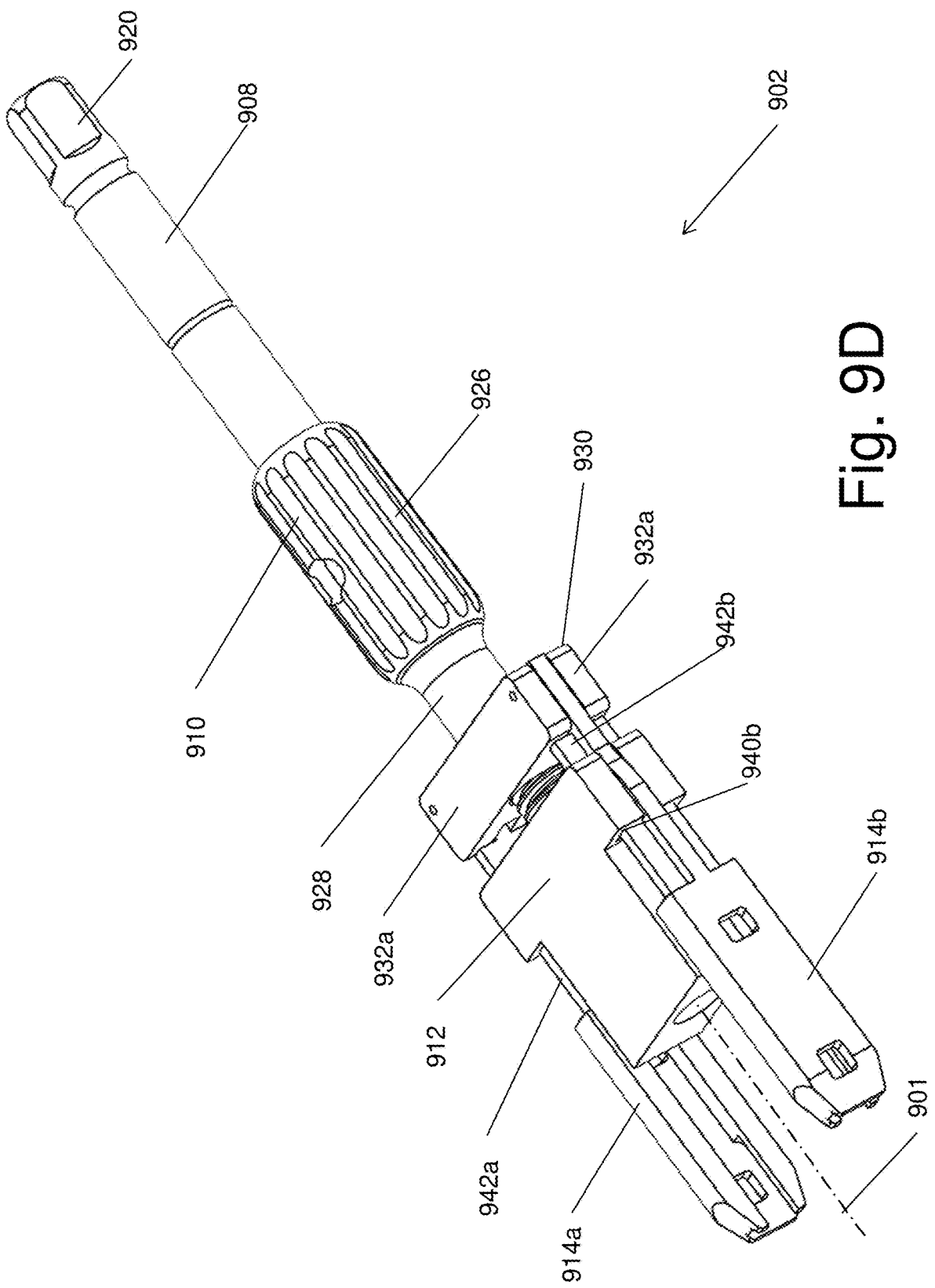
FIG. 9D is a detailed perspective view of an inserter tool with the handle removed for clarity.
Figure 9E:
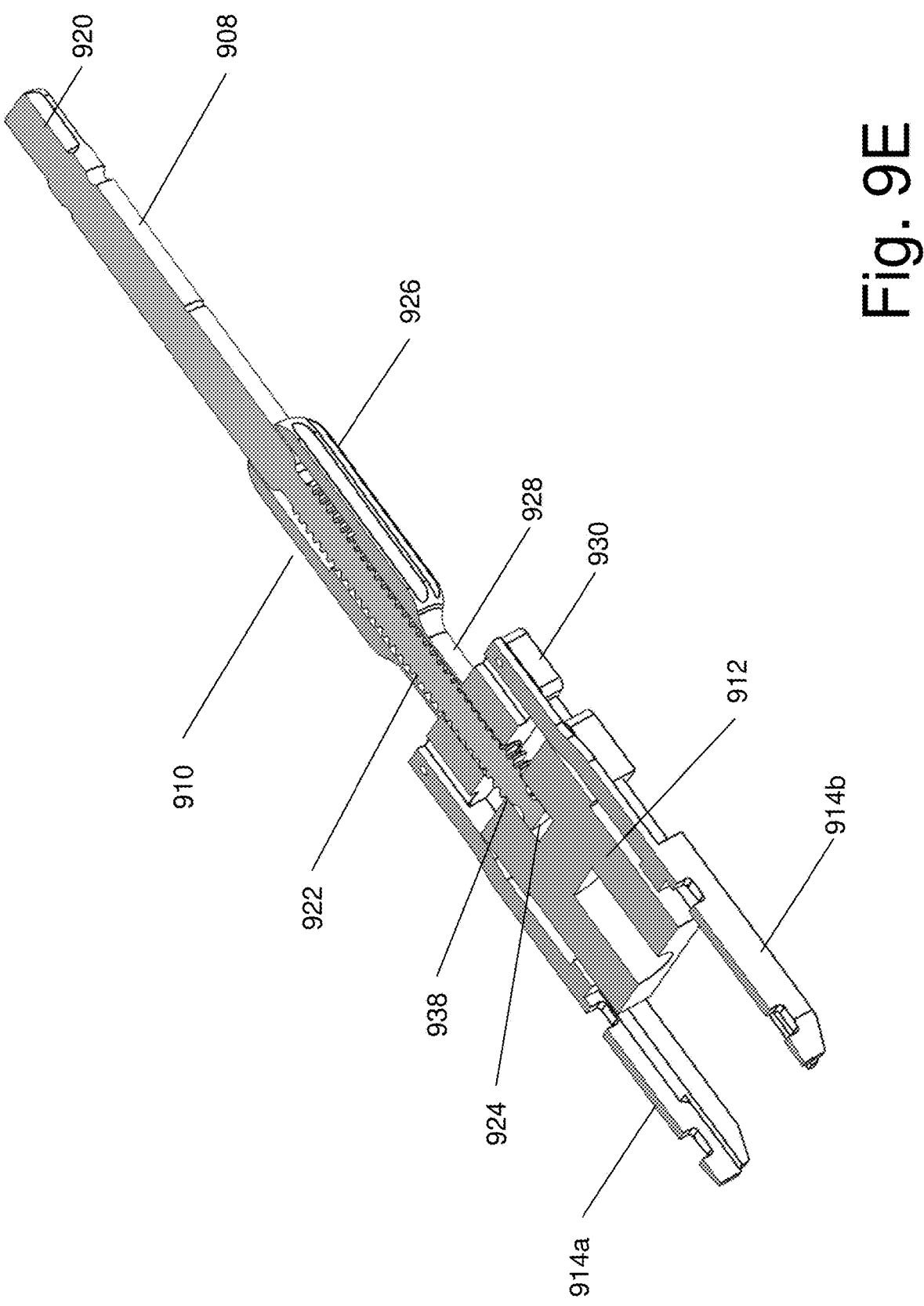
FIG. 9E is a horizontal sectional perspective view of the inserter tool of FIG. 9D.
Figure 9F:
FIG. 9F is an exploded perspective view of the inserter tool of FIG. 9D.

FIG. 9D is a perspective view of the implant insertion tool 902 with the handle 906 removed for clarity. FIG. 9E is horizontal section cut of the components illustrated in FIG. 9D. FIG. 9F is an exploded view of the components illustrated in FIG. 9D.

In certain embodiments, a proximal end 920 of the actuating rod 908 may have a rectangular, hexagonal, or other shape designed to transmit torque from the handle 906 (not shown) to the actuating rod 908 without slipping. Such as shape may be especially advantageous in embodiments where the handle 906 is removable from the actuating rod 908. In certain embodiments, the actuating rod 908 may have an outer threaded surface 922 defined over a substantial portion of its distal longitudinal length as indicated in FIG. 9E. The distal end 924 of the actuating rod may have a pin or ball connection to allow the distal end 924 to rotate without imparting a significant torsional force onto the translating element 912 (see FIGS. 9E and 9F).

In the illustrative embodiment, the fixed collar 910 comprises a gripping collar 926, a connecting collar 928, and a translation block 930. In certain embodiments, the translation block 930 has an interior through bore which has a threaded interior surface sized to rotationally mate with the outer threaded surface 922 of the actuating rod 908 (See FIG. 9E). In certain embodiments, the translation block 930 has two opposing side elements 932a and 932b (FIG. 9F). Each side element 932a and 932b has a corresponding horizontal slot 934a and 934b sized to accommodate proximal ends 936a and 936b of the side arms 914a and 914b, respectively. In certain embodiments, a pin (not shown) may be used to couple the ends 936a-936b to the opposing side elements 932a and 932b such that the side arms 914a and 914b can swing out in a transverse manner with respect to the longitudinal axis 901.

The translating element 912 has a proximal opening 938 (visible in FIG. 9E) sized to accommodate and house the distal end 924 of the actuating rod 908. In certain embodiments the translating element 912 has side channels 940a and 940b (See FIG. 9F) which are sized to loosely slide along rails 942a and 942b of the side arms 914a and 914b, respectively.

Referring back to FIG. 9A, when a user turns the handle 906, a torque is applied to the actuating rod 908. The user also holds the fixed collar 910 stationary. Because the outer threaded surface 922 of the actuating rod 908 is mated with the inner threaded bore of the translation block 930 (See FIG. 9F), the actuating rod 908 moves linearly along the axis 901 as torque is applied to its proximal end. The linear movement of the distal end 924 actuating rod 908 causes the translating element 912 to also move along the linear axis 901. The translating element 912 is rotatably coupled to the distal end 924 such that the distal end 924 can impart a linear movement to the translating element. The translating element 912 is also loosely guided by the interaction of its channels 940a and 940b and the rails 942a and 942b of the side arms 914a and 914b, respectively. The side arms 914a and 914b also keep the translating element 912 from rotating about the longitudinal axis 901. Consequently, the translating element 912 retains its radial position with respect to the longitudinal axis 901 as it is pushed or pulled along the longitudinal axis by the distal end 924 of the actuating rod.

Figure 10A:
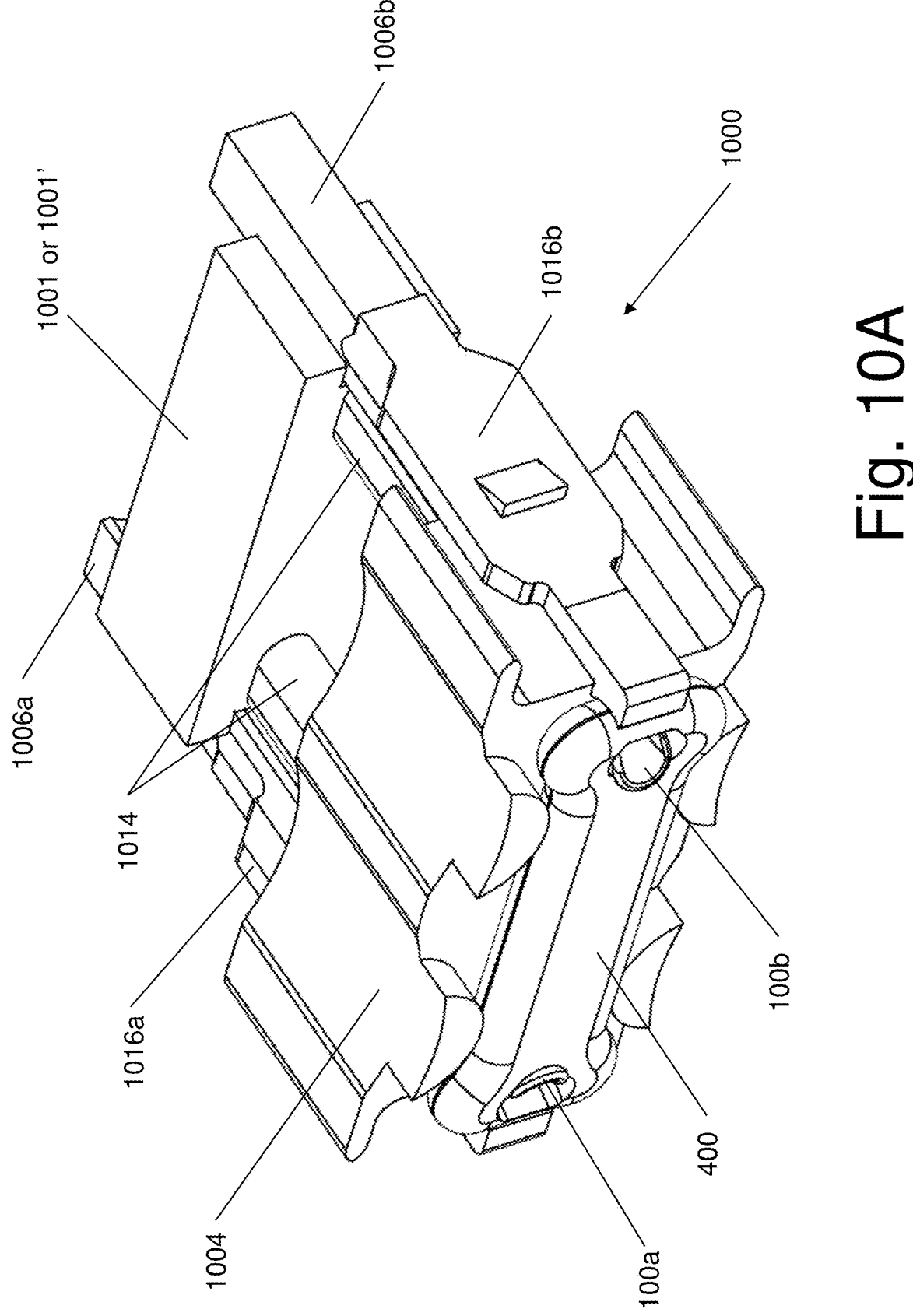
FIG. 10A is a perspective view of an implant cassette which may be used with one or more aspects of the present invention.
Figure 10B:
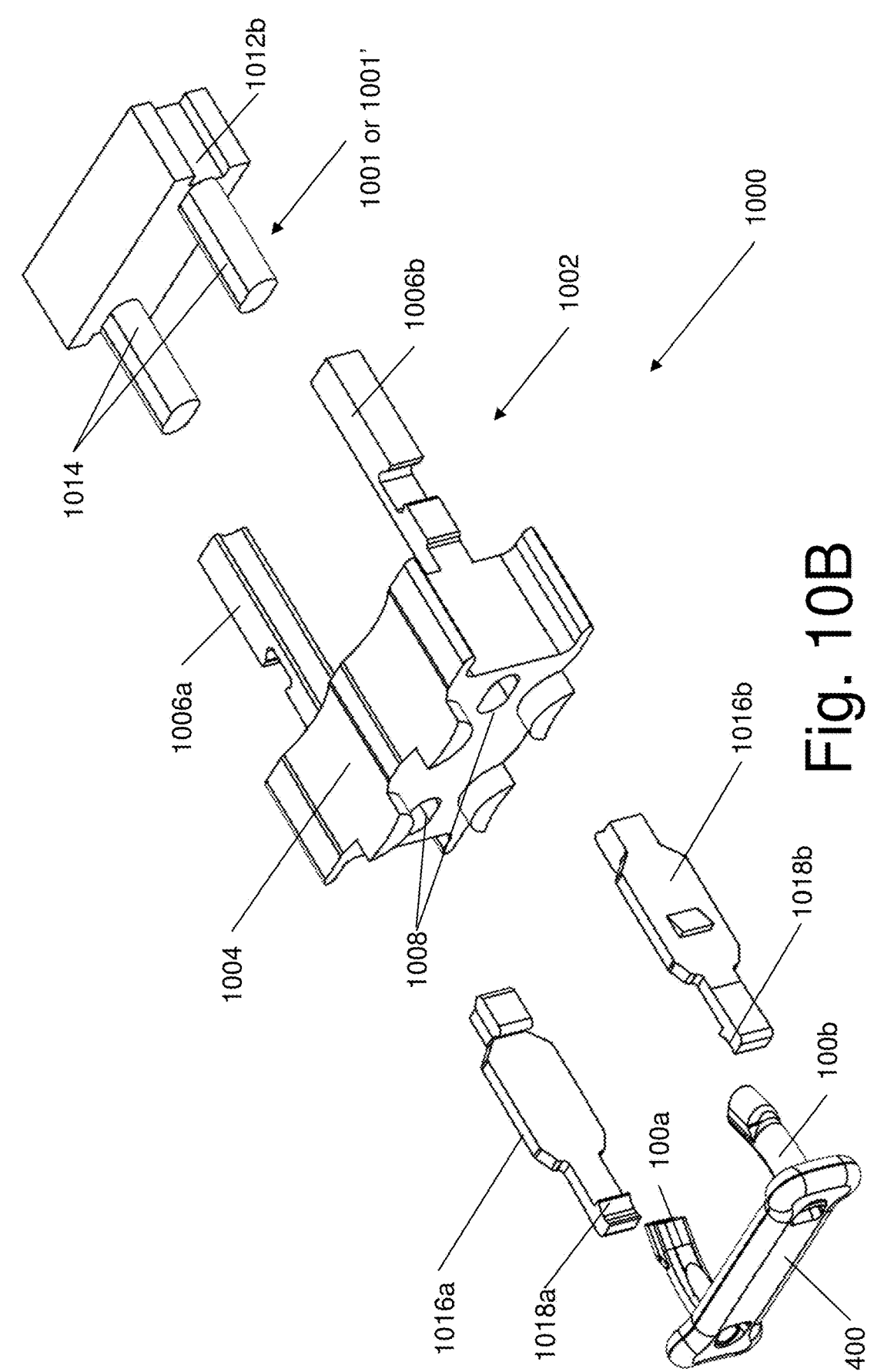
FIG. 10B is an exploded perspective view of the implant cassette of FIG. 10A.

FIG. 10A is a perspective view of one embodiment of an implant cassette 1000 in a pre-loaded condition which can be used with the implant inserter tool 902. FIG. 10B is an exploded view of the implant cassette and FIGS. 10C-10E are perspective views of horizontal section cuts of the implant cassette 1000 during various stages of deployment.

Figures 10C, 10D, 10E:
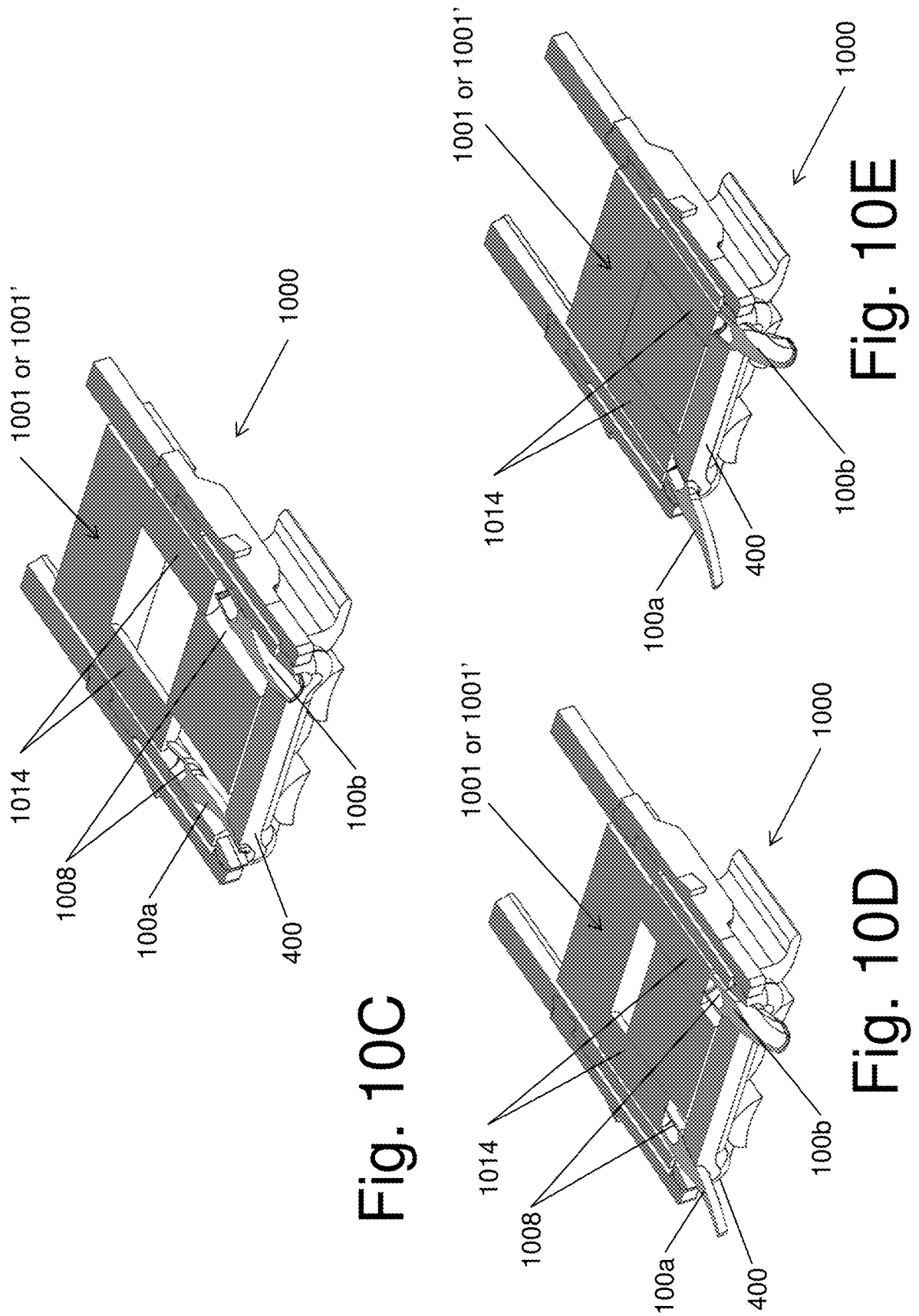
FIGS. 10C, 10D, and 10E are horizontal sectional perspective view of the implant cassette of FIG. 10A in various stages of deployment.

Turning now to FIGS. 10A to 10C, there is a mount block or mounting unit 1002 comprising a main body 1004 and guide arms 1006a and 1006b extending on each side of the main body 1004 in a longitudinal direction towards a proximal end of the cassette 1000. The main body 1004 defines a plurality of deployment channels 1008 where each deployment channel corresponds to the number of anchors preloaded in the implant. In the illustrative embodiment, there are two deployment channels 1008 corresponding to two anchors 100a and 100b of the implant 400 as discussed above. As best illustrated by FIG. 10C, when the implant cassette 1000 is in a pre-deployed configuration, the anchors 100a-100b are partially positioned within the implant 400 and partially positioned within the plurality of deployment channels 1008 where each anchor 100a-100b is at least partially within its own corresponding deployment channel. In other embodiments, the anchors 100a-100b may be entirely positioned within their respective deployment channels.

Turning back to FIG. 10B, the force transmission unit or actuator 1001 (as explained above, in some embodiments the actuator 1001' is part of the inserter tool) is positioned on the proximal side of the main body 1004 and primarily fits between the guide arms 1006a-1006b of the mounting unit 1002. Each side of the force transmission unit 1001 defines a channel 1012a-1012b (only channel 1012b is visible in FIG. 10C) sized to interact with the guide arms 1006a-1006b such that the force transmission unit 1001 can slide along the guide arms in the longitudinal direction. The proximal face of the force transmission unit 1001 is designed to interact with and receive a longitudinal linear force from the translation element 912 of the implant inserter tool 902 (see FIGS. 9A and 9B). A plurality of push rods 1014 projects from a distal face of the force transmission unit 1001. The number and location of push rods 1014 corresponds to the number and location of the plurality of deployment channels 1008 defined within the main body 1004 of the mounting unit 1002. The push rods 1014 are sized and shaped to be received by the plurality of deployment channels 1008 of the mounting unit 1002.

In certain embodiments, proximal ends of grab or retention arms 1016a-1016b are sized and shaped to couple with the guide arms 1006a and 1006b of the mounting unit 1002. Curved retaining surfaces or hooks 1018a and 1018b formed on the distal ends of the retention arms 1016a-1016b are sized to retain then release the longitudinal ends of the implant 400.

Referring now to FIGS. 9A-9D and more specifically to FIGS. 10D through 10E, a manner of using one embodiment of the implant insertion system 900 will now be described. FIG. 10C is a horizontal sectional perspective view of the implant cassette 1000 in a pre-deployed or first configuration. FIG. 10D is a horizontal sectional perspective view of the implant cassette 1000 in a mid-deployed or second configuration. FIG. 10E is a horizontal sectional perspective view of the implant cassette 1000 in a fully deployed or third configuration.

In certain embodiments, a user can use the system 900 to position the implant 400 into a surgical site as discussed above. For instance, referring back to FIGS. 5A-5E, system 900 positions the implant 400 adjacent to a first boney structure 550*a* and a second boney structure 550*b*. As discussed above, two exemplary anchors 100*a*-100*b* have been positioned inside the implant cassette 1000 and they are partially positioned (or introduced) inside the implant 400 and partially positioned inside the deployment channels 1008 of the mounting unit 1002 as indicated in FIG. 10C.

The user can then apply a rotating force to the handle 906 while holding the fixed collar 910 stationary (see FIGS. 9A through 9F, above). The rotation of the handle 906 causes a torque to be applied to the actuating rod 908. In response, the actuating rod 908 advances in a linear fashion with respect to the fixed collar 910 due to the interaction of the threaded exterior surface 922 of the actuating rod and the threaded interior surface of the fixed collar as described above. As the actuating rod 908 advances along the longitudinal axis 901, the translating element 912 is pushed towards the distal end of the inserting tool 902. This movement results in a smooth non-rotating force applied to the proximal end of the force transmission unit 1001 (or depending on the embodiment force transmission unit 1001'. For purposes of this discussion regarding the method of use the force transmission units 1001 and 1001' are interchangeable).

In response to the linear force being applied to the proximal end of the force transmission unit 1001, the transmission unit 1001 begins to move which causes the push rods 1014 to apply a smooth non-rotating force to the proximal ends of the anchors 100*a*-100*b* which are positioned in the respective deployment channels 1008 of the mounting unit 1002.

The force on the proximal ends of the anchors 100*a*-100*b* causes the anchors to move along an initial trajectory into the boney structures 550*a* and 550*b* as discussed above. As the user continues to turn the handle 906, the smooth non-rotating force continues to be applied to the proximal ends of the anchors 100*a*-100*b* which causes the anchors to move along their initial trajectory discussed above. As the offset heads of the anchors reach their respective apertures defined in the implant 400, the offset heads interact with the apertures which cause a transverse shift of the anchor and the attached boney structures 550*a* and 550*b*. This transverse shift will cause the boney structures 550*a* and 550*b* to compress against the implant 400 as discussed above until the anchors are fully deployed into the boney structures 550*a* and 550*b* as indicated by FIG. 10E and FIG. 5E (above).

Once the anchors are fully deployed, the handle 906 may be rotated in a direction opposite to the insertion rotation direction with respect to the fixed collar 910 (e.g., counterclockwise). This opposite rotation will cause the translation element 912 to move longitudinally backwards towards a proximal end of the implant insertion tool 902. As the translation element 912 moves towards the translation block 930, the side arms 914*a* and 914*b* of the implant inserter tool will rotate outwards in a direction transverse to the longitudinal axis 901 as indicated in FIG. 9B.

Because the retention arms 1016*a* and 1016*b* of the implant cassette 1000 are slidingly coupled to the side arms 914*a* and 914*b* of the inserter tool 902, the retention arms 1016*a* and 1016*b* will also rotate away from the implant 400 which will cause the retention arms 1016*a* and 1016*b* to release the deployed implant 400. Once the implant 400 has been released from the retention arms 1016*a* and 1016*b*, the inserter tool 902 may be then be removed from the surgical site. The surgical site can then be closed in a traditional manner.

The various components of certain embodiments of the inserter systems described herein may be produced from readily available materials suitable for short term tissue contact in surgery. Such materials include stainless steel alloys, titanium and its alloys, and rigid polymers including fiber reinforced polymers.

Alternative Inserter Embodiments

Figure 11A:
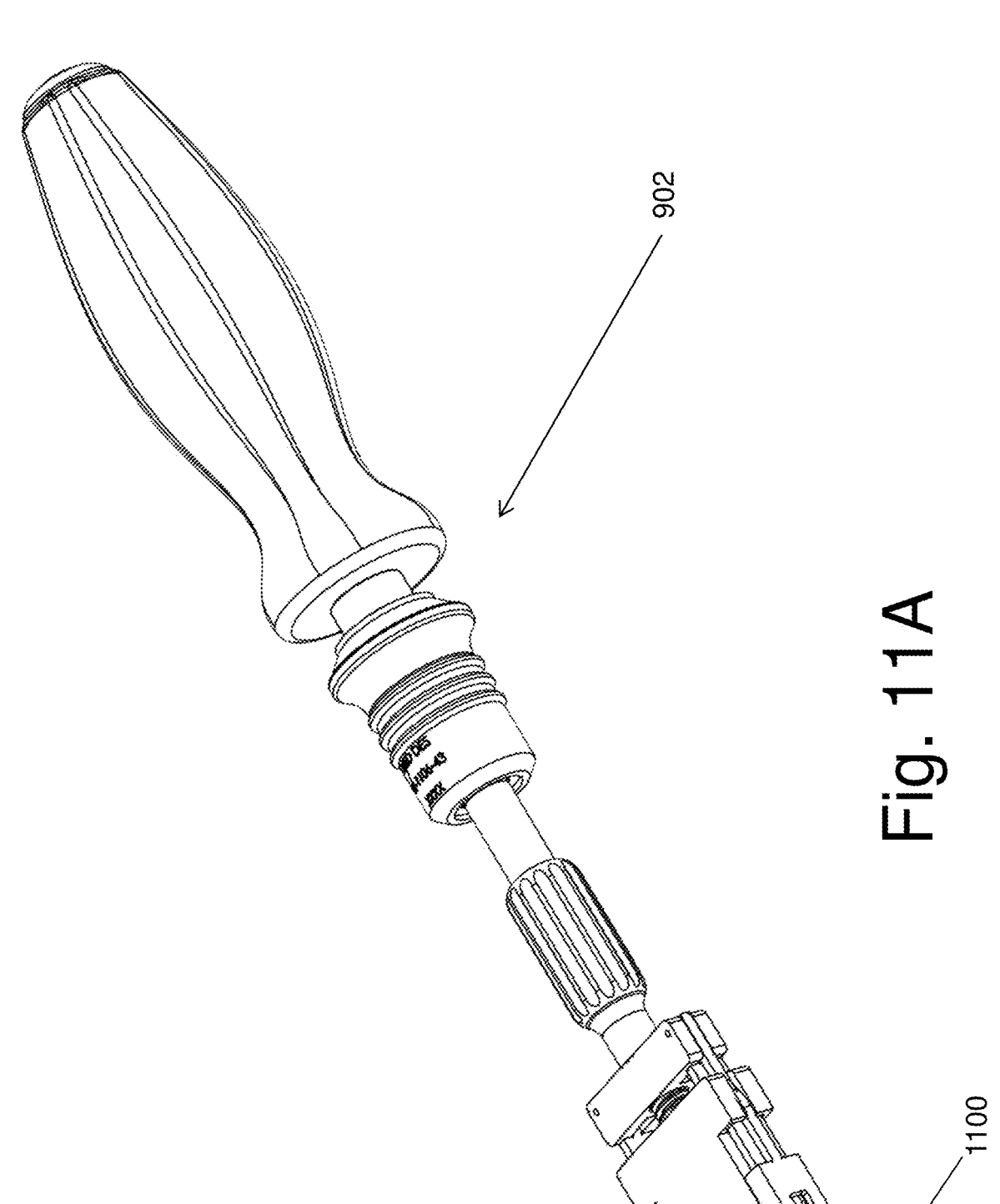
FIG. 11A is a perspective view of the implant insertion system showing an alternative implant cassette which may be used with certain embodiments of the present invention.
Figure 11B:
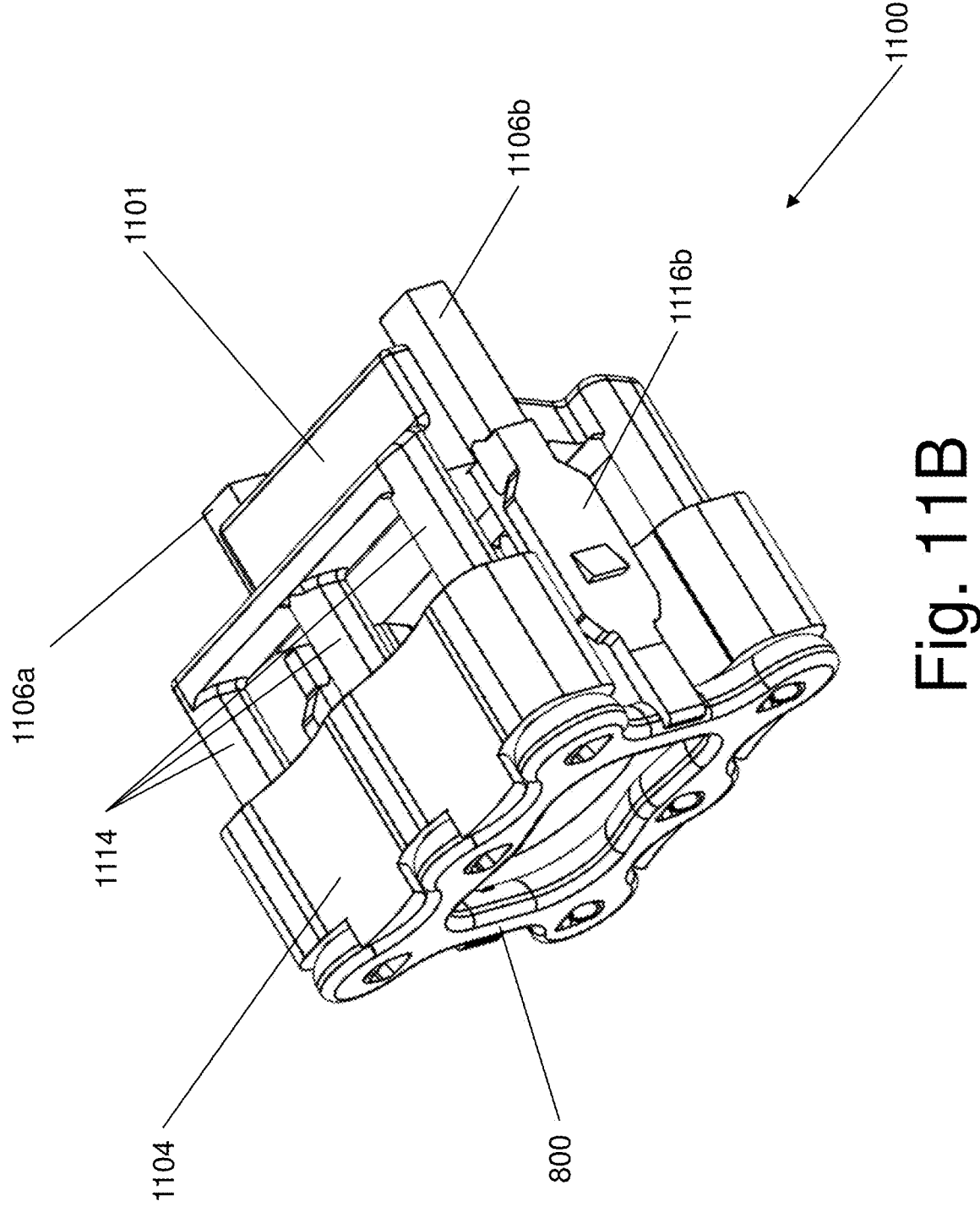
FIG. 11B is a detailed perspective view of the implant cassette illustrated in FIG. 11A.

FIG. 11A is a perspective view of another alternative embodiment of an implant cassette 1100 coupled to an insertion tool, for instance insertion tool 902 as described above. FIG. 11B a perspective view illustrating the implant cassette 1100 in greater detail and FIG. 11C is an exploded perspective view of the implant cassette 1100.

The implant cassette 1100 is conceptually similar to the implant cassette 1000 discussed above except that implant cassette 1000 includes six anchors 100*a*-100*f* and is coupled to an implant 800 discussed above in reference to FIG. 8.

Figure 11C:
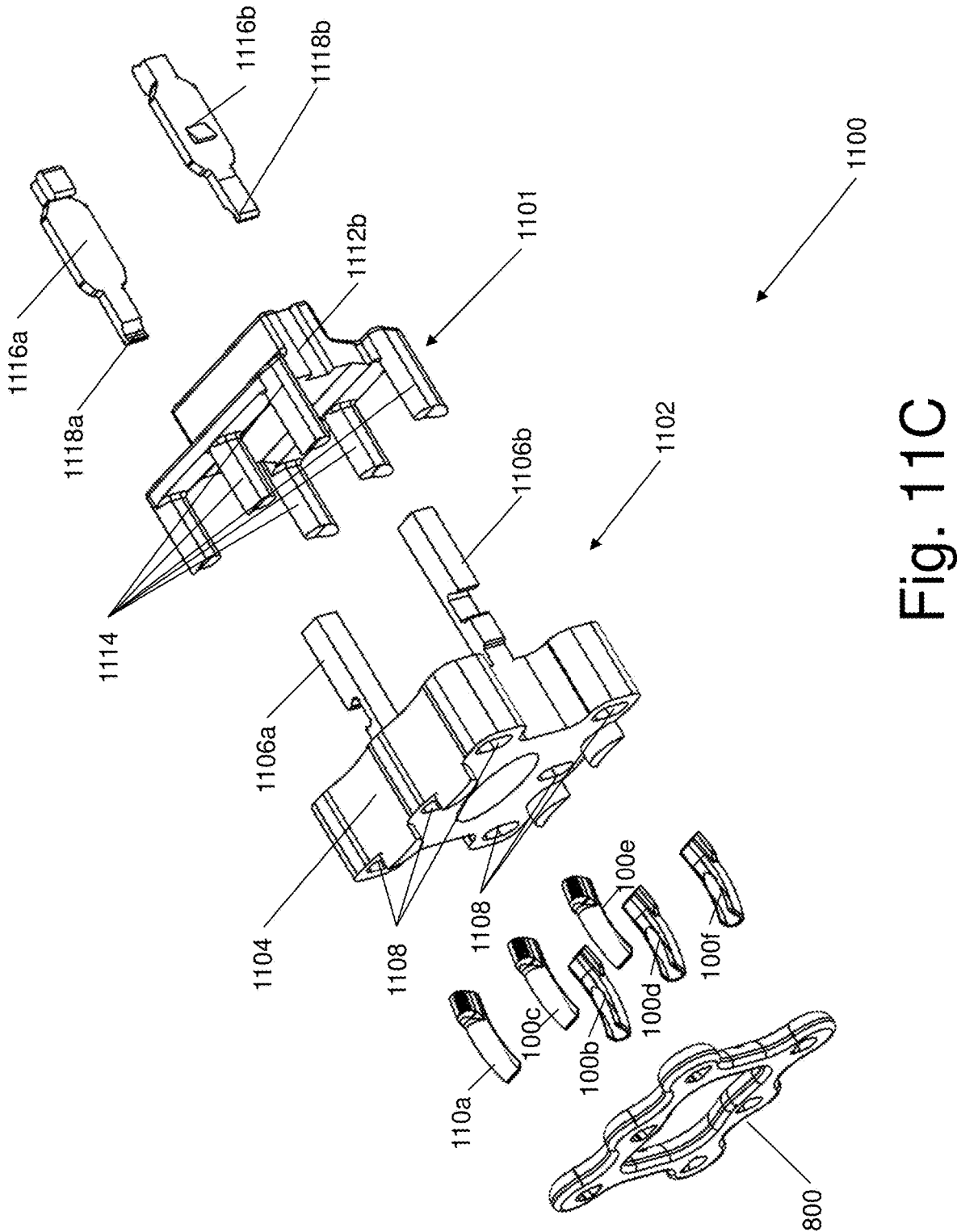
FIG. 11C is an exploded perspective view of the implant cassette illustrated in FIG. 11A.

Turning now to FIGS. 11A to 11C, there is a mount block or mounting unit 1102 comprising a main body 1104 and guide arms 1106*a* and 1106*b* extending on each side of the main body 1104 in a longitudinal direction towards a proximal end of the cassette 1100. The main body 1104 defines a plurality of deployment channels 1108 where each deployment channel corresponds to the number of anchors preloaded in the implant. In the illustrative embodiment, there are six deployment channels 1108 corresponding to six anchors 100*a*-100*f* of the implant 800 as discussed above. As described above with reference to the implant cassette 1000, when the implant cassette 1100 is in a pre-deployed configuration, the anchors 100*a*-100*f* are partially positioned within the implant 800 and partially positioned within the plurality of deployment channels 1108 where each anchor 100*a*-100*f* is at least partially within its own corresponding deployment channel. In other embodiments, the anchors 100*a*-100*b* may be entirely positioned within their respective deployment channels.

The force transmission unit or actuator 1101 is positioned on the proximal side of the main body 1104 and primarily fits between the guide arms 1106*a*-1106*b* of the mounting unit 1102. Each side of the force transmission unit 1101 defines a channel 1112*a*-1112*b* (only channel 1112*b* is visible in FIG. 11C) sized to interact with the guide arms 1106*a*-1106*b* such that the force transmission unit 1101 can slide along the guide arms in the longitudinal direction. The proximal face of the force transmission unit 1101 is designed to interact with and receive a longitudinal linear force from the translation element 912 of the implant inserter tool 902 (see FIGS. 9A and 9B). A plurality of push rods 1114 (e.g., six push rods) projects from a distal face of the force transmission unit 1101. The number and location of push rods 1114 corresponds to the number and location of the plurality of deployment channels 1108 defined within the main body 1104 of the mounting unit 1102. The push rods 1114 are sized and shaped to be received by the plurality of deployment channels 1108 of the mounting unit 1102.

In certain embodiments, proximal ends of grab or retention arms 1116a and 1116b are sized and shaped to couple with the guide arms 1106a and 1106b of the mounting unit 1102. Curved retaining surfaces or hooks 1118a and 1118b formed on the distal ends of the retention arms 1116a-1116b are sized to retain then release the longitudinal ends of the implant 800.

The implant 800 is deployed by the cassette 1100 and the inserter tool 902 in a manner described above for the deployment of the implant 400. Consequently, a description of the deployment of the anchors will not be repeated here. Reference should be made to FIGS. 10A through 10E and the associated referenced descriptions for a complete understanding of the insertion method using the cassette 1100 and the insertion tool 902.

Optional Stabilizing Systems

Figure 12A:
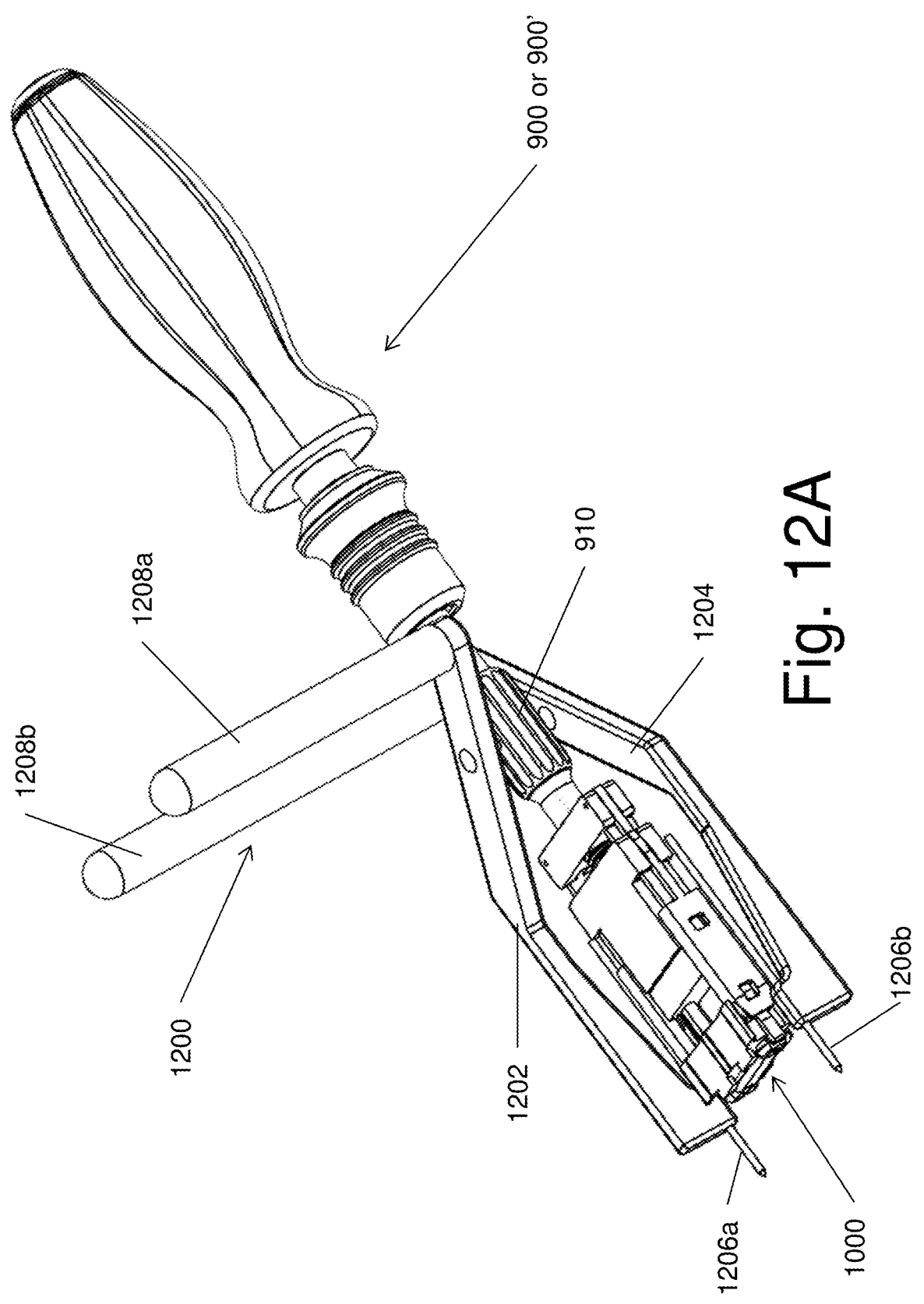
FIG. 12A is a perspective view of the implant insertion system of FIG. 9A coupled to an optional stabilizing system.
Figures 12B, 13B:
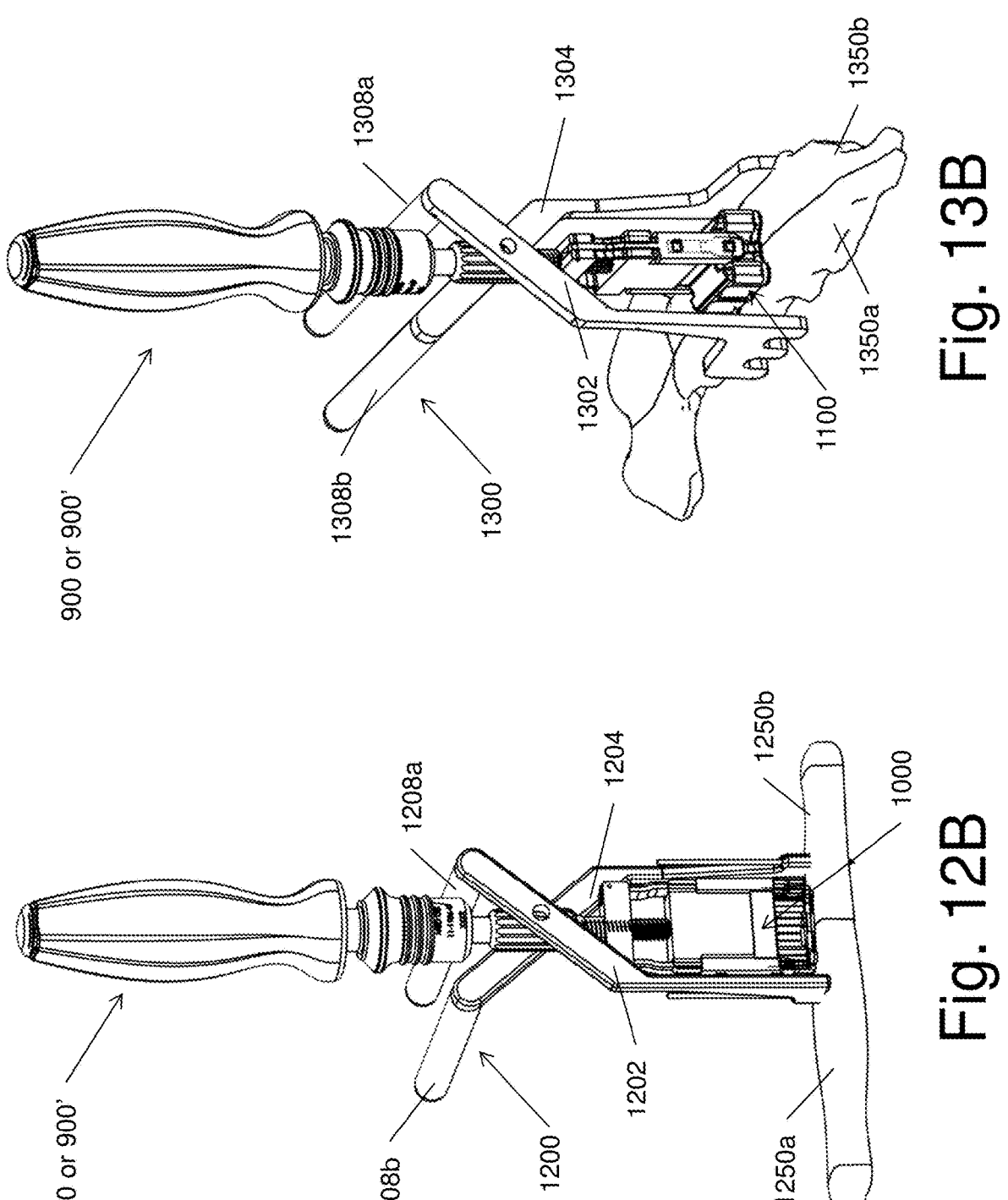
FIG. 12B is a perspective view of the implant insertion system and stabilizing system of FIG. 12A coupled to a fractured boney structure.
FIG. 13B is a perspective view of the implant insertion system and stabilizing system of FIG. 13A coupled to a split sternum.

FIG. 12A is a perspective view of the implant insertion system 900 or 900' (FIG. 9A or 9B) coupled to an optional stabilizing system 1200. FIG. 12B is a perspective view of the implant insertion system 900 or 900' and stabilizing system 1200 coupled to a fractured boney structure which is now two boney structures 1250a and 1250b. In certain embodiments, the stabilizing system 1200 assists in maintaining the position of the fragments or boney structures 1250a and 1250b during implant and anchor insertion. In certain cases, the stabilizing system 1200 provides additional macroscopic support for the systems and methods described above.

In the illustrative embodiment, the exemplary stabilization system 1200 comprises a first stabilizing arm 1202 and a second stabilizing arm 1204 coupled together with a pin connection (not shown) which acts as a fulcrum. In certain embodiments, a distal end of the stabilizing arm 1202 engages a bone pin 1206a and a distal end of the stabilizing arm 1204 engages a bone pin 1206b. In certain embodiments, the distal ends of the stabilizing arms 1202 and 1204 have grooves or apertures (not shown) defined therein for sliding over or otherwise coupling to the bone pins 1206a-1206b.

In the illustrative embodiment, the arms 1202 and 1204 are angled such that they cross to meet at a pinned connection (not shown). In certain embodiments, the pinned connection may two linearly aligned pins (not shown) positioned on opposing sides of the non-rotating collar 910 discussed above.

In certain embodiments, there may be a handle 1208a coupled to the proximal end of the arm 1202 and a handle 1208b coupled to the proximal end of the arm 1204. The handles 1208a and 1208b allow the user to close the handles together which brings the distal ends of the arms 1202 and 1204 together because the pinned connection acts as a fulcrum and the arms act as levers. When the distal ends are coupled to the pins 1206a and 1206b, bringing the handles together will cause the pins to move towards each other—which will assist in compression techniques. In other embodiments, the arms may be inverted such that bringing the handles together will cause the pins to move away from each other—which will assist in distraction techniques.

In the illustrative embodiment, the distal ends of the arms 1202 and 1204 are generally linearly aligned with longitudinal axis of the implant (such as implant 400). In other embodiments, the arms 1202 and 1204 may be coupled to a linear slide lock or linear ratchet lock to hold the arms in place once the proper position of the distal ends of the arms is obtained.

In use, the pins may be pre-existing and already coupled to the boney structures, such as boney structures 1250a and 1250b illustrated in FIG. 12B. If there are no pins in place, then the pins 1206a and 1206b may be inserted into the boney structures 1250a and 1250b as is known in the art. The arms 1202 and 1204 can slide over or otherwise engage the pins 1206a and 1206b so that when the distal ends move a force will be exerted on the pins. The user can then bring the handles 1208a and 1208b together to position the boney fragments 1250a and 1250b (which, if desired, might also cause some compression or distraction). Optionally, once the boney fragments 1250a and 1250b are in position, a locking mechanism (not shown) can be employed to maintain the position of the arms 1204 and 1204 and thus the respective position of the boney fragments 1250a and 1250b. Compression or distraction techniques and system may then be employed to insert the implants and the associated anchors as described above.

Figure 13A:
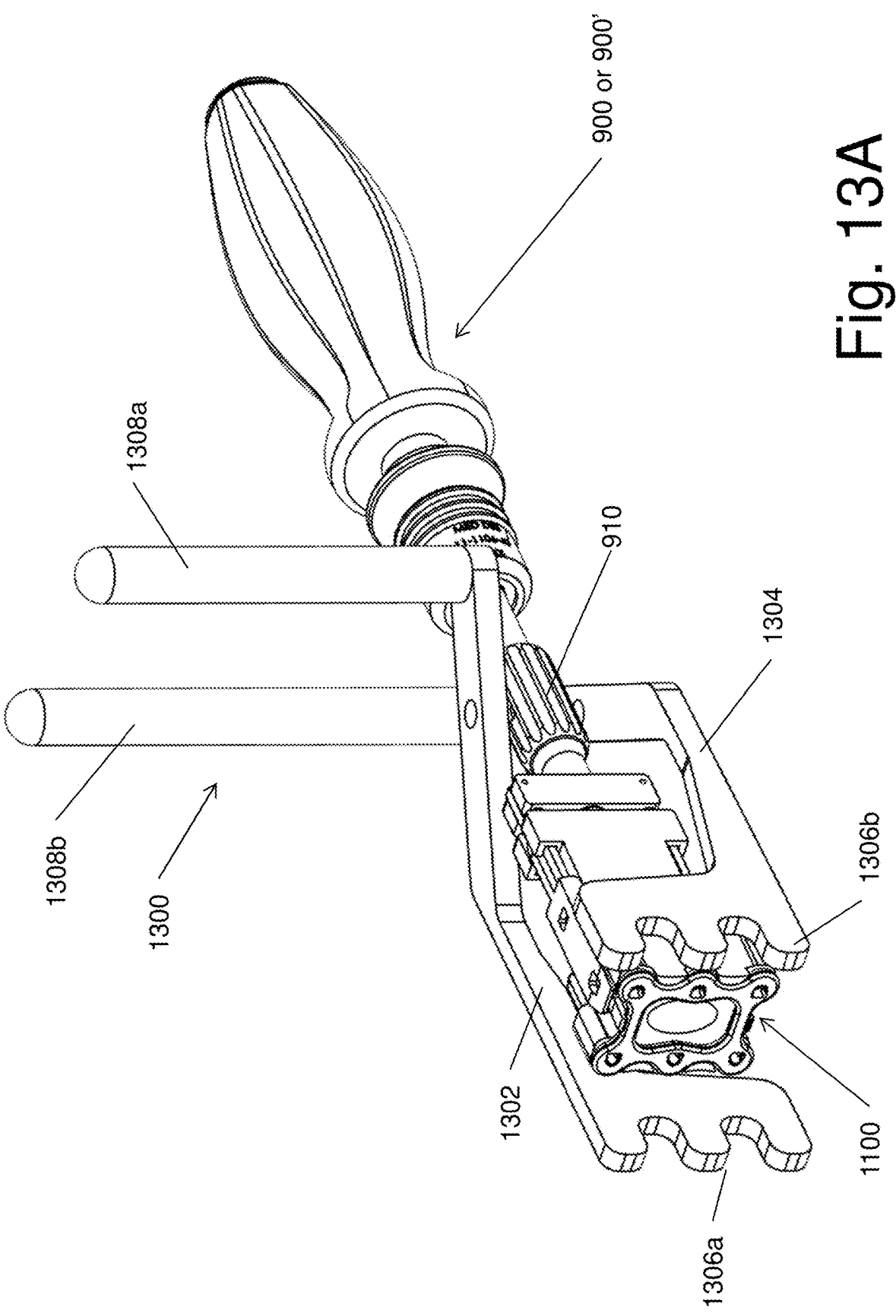
FIG. 13A is a perspective view of the implant insertion system of FIG. 9A coupled to an alternative optional stabilizing system.

FIG. 13A is a perspective view of the implant insertion system 900 or 900' coupled to an alternative and optional stabilizing system 1300. FIG. 13B is a perspective view of the implant insertion system 900 and stabilizing system 1300 coupled to a sternum that has been previously sawed apart during an open heart procedure to create a boney structure 1350a and a boney structure 1350b. In certain embodiments, the stabilizing system 1300 assists in maintaining the position of the boney structures 1350a and 1350b during implant and anchor insertion. In certain cases, the stabilizing system 1300 provides additional macroscopic support for the systems and methods described above.

In the illustrative embodiment, the exemplary stabilization system 1300 comprises a first stabilizing arm 1302 and a second stabilizing arm 1304 coupled together with a pin connection (not shown) which acts as a fulcrum. In certain embodiments, a distal end of the stabilizing arm 1302 is designed to engage a bone, such as a sternum. Consequently, the distal end of the stabilizing arm 1302 may have one or more fingers or claws 1306a designed to directly engage a boney structure. Similarly, a distal end of the stabilizing arm 1304 has one or more fingers or claws 1306b which are also designed to directly engage a bone, such as a sternum.

In the illustrative embodiment, the arms 1302 and 1304 are angled such that they cross to meet at a pinned connection (not shown). In certain embodiments, the pinned connection may two linearly aligned pins (not shown) positioned on opposing sides of the non-rotating collar 910 discussed above.

In certain embodiments, there may be a handle 1308a coupled to the proximal end of the arm 1302 and a handle 1308b coupled to the proximal end of the arm 1304. The handles 1308a and 1308b allow the user to close the handles together which brings the fingers 1306a and 1306b together because the pinned connection acts as a fulcrum and the arms act as levers.

Figure 8:
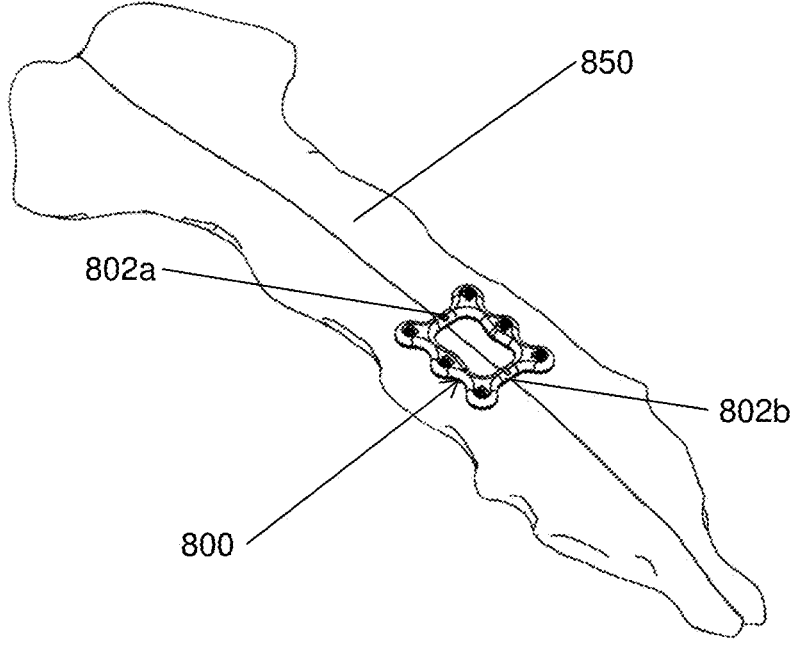
FIG. 8 is an alternative six anchor embodiment used to join and compress a sternal plate.

In the illustrative embodiment, the fingers 1306a and 1306b are linearly aligned are generally parallel to the longitudinal axis of the implant (such as implant 800 of FIG. 8 above). In other embodiments, the arms 1302 and 1304 may be coupled to a linear slide lock or linear ratchet lock to hold the arms in place once the proper position of the distal ends of the arms is obtained.

In use, the fingers 1306a and 1306b engage the boney structures 1350a and 1350b (such as two halves of a sternum) so that when the fingers 1306a-1306b move a force will be exerted on the sternum. The user can then bring the handles 1308a and 1308b together to position the boney structures 1350a and 1350b together and/or into the correct position. Optionally, once the boney structures 1350*a* and 1350*b* are in position, a locking mechanism (not shown) can be employed to maintain the position of the arms 1304 and 1304 and thus the respective position of the boney structures 1350*a* and 1350*b*. Compression techniques and systems may then be employed to insert the implants and the associated anchors as described above.

Other Embodiments

For purposes of simplification, the implant embodiments discussed above have illustrated and described with an implant and two anchors. However, the present invention contemplates the use of implant embodiment systems using more than two anchors.

In alternative embodiments, one or more anchors may be a traditional anchor without an offset head portion. For instance in the methods described in FIGS. 5A through 7F, the anchors may be replaced with a traditional anchor (either threaded or non-threaded) having a symmetrical head portion. In such cases, the corresponding aperture may be replaced with a traditional concentric aperture designed to accommodate a traditional anchor with a concentric or symmetrical head. In this alternative embodiment, the symmetrical head and concentric aperture would not cause a transverse shift as explained above. Consequently, significant compression or distraction due to movement would not occur on the side of the implant having a traditional anchor. For example in the method described in reference to FIGS. 5A-5E, if the anchor 100*b* is replaced with a traditional anchor and the aperture 410*b* is replaced with a symmetrical aperture, then only the boney structure 550*a* would move toward the boney structure 550*b*. The boney structure 550*b* would remain relatively stationary in this alternative embodiment.

While the above examples use implants where two aperture are discussed, implants may have two, four, six or more apertures and the corresponding number of anchors and still be within the scope of this invention.

For instance, FIG. 8 depicts a perspective view of a six anchor implant 800 joining a divided and re-aligned sternum 850. The implant 800 and the associated six anchors fixes and holds the sternum 850 together following a cardiac procedure.

In yet other embodiments, various components, for example the anchors 100 may be made from nickel titanium (also known as Nitinol®) or another shape memory alloy. The anchor would have a very specific shape at a cooler temperature, such as room temperature. Once inserted into a human body, the metal would rise to a body temperature which will cause the anchor to change shape to enhance compression.

For instance, at or below room temperature a straight anchor might be inserted. At body temperature, the straight anchor turns into a curved anchor and applies additional compression or distraction. Similarly, a curved anchor could turn into a straight anchor at body temperature to enhance either compression or distraction.

In yet other embodiments, the implant or parts of the implant may be formed of a shape memory alloy. For example in FIG. 8, the joining members 802*a* and 802*b* may be made of Nitinol® and be straight at a cooler temperature, such as room temperature. Once inserted into a human body and the surgical procedure completed, the temperature of the joining members 802*a* and 802*b* would rise to a body temperature which will cause the joining members to curve. As joining members 802*a*-802*b* curve (either inwards or outwards), the joining members will begin to pull on the rest of the implant, which will cause additional compression.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112 (f). Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word "means" are not intended to fall under 35 USC 112 (f).

The foregoing description of the embodiments of the invention has been presented for the purposes of illustration and description. It is not intended to be exhaustive or to limit the invention to the precise form disclosed. Many combinations, modifications and variations are possible in light of the above teaching. For instance, in certain embodiments, each of the above described components and features may be individually or sequentially combined with other components or features and still be within the scope of the present invention. Undescribed embodiments which have interchanged components are still within the scope of the present invention. It is intended that the scope of the invention be limited not by this detailed description, but rather by the claims.

For instance, in certain embodiments there may be a method for joining a first boney structure to a second boney structure, the method comprising: positioning a supra implant adjacent to the first boney structure and to the second boney structure; introducing a first distal end of a first non-threaded anchor into a first non-threaded aperture defined within the supra implant, introducing a second distal end of a second non-threaded anchor into a second non-threaded aperture defined within the supra implant, applying a first non-torsional force onto a first proximal end of a first offset head of the first non-threaded anchor to drive the first distal end through the first aperture, and into the first boney structure along a first trajectory; applying a second non-torsional force onto a second proximal end of a second offset head of the second non-threaded anchor to drive the second distal end through the second aperture, and into the second boney structure along a second trajectory; continuing to apply the first non-torsional force onto the first proximal end of the first offset head as the first offset head reaches a first sloped engagement surface of the first aperture; continuing to apply the second non-torsional force onto the second proximal end of the second offset head as the second offset head reaches a second sloped engagement surface of the second aperture; continuing to apply the first non-torsional force onto the first proximal end of the first offset head to cause the first offset head to interact with the first engagement surface of first aperture to move the first offset head transversely with respect to the first trajectory to cause the first boney structure to also move transversely with respect to the first trajectory; and continuing to apply the second non-torsional force onto the second proximal end of the second offset head to cause the second offset head to interact with the second engagement surface of second aperture to move the second offset head transversely with respect to the second trajectory to cause the second boney structure to also move transversely with respect to the first trajectory.

Additionally, there may be an embodiment described above wherein the transverse movement of the first boney structure and a transverse movement of the second boney structure causes compression between the first boney structure and the second boney structure.

Additionally, there may be an embodiment described above wherein a transverse movement of the first boney structure and the transverse movement of the second boney structure causes distraction between the first boney structure and the second boney structure.

Certain embodiments may also include: introducing a third distal end of a third non-threaded anchor into a third non-threaded aperture defined within the supra implant, applying a third non-torsional force onto a third proximal end of a third offset head of the third non-threaded anchor to drive the third distal end through the third aperture, and into the first boney structure along a third trajectory; continuing to apply the third non-torsional force onto the third proximal end of the third offset head as the third offset head reaches a third sloped engagement surface of the third aperture; and continuing to apply the third non-torsional force onto the third proximal end of the third offset head to cause the third offset head to interact with the third engagement surface of third aperture to move the third offset head transversely with respect to the third trajectory to cause the first boney structure to also move transversely with respect to the third trajectory.

Certain embodiments may also include: introducing a fourth distal end of a fourth non-threaded anchor into a fourth non-threaded aperture defined within the supra implant, applying a fourth non-torsional force onto a fourth proximal end of a fourth offset head of the fourth non-threaded anchor to drive the fourth distal end through the fourth aperture, and into the second boney structure along a fourth trajectory; continuing to apply the fourth non-torsional force onto the fourth proximal end of the fourth offset head as the fourth offset head reaches a fourth sloped engagement surface of the fourth aperture; and continuing to apply the fourth non-torsional force onto the fourth proximal end of the fourth offset head to cause the fourth offset head to interact with the fourth engagement surface of fourth aperture to move the fourth offset head transversely with respect to the fourth trajectory to cause the second boney structure to also move transversely with respect to the fourth trajectory.

Additionally, there may be an embodiment described above wherein the causing the first offset head to interact with the first engagement surface of first aperture to move the first offset head transversely comprises applying a first force from the first engagement surface onto a first offset portion of the first offset head.

Additionally, there may be an embodiment described above wherein the causing the second offset head to interact with the second engagement surface of second aperture to move the second offset head transversely comprises applying a second force from the second engagement surface onto a second offset portion of the second offset head.

Additionally, there may be an embodiment described above wherein a direction of movement of the first offset head is opposite to a direction of the movement of the second offset head.

Additionally, there may be an embodiment described above, wherein a direction of movement of the first offset head is linearly aligned with the direction of the movement of the second offset head.

Certain embodiments may also include: slidingly engaging a first side rail of the first elongated body with a first side recess defined within the first aperture of the implant; and disengaging the first side rail of the first elongated body with the first side recess to cause a transverse shift of the first elongated body with respect to the first trajectory.

Certain embodiments may also include: slidingly engaging a second side rail of the first elongated body with a second side recess defined within the first aperture of the implant; and disengaging the second side rail of the first elongated body with the second side recess to cause the transverse shift of the first elongated body with respect to the first trajectory.

Certain embodiments may also include: slidingly engaging a first stepped surface of the first elongated body with a first engaging surface of the first aperture; and disengaging the first stepped surface of the first elongated body with the first engaging surface of the first aperture to cause a transverse shift of the elongated body with respect to the first trajectory.

In other embodiments, a stabilizing system may be used in conjunction with the inserter system described above. In such embodiments, the stabilizing system may include a first arm and a second arm coupled together at a pinned connection. In certain embodiments, the pinned connection may be opposing pins coupled to a non-rotating collar of the inserter system.

In some embodiments, proximal ends of first and second arms are coupled to handles for manipulating the position of the distal ends wherein the distal ends have engagement means for coupling to one or more boney structures. In some embodiments, the engagement means is a groove or aperture for coupling to a bone pin which is coupled to a boney structure. In yet other embodiments, the engagement means is a plurality of fingers or claws for directly engaging a boney structure.

In certain embodiments, the stabilizing system may also including a locking means for locking the position of the arms in place once the desired positioning has been achieved. In certain embodiments, the locking means is a linear ratchet mechanism or a linear sliding lock which may be coupled to both arms and handles.

In yet other embodiments, there may be a supra implant system for joining boney structures comprising: a first non-threaded anchor having a first center axis including, a first non-threaded elongated body; a first non-threaded head coupled to a proximal end of the elongated body, the first head including, a concentric portion of the first head that is substantially concentric to the center axis, and an offset portion of the first head that is offset from the center axis; a second non-threaded anchor having a second center axis including, a second non-threaded elongated body; a second non-threaded head coupled to a proximal end of the elongated body, the second head including, a concentric portion of the second head that is substantially concentric to the center axis, and an offset portion of the second head that is offset from the center axis; a supra implant including, a first end portion including a first aperture defined therein, the first aperture having a first sloped engagement surface, the first aperture sized and shaped to fully accept the first head only when the first sloped engagement surface engages the offset portion of the first head to force a first transverse movement of the first head; a second end portion including a second aperture defined therein, the second aperture having a second sloped engagement surface, the second aperture sized and shaped to fully accept the second head only when the second sloped engagement surface engages the offset portion of the second head to force a second transverse movement of the second; and a main body portion joining the first end portion to the second end portion.

Additionally, there may be an embodiment described above wherein the first sloped engagement surface is a first force applying surface sized and shaped to assert a first transverse force on the offset portion of the first head as the offset portion of the first head slidingly engages the first force applying surface.

Certain embodiments may also include: a first side rail protruding from the first elongated body of the first non-threaded anchor; and a first side recess defined within the first aperture sized and positioned within the aperture to allow the first side rail to pass therethrough when the first elongated body follows the first trajectory.

Certain embodiments may also include: a second side rail protruding from the first elongated body of the first non-threaded anchor; and a second side recess defined within the first aperture sized and positioned within the first aperture to allow the second side rail to pass therethrough when the first elongated body follows the second trajectory.

Certain embodiments may also include: a first longitudinal step protruding from one side and substantially along a majority of a length of the first elongated body, a surface defined within the first aperture sized and shaped to slidingly engage the first longitudinal step.

Additionally, there may be an embodiment described above wherein the first aperture is longitudinally aligned with the second aperture.

Certain embodiments may also include: a third non-threaded anchor having a third center axis including, a third non-threaded elongated body; a third non-threaded head coupled to a proximal end of the elongated body, the third head including, a concentric portion of the third head that is substantially concentric to the center axis, an offset portion of the third head that is offset from the center axis; and a third aperture defined therein, the third aperture having a third sloped engagement surface, the third aperture shaped to fully accept the third head only when the third sloped engagement surface engages the offset portion of the third head to force a third transverse movement of the third head.

Certain embodiments may also include: a fourth non-threaded anchor having a fourth center axis including, a fourth non-threaded elongated body; a fourth non-threaded head coupled to a proximal end of the elongated body, the fourth head including, a concentric portion of the fourth head that is substantially concentric to the center axis, an offset portion of the fourth head that is offset from the center axis; and a fourth aperture defined therein, the fourth aperture having a fourth sloped engagement surface, the fourth aperture shaped to fully accept the fourth head only when the fourth sloped engagement surface engages the offset portion of the fourth head to force a fourth transverse movement of the fourth head.

Certain embodiments of the method described above may also comprise stabilizing the position of the first and second boney structures before insertion of the anchors and implants.

Certain embodiments may also comprise coupling the first boney structure to a first arm and a second boney structure to a second arm and rotating both arms about a fulcrum to position the boney structures.

Embodiments may include the above method wherein the rotation causes compression or distraction of the boney structures.

Embodiments may include the above method wherein the coupling comprises attaching a pin to the boney structure and sliding an end of the arm over the pin.

Embodiments may include the above method wherein the coupling comprises engaging a plurality of fingers adjacent to a boney structure.

Embodiments may include locking the arms after the arms are in a desired position.

The invention claimed is:

1. A supra implant system for joining boney structures comprising:
   a first non-threaded anchor having a first center axis including,
      a first non-threaded elongated body;
      a first non-threaded head coupled to a proximal end of the elongated body, the first head including,
         a concentric portion of the first head that is substantially concentric to the center axis, and
         an offset portion of the first head that is offset from the center axis;
   a second non-threaded anchor having a second center axis including,
      a second non-threaded elongated body;
      a second non-threaded head coupled to a proximal end of the elongated body, the second head including,
         a concentric portion of the second head that is substantially concentric to the center axis, and
         an offset portion of the second head that is offset from the center axis;
   a supra implant including,
      a first end portion including a first aperture defined therein, the first aperture having a first rigid engagement feature, the first aperture sized and shaped to fully accept the first head only when the first rigid engagement feature engages the offset portion of the first head to force a first transverse movement of the first head;
      a second end portion including a second aperture defined therein, the second aperture having a second rigid engagement feature, the second aperture sized and shaped to fully accept the second head only when the second rigid engagement feature engages the offset portion of the second head to force a second transverse movement of the second, wherein the second transverse movement is in an opposite direction relative to the first transverse movement; and
      a main body portion joining the first end portion to the second end portion.

2. The system of claim 1, wherein the first engagement feature is a first force applying surface sized and shaped to assert first transverse force on the offset portion of the first head as the offset portion of the first head slidingly engages the first force applying surface.

3. The system of claim 1, wherein the first aperture incudes a first opposing sloped surface opposing the first rigid engagement feature and the second aperture includes a second opposing sloped surface opposing the second rigid engagement feature.

4. The system of claim 1, wherein the first aperture is longitudinally aligned with the second aperture.

5. The system of claim 1, further comprising:

a third non-threaded anchor having a third center axis including, a third non-threaded elongated body;

a third non-threaded head coupled to a proximal end of the elongated body, the third head including, a concentric portion of the third head that is substantially concentric to the center axis, an offset portion of the third head that is offset from the center axis; and a third aperture defined therein, the third aperture having a third rigid engagement feature, the third aperture shaped to fully accept the third head only when the third rigid engagement feature engages the offset portion of the third head to force a third transverse movement of the third head.

6. The system of claim 5, further comprising:

a fourth non-threaded anchor having a fourth center axis including, a fourth non-threaded elongated body;

a fourth non-threaded head coupled to a proximal end of the elongated body, the fourth head including, a concentric portion of the fourth head that is substantially concentric to the center axis, an offset portion of the fourth head that is offset from the center axis; and a fourth aperture defined therein, the fourth aperture having a fourth rigid engagement feature, the fourth aperture shaped to fully accept the fourth head only when the fourth rigid engagement feature engages the offset portion of the fourth head to force a fourth transverse movement of the fourth head.

7. The system of claim 1, further comprising:

a first side rail protruding from the first elongated body of the first non-threaded anchor; and a first side recess defined within the first aperture sized and positioned within the aperture to allow the first side rail to pass therethrough when the first elongated body follows a first trajectory.

8. The system of claim 1, further comprising:

a second side rail protruding from the first elongated body of the first non-threaded anchor; and a second side recess defined within the first aperture sized and positioned within the first aperture to allow the second side rail to pass therethrough when the first elongated body follows a second trajectory.

9. The system of claim 1, further comprising:

a first longitudinal step protruding from one side and substantially along a majority of a length of the first elongated body, a surface defined within the first aperture sized and shaped to slidingly engage the first longitudinal step.

* * * * *